(12) United States Patent
Metz et al.

(10) Patent No.: US 7,211,597 B2
(45) Date of Patent: May 1, 2007

(54) SUBSTITUTED PYRAZOLYL COMPOUNDS FOR THE TREATMENT OF INFLAMMATION

(76) Inventors: Suzanne Metz, 525 Westernmill Dr., Chesterfield, MO (US) 63017; Michael Clare, 5154 W. Brown St., Skokie, IL (US) 60077; Joyce Z. Crich, 1501 G Topp La., Glenview, IL (US) 60025; Timothy J. Hagen, 1920 Madison Ave., Gurnee, IL (US) 60031; Gunnar J. Hanson, 7410 Keystone Ave., Skokie, IL (US) 60077; He Huang, 1121 Whitfield Rd., Northbrook, IL (US) 60062; Stephen C. Houdek, 1538 Van Buren Ave., Des Plaines, IL (US) 60018; Michael A. Stealey, 502 Juniper Pkwy., Libertyville, IL (US) 60048; Michael L. Vazquez, 614 Castle Meadows Ct., Ballwin, MO (US) 63021; Richard M. Weier, 240 Hickory Ct., Lake Bluff, IL (US) 60044; Xiangdong Xu, 7498 Abbey Rd., Gurnee, IL (US) 60031

( * ) Notice: Subject to any disclaimer, the term of this patent is extended or adjusted under 35 U.S.C. 154(b) by 150 days.

(21) Appl. No.: 10/247,028

(22) Filed: Sep. 19, 2002

(65) Prior Publication Data

US 2003/0114432 A1 Jun. 19, 2003

Related U.S. Application Data

(60) Provisional application No. 60/323,297, filed on Sep. 19, 2001, and provisional application No. 60/383,226, filed on May 24, 2002.

(51) Int. Cl.
C07D 491/052 (2006.01)
C07D 471/04 (2006.01)
A61K 31/4162 (2006.01)
A61K 31/437 (2006.01)
A61K 29/00 (2006.01)

(52) U.S. Cl. .................. 514/406; 548/364.4; 514/407; 546/82

(58) Field of Classification Search ............ 548/364.4; 514/406, 407
See application file for complete search history.

(56) References Cited

U.S. PATENT DOCUMENTS

| 3,940,418 | A | 2/1976 | Hamilton | 260/310 |
|---|---|---|---|---|
| 4,678,499 | A | 7/1987 | Pasteris et al. | 71/90 |
| 4,803,193 | A | 2/1989 | Kanda et al. | 503/209 |
| 4,816,467 | A | 3/1989 | Doria et al. | 514/333 |
| 5,196,445 | A | 3/1993 | Doria et al. | 514/405 |
| 5,206,258 | A | 4/1993 | Doria et al. | 514/403 |
| 5,260,328 | A | 11/1993 | Doria et al. | 514/400 |
| 5,521,207 | A | 5/1996 | Graneto | 514/406 |
| 5,547,975 | A | 8/1996 | Talley et al. | 514/406 |
| 5,565,482 | A | 10/1996 | Talley et al. | 514/406 |
| 5,670,532 | A | 9/1997 | Talley et al. | 514/403 |
| 5,886,016 | A | 3/1999 | Talley et al. | 514/403 |

FOREIGN PATENT DOCUMENTS

| EP | 0 347 773 B1 | 4/1993 |
|---|---|---|
| EP | 1 142 889 A1 | 10/2001 |
| GB | 2 227 741 A | 8/1990 |
| WO | WO 96/09293 | 3/1996 |
| WO | WO 96/09304 | 3/1996 |
| WO | WO 97/11704 | 4/1997 |
| WO | WO 97/38986 | 10/1997 |
| WO | WO 99/55335 | 11/1999 |

OTHER PUBLICATIONS

Colotta, et. al., *American Chemical Society*, vol. 33, No. 9 (1990) 2646–2651.
Melani, et. al., *American Chemical Society*, vol. 29, No. 2 (1986) 291–295.
Doria, et. al., *Il Farmaco*, 46 (7,8) (1991) 843–860.
Fravolini, et. al., *Il Farmaco*, vol. 33, Fasc. 11, (1978) 855–865.

*Primary Examiner*—Mark L. Berch
*Assistant Examiner*—Kahsay Habte

(57) ABSTRACT

The present invention relates to compounds of Formula I:

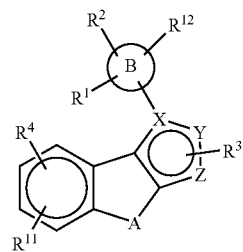

wherein A is $(CH_2)_m$-Q-$(CH_2)_n$, wherein each $CH_2$ may be independently substituted with one or more substitution selected from the group consisting of: hydroxy, halo, alkoxy, lower alkyl, amino, aminoalkyl, alkylamino, alkenyl, and alkynyl; B is a 5 or 6 membered heteroaryl, or aryl, optionally saturated, or optionally substituted with $R^1$, $R^2$, or $R^{12}$; X is selected from the group consisting of: N and C; and Y and Z are independently selected from the group consisting of: N, C, CH, $CR^3$, S, and O; compositions comprising such compounds, intermediates thereof, methods of making such compounds, and methods for treating cancer, inflammation, and inflammation-associated disorders, such as arthritis.

20 Claims, No Drawings

SUBSTITUTED PYRAZOLYL COMPOUNDS FOR THE TREATMENT OF INFLAMMATION

The present application claims priority under Title 35, United States Code, §119 to U.S. Provisional application Ser. No. 60/323,297, filed Sep. 19, 2001, and U.S. Provisional application Ser. No. 60/383,226, filed May 24, 2002, which are incorporated by reference in their entirety as if written herein.

FIELD OF THE INVENTION

The present invention in general is in the field of anti-inflammatory pharmaceutical agents and specifically relates to substituted pyrazolyl derivatives, compositions comprising such, and methods for treating cancer, inflammation, and inflammation-associated disorders, such as arthritis.

BACKGROUND OF THE INVENTION

The following description of the background of the invention is provided to aid in the understanding the invention, but is not admitted to be or describe prior art to the invention.

NF-κB is a ubiquitous transcription factor that plays a prominent role in the activation of the immune system and in stress responses by regulating the transcription of many early, inducible genes including proinflammatory cytokines, adhesion molecules, growth factors, enzymes, and receptors (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). Specificity of gene expression is determined at a cellular level by a diverse array of external stimuli such as bacterial products including LPS, as well as cytokines, most importantly tumor necrosis factor-α (TNFα) and interleukin-β (IL1β). Through the synergistic interaction with other transcription factors, further specificity can be achieved while maintaining enormous potential to coordinately induce a large number of functionally related genes. NF-κB is composed of homo and heterodimers of the Rel protein family and is sequestered in an inactive form in the cytoplasm by members of the IκB family of inhibitory proteins (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). IκBs mask the nuclear localization signal on NF-κB, preventing nuclear translocation and hence DNA binding to the promoter regions of responsive genes. Stimulation of cells with an agonist that activates NF-κB leads to a series of biochemical signals, ultimately resulting in the phosphorylation, ubiquitinylation, and degradation of IκBs, thereby releasing NF-κB for nuclear translocation (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). Recently, two IκB kinases (IKK1 or IKKα and IKK2 or IKKβ), which phosphorylate IκBs and thereby initiate their degradation, have been cloned and characterized by a number of laboratories (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). The catalytic subunits, IKK1 and IKK2, are similar structurally as well as enzymatically and exist as a heterodimer in a large protein complex referred to as the IKK signalsome (Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. And Goeddel, D. V. (1997) *Science* 278, 866–869). A third protein, NEMO (IKKγ, IKKAP1), is a regulatory adapter protein necessary for IKK activation and kinase activity (Yamaoka, S., Courtois, G., Bessia, C., Whiteside, S. T., Weil, R., Agou, F., Kirk, H. E., Kay, R. J., and Ireal, A. (1998) *Cell* 93, 1231–1240; Rothwarf, D. M., Zandi, E., Natoli, G., Karin, M. (1998) *Nature* 395, 297; Mercurio, F., Murray, B. W., Shevchenko, A., Bennet, B. L., Young, D. B., Li, J. W., Pascual, G., Motiwala, A., Zhu, H., Mann, M and Manning, A. M. (1999) *Mol. Cell. Biol.* 2, 1526–1538). IKK1 and IKK2 are co-expressed in most human adult tissues as well as in different developmental stages of mouse embryos (Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. and Goeddel, D. V. (1997) *Science* 278, 866–869; Hu, M. C. T., and Wang, Y. (1998) *Gene* 222, 31–40). This kinase complex appears to represent a critical, common denominator in the activation of NF-κB in a number of signal transduction pathways stimulated by a variety of agonists including cytokines, such as TNFα and IL1β, microbial products such as LPS and viral proteins such as TAX, as well as phorbol esters, oxidizing agents and serine/tyrosine phosphatases (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342).

IKK1 (also termed IKKα; Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. And Roa, A. (1997) *Science* 278, 860–866) was cloned simultaneously by standard biochemical purification of the IκB kinase activity from TNFα stimulated HeLa S3 cells and by its interaction with the MAP3K, NF-κB inducing kinase (NIK), in a yeast two-hybrid screen. IKK1 was identified as the previously cloned serine-threonine kinase, CHUK (Connelly, M. and Marcu, K. (1995) *Cell. Mol. Biol. Res.* 41, 537–549). IKK1 (also termed IKKα) is an 85 kDa, 745 amino acid protein that contains an N-terminal serine/threonine kinase catalytic domain, a leucine zipper-like amphipathic helix, and a C-terminal helix-loop-helix domain. IKK2 (also termed IKKβ)ced was also cloned by standard biochemical purification, copurifying with IKK1 from TNFα stimulated HeLa S3 cells as well as by being identified in the public database from an EST clone with sequence homology to IKK1 (Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252;

Woronicz, J. D., Gao, X., Cao, Z., Rothe, M. And Goeddel, D. V. (1997) *Science* 278, 866–869). IKK2 is an 87 kDa, 756 amino acid protein with the same over all topology as IKK1 except for the addition of an 11 amino acid extension at the C-terminus. IKK1 and IKK1 are 52% identical overall with 65% identity in the kinase domain and 44% identity in the protein interaction domains in the C-terminus. Data obtained using transient mammalian expression analysis, by in vitro translation experiments and by coexpression in a baculoviral system reveals that IKK1 and IKK2 associate preferentially as a heterodimer through their leucine zipper motifs. Although homodimers have also been described in these systems, the heterodimer is thought to be the physiologic form of the kinase in mammalian cells (Zandi, E. Rothwarf, D. M., Delhase, M., Hayadawa, M and Karin, M. (1997) *Cell* 91, 243–252; Li, J., Peet, G. W., Pullen, S. S., Schembri-King, J., Warren, T. C., Marcu, K. B., Kehry, M. R., Barton, R. and Jakes, S. (1998) *J. Biol. Chem.* 273, 30736–30741). Finally, NEMO (also termed IKKγ) contains three α-helical regions including a leucine zipper, interacts preferentially with IKK2 and is required for activation of the heterodimeric kinase complex perhaps by bringing other proteins into the signalsome complex (Yamaoka, S., Courtois, G., Bessia, C., Whiteside, S. T., Weil, R., Agou, F., Kirk, H. E., Kay, R. J., and Ireal, A. (1998) *Cell* 93, 1231–1240; Rothwarf, D. M., Zandi, E., Natoli, G., Karin, M. (1998) *Nature* 395, 297; Mercurio, F., Murray, B. W., Shevchenko, A., Bennet, B. L., Young, D. B., Li, J. W., Pascual, G., Motiwala, A., Zhu, H., Mann, M and Manning, A. M. (1999) *Mol. Cell. Biol.* 2, 1526–1538).

The kinase activities of IKK1 and IKK2 are regulated by phosphorylation and require an intact leucine zipper (LZ) for dimerization as well as an intact helix-loop-helix (HLH) domain, which can exert a positive regulatory effect on kinase activity even when it is expressed in trans with the remainder of the IKK protein (Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. and Goeddel, D. V. (1997) *Science* 278, 866–869; Dehase, M., Hayakawa, M., Chen, Y., and Karin, M. (1999) *Science* 284, 309–313). Both IKK subunits contain a canonical MAPKK activation loop motif near the N-terminus which is the target for phosphorylation and activation of kinase activity by MAP3Ks such as NIK and MEKK1, although the physiologic regulation by these two upstream kinases awaits further characterization (Zandi, E., and Karin, M. (1999) *Mol. Cell. Biol.* 19, 4547–4551; Karin, M. (1999) *J. Biol. Chem.* 274, 27339–27342; Karin, M., and Delhase, M. (1998) *Proc. Natl. Acad. Sci. USA* 95, 9067–9069). Finally, phosphorylation of serines in the C-terminus of IKK2 results in a decrease in IKK activity and it is postulated to be responsible for the transient kinase activity seen after stimulation of cells with an agonist (Dehase, M., Hayakawa, M., Chen, Y., and Karin, M. (1999) *Science* 284, 309–313).

IKK2 demonstrates a more potent kinase activity compared to IKK1 using IκBα or IκBβ as a substrate (Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. and Goeddel, D. V. (1997) *Science* 278, 866–869; Dehase, M., Hayakawa, M., Chen, Y., and Karin, M. (1999) *Science* 284, 309–313). Mutations of the phospho-acceptor serine residues within the MAPKK activation loop alters IKK2 kinase activity; the serine to alanine substitutions result in decreased kinase activity whereas the serine to glutamic acid substitutions result in a constitutively active kinase. Similar alanine mutations in IKK1 do not result in a decreased stimulation of total IKK activity in response to TNFα or ILL1β (Dehase, M., Hayakawa, M., Chen, Y., and Karin, M. (1999) *Science* 284, 309–313). IKK2 being the dominant kinase activity within the IKK complex is further supported by the analysis of fibroblasts from mice deficient in IKK1 or IKK2. Fibroblasts lacking IKK1 retain full IKK activity in response to cytokines and could activate NF-κB. In contrast, fibroblasts lacking IKK2 do not exhibit IKK activity when stimulated with cytokines nor do they activate NF-κB. Furthermore, the phenotypes of each IKK knock out is unique with IKK1 deficiency resulting in skin and skeletal defects and IKK2 knock out being embryonic lethal due to hepatocyte apoptosis (Li, Q., Antwerp, D. V., Mercurio, F., Lee, K., and Verma, I. M. (1999) *Science* 284, 321–325; Takeda, K., Tekeuchi, O., Tsujimura, T., Itami, S., Adachi, O., Kawai, T., Sanjo, H., Yoshikawa, K., Terada, N, and Akira, S. (1999) *Science* 284, 313–316; Hu, Y., Baud, V., Delhase, M., Zhang, P., Deerinck, T., Ellisman, M., Johnson, R., and Karin, M. (1999) *Science* 284, 315–320; Li, Q., Lu, Q., Hwang, J. Y., Buscher, D., Lee, K., Izpisua-Belmonte, J. C., and Verma, I. M. (1999) *Gene and Development* 13, 1322–1328; Tanaka, M., Fuentes, M. E., Yamaguchi, K., Durnin, M. H., Dalrymple, S. A., Hardy, K. L., and Goeddel, D. V. (1999) *Immunity* 10, 421–429).

It is well-known that NF-KB plays a key role in the regulated expression of a large number of pro-inflammatory mediators including cytokines such as IL-6 and IL-8, cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases. The importance of NF-κB in inflammatory disorders is further strengthened by studies of airway inflammation including asthma in which NF-κB has been shown to be activated. This activation may underlie the increased cytokine production and leukocyte infiltration characteristic of these disorders. In addition, inhaled steroids are known to reduce airway hyper responsiveness and suppress the inflammatory response in asthmatic airways. In light of the recent findings with regard to glucocorticoid inhibition of NF-κB, one may speculate that these effects are mediated through an inhibition of NF-κB. Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α. Such a distribution may be the underlying mechanism for the increased cytokine and eicosanoid production characteristic of this tissue. See Roshak, A. K., et al., J. Biol. Chem., 271, 31496–31501 (1996).

The NF-κB/Rel and IκB proteins are also likely to play a key role in neoplastic transformation. Family members are associated with cell transformation in vitro and in vivo because of overexpression, gene amplification, gene rearrangements, or translocations (Gilmore T D, *Trends Genet* 7:318–322, 1991; Gillmore T D, *Oncogene* 18:6925–6937, 1999; Rayet B. et al., *Oncogene* 18: 6938–6947, 1991). In addition, rearrangement and/or amplification of the genes encoding these proteins are seen in 20–25% of certain human lymphoid tumors. In addition, a role for NF-κB in the regulation of apoptosis, cell cycle progression, invasion, and metastasis has been reported (Bours V. et al., *Biochemical Pharmacology* 60:1085–1090, 2000) strengthening the role of this transcription factor in the control of cell proliferation. The inhibition of NF-κB has been shown to potentiate TNF- and cancer therapy through increased apoptosis (Wang C-Y et al., *Science* 274:784–787, 1996; Wang C-Y et al., *Nat Med* 5:412–417, 1999). It has also been shown that human T-cell leukemia virus type 1 (HTLV1) infected cells (the etiological agent of an aggressive malignancy of activated CD4+ T lymphocytes), IKKα and IKKβ are expressed constitutively, which normally function in a transient manner (Chu Z-L et al., *J of Biological Chemistry* 273:15891–15894, 1998). The HTLV1 transforming and transactivating protein (Tax) has been shown to bind MEKK1 and increases the activity of IKKβ to enhance phosphorylation of serine residues in IκBα that lead to its degradation.

U.S. Pat. No. 3,940,418 to R. Hamilton describes tricyclic 4,5-dihydrobenz[g]indazole-3-carboxylic acids as antiinflammatory agents.

U.S. Pat. No. 4,803,193 to Kanda et al, describes spiro [3-alkyl-1-aryl[1]benzopyrano[4,3-c]pyrazole-4(1H),9'-[9H]fluorenes as heat sensitive recording materials.

V. Colota et al (*J. Med. Chem.*, 33, 2646 (1991)) describe tricyclic heteroaramatic systems, including 1-aryl-pyrazolo [4,5-c]quinolin-4-ones, 1-aryl-pyrazolo[4,5-c][1,8] naphthyridin-4-ones, and 1-aryl-[1]benzopyrano[3,4-d] pyrazol-4-ones for CNS applications. F. Melani et al [*J. Med. Chem.*, 29, 291 (1986) also describe 1-phenyl-pyrazolo [4,5-c]quinolines for CNS applications.

U.S. Pat. Nos. 4,816,467 and 5,206,258 to Doria et al describe (2-cyano-3-(1,4-dihydro)-1-phenyl-[1] benzothiopyrano [4,3-c]pyrazol-3-yl)-3-oxo-propanamides as immunomodulators. G. Doria et al (*Farmaco*, 46, 843 (1991)) also describe the immunomodulating activity of pyrazolylpropanamides, and specifically ethyl[1-(4-fluorophenyl)-1,4-dihydro-[1]benzothiopyrano[4,3-c] pyrazole]-3-carboxylate. British patent 2,227,741 describes related benzopyrano[4,3-c]pyrazoles and benzothiopyrano [4,3-c]pyrazoles. European application No. 347,773 similarly describes such fused pyrazole compounds, and specifically α-cyano-N,1-bis(4-fluorophenyl)-β-oxo-1H-[1] benzothieno[3,2-c]pyrazole-3-propanamide. U.S. Pat. No. 5,260,328 to Doria et al describes 2-cyano-3-(1,4-dihydro)-1-phenyl-[1]benzothiopyrano[4,3-c]pyrazol-3-yl)-3-oxopropanamides for the treatment of rheumatoid arthritis.

U.S. Pat. No. 4,678,499 to Pasteris et al describes 1-aryl-indenopyrazol-4-one-5-sulfonamides as having herbicidal activity. Specifically, 1-phenyl-indenopyrazol-4-one-5-sulfonamide and 1,4-dihydro-N-[[(4-methoxy-6-methyl-2-pyrimidinyl)amino]carbonyl]-3-methyl-1-[4-(methylsulfonyl)phenyl]-4-oxo-indeno[1,2-c]pyrazole-5-sulfonamide are described.

U.S. Pat. Nos. 5,547,975; 5,565,482; 5,670,532; and 5,886,016 to Talley et al. describe benzopyranopyrazolyl derivates for the treatment of inflammation. Fravolini, A. et al., describes substituted pyrazolyl compounds having anti-inflammatory activity (*Farmco, Ed. Sci* 33:855–856, 1978).

DETAILED DESCRIPTION OF THE INVENTION

A class of compounds, which are useful in treating cancer, inflammation, and inflammation related disorders, is defined by Formula I:

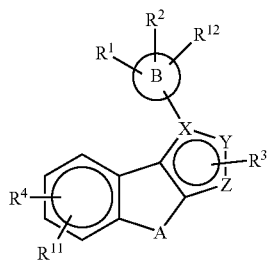

wherein

A is $(CH_2)_m$-Q-$(CH_2)_n$, wherein each $CH_2$ may be independently substituted with one or more substitution selected from the group consisting of: hydroxy, halo, alkoxy, lower alkyl, amino, aminoalkyl, alkylamino, alkenyl, and alkynyl;

Q is selected from the group consisting of: $S(O)_p$, O, $CR^{15}$=N, N=$CR^{15}$, —CO—O—, —CO—NH—, —CO—N(alkyl)-, and $NR^5$;

m is 0 to 3, inclusive;

n is 0 to 3, inclusive;

p is 0 to 2, inclusive;

B is a 5 or 6 membered heteroaryl, or aryl, optionally saturated, or optionally substituted with $R^1$, $R^2$, or $R^{12}$;

X is selected from the group consisting of: N and C;

Y and Z are independently selected from the group consisting of: N, C, CH, $CR^3$, S, and O;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)$ $R^7$, $COR^6$, $SR^6$, $SOR^6$, $SO_2R^6$, $NR^6$ $R^7$, $NR^6COR^7$, $NR^6CONHR^7$, $NR^6SO_2R^7$, $NR^6SO_2NHR^7$, and $SO_2N$ $(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)$ $R^7$, $COR^6$, $SR^6$, $SOR^6$, $SO_2R^6$, $NR^6R^7$, $NR^6$ $COR^7$, $NR^6CONHR^7$, $NR^6SO_2R^7$, $NR^6SO_2NHR^7$, and $SO_2N$ $(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is selected from the group consisting of: halogen, hydrido, hydroxyalkyl, alkyl, $OR^6$, CN, $NO_2$, $SR^6$, $NHR^6$, $CON(R^6)R^7$, $NHCONHR^6$, $CO_2H$, and haloalkyl;

$R^1$ and $R^2$ may be taken together to form a 5 to 7 membered saturated or unsaturated carbocyclic ring optionally containing 0 to 3 heteroatoms selected from the group consisting of: N, O, or S, and wherein said ring is optionally substituted with $R^1$;

$R^3$ is selected from the group consisting of: substituted or unsubstituted amidine, alkylamino, aminoalkyl, $CONHR^{16}$, $NH_2$, $NHCOR^6$, and $CH_2NHCOR^6$;

R⁴ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR¹³, SR⁸, SO₂N(R⁸)R⁸', NHR⁹, NHCOR⁹, NR⁹COR⁹, NHCO(OR⁹), NR⁹CO(OR⁹), NR⁸SO₂R¹⁰, NHSO₂N(R¹⁰)R¹⁰', NR⁶CON(R¹⁰)R¹⁰', COR⁹, CO₂R⁸, CON(R⁸)R⁸', wherein R⁸ and R⁸' may be taken together to form a 3–7 membered carbocyclic ring having 1 to 3 substituted or unsubstituted heteroatoms selected from S, SO, SO₂, O, N, and NR⁶, and wherein R¹⁰ and R¹⁰' may be taken together to form a 3–7 membered carbocyclic ring having 1 to 3 substituted or unsubstituted heteroatoms selected from S, SO, SO₂, O, N, and NR⁶ wherein said aryl, heterocyclic, heteroaryl, or alkenyl are optionally substituted with R⁹;

R⁵ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: OR¹⁴, N(R¹⁴)R¹⁴', and glycols;

R⁶ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R⁷ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R⁸ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R⁸' is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R⁹ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

R¹⁰ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R¹⁰' is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R¹¹ is selected from the group consisting of: hydrido, halogen, haloalkyl, CN, CO₂R⁵, lower alkyl, lower alkenyl, lower alkynyl, alkoxy, and CONH₂;

R¹² is selected from the group consisting of: hydrido, halogen, alkyl, and alkoxy;

R¹³ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: OR¹⁴, N(R¹⁴)R¹⁴', and glycols;

R¹⁴ is independently selected from the group consisting of: hydrido, and lower alkyl;

R¹⁴' is independently selected from the group consisting of: hydrido, and lower alkyl;

R¹⁵ is selected from the group consisting of: hydrido, halogen, alkyl, cycloalkyl, aryl, haloalkyl, heteroaryl, heterocyclic, alkylalkene, alkylalkyne, hydroxy, hydroxyalkyl, alkylhydroxy, amino, aminoalkyl, alkylamino, alkylaminoalkyl, alkylhydroxyalkyl, nitro, cyano, alkylthio, alkylsulfinyl, alkylsulfonyl; wherein aryl or arylalkyl are optionally substituted with one or more radical selected from alkyl, alkoxy, halo, haloalkyl, cyano, haloalkoxy, acyl, carboxyl, hydroxy, hydroxyalkyloxy, phenoxy, benzyloxy, dialkylaminoalkyloxy, heterocyclic; and R¹⁶ is independently selected from the group consisting of: hydrido, aryl, lower alkyl, haloalkyl, alkenyl, alkynyl, hydroxyalkyl, aminoalkyl, alkoxy, and alkoxyalkyl;

or isomers, tautomers, carriers, esters, prodrugs, pharmaceutically acceptable salts thereof.

Another class of compounds is defined by formula II:

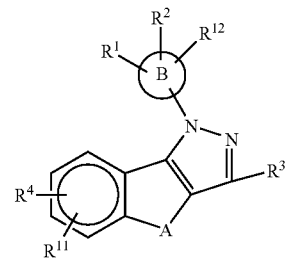

wherein

A is (CH₂)ₘ-Q-(CH₂)ₙ, wherein each CH₂ may be independently substituted with one or more substitution selected from the group consisting of: hydroxy, halo, alkoxy, lower alkyl, amino, aminoalkyl, alkylamino, alkenyl, and alkynyl;

Q is selected from the group consisting of: $S(O)_p$, O, $CR^{15}$=N, N=$CR^{15}$, —CO—O—, —CO—NH—, —CO—N(alkyl)-, and $NR^5$;

m is 0 to 3, inclusive;

n is 0 to 3, inclusive;

p is 0 to 2, inclusive;

B is a 5 or 6 membered heteroaryl, or aryl, optionally saturated, or optionally substituted with $R^1$, $R^2$, or $R^{12}$;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is selected from the group consisting of: halogen, hydrido, hydroxyalkyl, alkyl, $OR^6$, CN, $NO_2$, $SR^6$, $NHR^6$, $CON(R^6)R^7$, $NHCONHR^6$, $CO_2H$, and haloalkyl;

$R^1$ and $R^2$ may be taken together to form a 5 to 7 membered saturated or unsaturated carbocyclic ring optionally containing 0 to 3 heteroatoms selected from the group consisting of: N, O, or S, and wherein said ring is optionally substituted with $R^1$;

$R^3$ is selected from the group consisting of: substituted or unsubstituted amidine, alkylamino, aminoalkyl, $CONHR^{16}$, $NH_2$, $NHCOR^6$, and $CH_2NHCOR^6$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is selected from the group consisting of: hydrido, halogen, alkyl, and alkoxy;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^{14}$ is independently selected from the group consisting of: hydrido, and lower alkyl;

$R^{14'}$ is independently selected from the group consisting of: hydrido, and lower alkyl;

$R^{15}$ is selected from the group consisting of: hydrido, halogen, alkyl, cycloalkyl, aryl, haloalkyl, heteroaryl, heterocyclic, alkylalkene, alkylalkyne, hydroxy, hydroxyalkyl, alkylhydroxy, amino, aminoalkyl, alkylamino, alkylaminoalkyl, alkylhydroxyalkyl, nitro, cyano, alkylthio, alkylsulfinyl, alkylsulfonyl; wherein aryl or arylalkyl are optionally substituted with one or more radical selected from alkyl, alkoxy, halo, haloalkyl, cyano, haloalkoxy, acyl, carboxyl, hydroxy, hydroxyalkyloxy, phenoxy, benzyloxy, dialkylaminoalkyloxy, heterocyclic; and $R^{16}$ is independently selected from the group consisting of: hydrido, aryl, lower alkyl, haloalkyl, alkenyl, alkynyl, hydroxyalkyl, aminoalkyl, alkoxy, and alkoxyalkyl;

or isomers, tautomers, carriers, esters, prodrugs, pharmaceutically acceptable salts thereof.

Definitions

The present invention includes the use of all hydrates, solvates, complexes and prodrugs of the compounds of this invention. Prodrugs are any covalently bonded compounds, which release the active parent drug according to Formula I in vivo. If a chiral center or another form of an isomeric center is present in a compound of the present invention all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or any sub-formula thereof is independent of its meaning, or any other substituents meaning, at any other occurrence, unless specified otherwise.

The present invention includes the use of all hydrates, solvates, complexes and prodrugs of the compounds of this invention. Prodrugs are any covalently bonded compounds, which releases the active parent drug according to Formula I or Formula II in vivo. If a chiral center or another form of an isomeric center is present in a compound of the present invention all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or Formula II or any sub-formula thereof is independent of its meaning, or any other substituents meaning, at any other occurrence, unless specified otherwise.

The term "alkyl" is used, either alone or within other terms such as "haloalkyl" and "alkylsulfonyl"; it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. Examples of such radicals include methyl, ethyl, n-propyl, isopropyl, n-butyl, isobutyl, sec-butyl, tert-butyl, pentyl, isoamyl, hexyl, octyl and the, like. The term "hydrido" denotes a single hydrogen atom (H). This hydrido radical may be attached, for example, to an oxygen atom to form a hydroxyl radical or two hydrido radicals may be attached to a carbon atom to form a methylene ($—CH_2—$) radical. The term "halo" means halogens such as fluorine, chlorine, and bromine or iodine atoms. The term "haloalkyl" embraces radicals wherein any one or more of the alkyl carbon atoms is substituted with halo as defined above. Specifically embraced are monohaloalkyl, dihaloalkyl, and polyhaloalkyl radicals. A monohaloalkyl radical, for one example, may have a bromo, chloro, or a fluoro atom within the radical. Dihalo radicals may have two or more of the same halo atoms or a combination of different halo radicals and polyhaloalkyl radicals may have more than two of the same halo atoms or a combination of different halo radicals. The term "hydroxyalkyl" embraces linear or branched alkyl radicals having one to about ten carbon atoms any one of which may be substituted with one or more hydroxyl radicals. The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro, or bromo, to provide "haloalkoxy" or "haloalkoxyalkyl" radicals. Examples of "alkoxy" radicals include methoxy, butoxy, and trifluoromethoxy. The term "aryl", alone or in combination, means a carbocyclic aromatic system containing one, two, or three rings wherein such rings may be attached together in a pendent manner or may be fused. The term "aryl" embraces aromatic radicals such as phenyl, naphthyl, tetrahydronapthyl, indane, and biphenyl. The term "heterocyclic" embraces saturated, partially saturated, and unsaturated heteroatom-containing ring-shaped radicals, where the heteroatoms may be selected from nitrogen, sulfur and oxygen. Examples of saturated heterocyclic radicals include pyrrolidyl and morpholinyl. The term "heteroaryl" embraces unsaturated heterocyclic radicals. Examples of unsaturated heterocyclic radicals, also termned "heteroaryl" radicals include thienyl, pyrrolyl, furyl, pyridyl, pyrimidyl, pyrazinyl, pyrazolyl, oxazolyl, isoxazolyl, imidazolyl, thiazolyl, and tetrazolyl. The term also embraces radicals where heterocyclic radicals are fused with aryl radicals. Examples of such fused bicyclic radicals include benzofuran, benzothiophene, and the like. The term "heterocyclic alkyl" embraces alkyl attached to the heterocyclic. The term "sulfonyl", whether used alone or linked to other terms such as alkylsulfonyl, denotes respectively divalent radicals $—SO_2—$. "Alkylsulfonyl", embraces alkyl radicals attached to a sulfonyl radical, where alkyl is defined as above. The term "arylsulfonyl" embraces sulfonyl radicals substituted with an aryl radical. The terms "sulfamyl" or "sulfonamidyl", whether alone or used with terms such as "N-alkylsulfamyl", "N-arylsulfamyl", "N,N-dialkylsulfamyl" and "N-alkyl-N-arylsulfamyl", denotes a sulfonyl radical substituted with an amine radical, forming a sulfonamide (—SO$_2$—NH$_2$). The terms "N-alkylsulfamyl" and "N,N-dialkylsulfamyl" denote sulfamyl radicals substituted, respectively, with one alkyl radical, a cycloalkyl ring, or two alkyl radicals. The terms "N-arylsulfamyl" and "N-alkyl-N-arylsulfamyl" denote sulfamyl radicals substituted, respectively, with one aryl radical, and one alkyl and one aryl radical. The terms "carboxy" or "carboxyl", whether used alone or with other terms, such as "carboxyalkyl", denotes —CO$_2$H. The term "carboxyalkyl" embraces radicals having a carboxyradical as defined above, attached to an alkyl radical. The term "carbonyl", whether used alone or with other terms, such as "alkylcarbonyl", denotes —(C=O)—. The term "alkylcarbonyl" embraces radicals having a carbonyl radical substituted with an alkyl radical. An example of an "alkylcarbonyl" radical is CH$_3$—(C=O)—. The term "alkylcarbonylalkyl" denotes an alkyl radical substituted with an "alkylcarbonyl" radical. The term "alkoxycarbonyl" means a radical containing an alkoxy radical, as defined above, attached via an oxygen atom to a carbonyl (C=O) radical. Examples of such "alkoxycarbonyl" radicals include (CH$_3$)$_3$CO—C=O)— and —(O=)C—OCH$_3$. The term "alkoxycarbonylalkyl" embraces radicals having "alkoxycarbonyl", as defined above substituted to an alkyl radical. Examples of such "alkoxycarbonylalkyl" radicals include (CH$_3$)$_3$COC(=O) (CH$_2$)$_2$— and —(CH$_2$)$_2$(O=)COCH$_3$. The term "amido" when used by itself or with other terms such as "amidoalkyl", "N-monoalkylamido", "N-monoarylamido", "N,N-dialkylamido", "N-alkyl-N-arylamido", "N-alkyl-N-hydroxyamido" and "N-alkyl-N-hydroxyamidoalkyl", embraces a carbonyl radical substituted with an amino radical. The terms "N-alkylamido" and "N,N-dialkylamido" denote amido groups which have been substituted with one alkyl radical and with two alkyl radicals, respectively. The terms "N-monoarylamido" and "N-alkyl-N-arylamido" denote amido radicals substituted, respectively, with one aryl radical, and one alkyl and one aryl radical. The term "N-alkyl-N-hydroxyamido" embraces amido radicals substituted with a hydroxyl radical and with an alkyl radical. The term "N-alkyl-N-hydroxyamidoalkyl" embraces alkyl radicals substituted with an N-alkyl-N-hydroxyamido radical. The term "amidoalkyl" embraces alkyl radicals substituted with amido radicals. The term "aminoalkyl" embraces alkyl radicals substituted with amino radicals. The term "alkylaminoalkyl" embraces aminoalkyl radicals having the nitrogen atom substituted with an alkyl radical. The term "amidino" denotes an —C(=NH)—NH$_2$ radical. The term "cyanoamidino" denotes an —C(=N—CN)—NH$_2$ radical. The term "heterocycloalkyl" embraces heterocyclic-substituted alkyl radicals such as pyridylmethyl and thienylmethyl. The term "aralkyl" embraces aryl-substituted alkyl radicals such as benzyl, diphenylmethyl, triphenylmethyl, phenethyl, and diphenethyl. The terms benzyl and phenylmethyl are interchangeable. The term "cycloalkyl" embraces radicals having three to ten carbon atoms, such as cyclopropyl cyclobutyl, cyclopentyl, cyclohexyl, and cycloheptyl. The term "cycloalkenyl" embraces unsaturated radicals having three to ten carbon atoms, such as cylopropenyl, cyclobutenyl, cyclopentenyl, cyclohexenyl, and cycloheptenyl. The term "alkylthio" embraces radicals containing a linear or branched alkyl radical, of one to ten carbon atoms, attached to a divalent sulfur atom. An example of "alkylthio" is methylthio, (CH$_3$—S—). The term "alkylsulfinyl" embraces radicals containing a linear or branched alkyl radical, of one to ten carbon atoms, attached to a divalent —S(=O)— atom. The terms "N-alkylamino" and "N,N-dialkylamino" denote amino groups which have been substituted with one alkyl radical and with two alkyl radicals, respectively. The term "acyl", whether used alone, or within a term such as "acylamino", denotes a radical provided by the residue after removal of hydroxyl from an organic acid. The term "acylamino" embraces an amino radical substituted with an acyl group. An examples of an "acylamino" radical is acetylamino (CH$_3$C(=O)—NH—).

Another aspect of the present invention is chemical intermediates in the synthesis of the claimed compounds.

Another aspect of the present invention is methods of syntheses of the claimed compounds.

Compounds of Formula I or Formula II would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I or Formula II would be useful to treat arthritis, including but not limited to rheumatoid arthritis, spondylo arthopathies, gouty arthritis, osteoarthritis, systemic lupus erythematosus, and juvenile arthritis. Such compounds of Formula I or Formula II would be useful in the treatment of asthma, bronchitis, menstrual cramps, tendinitis, bursitis, and skin related conditions such as psoriasis, eczema, burns, and dermatitis. Compounds of Formula I or Formula II also would be useful to treat gastrointestinal conditions such as inflammatory bowel disease, Crohn's disease, gastritis, irritable bowel syndrome, and ulcerative colitis and for the prevention of colorectal cancer. Compounds of Formula I or Formula II would be useful in treating inflammation in such diseases as vascular diseases such as vascularitus, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds of the present invention may also be used for pain. The compounds are useful as antiinflammatory agents, such as for the treatment of arthritis, with the additional benefit of having significantly less harmful side effects. The compounds of formula I or II are useful as agents for treating cancer or anticancer agents. The compounds of formula I or II may be proapoptotic, antiapoptotic, anticell cycle progressive, antiinvasive, antiproliferative, antiangiogenic, and antimetastatic. The cancer may be colon, ovarian, breast, prostate, gastric, B-cell lymphoma, and multiple myeloma. More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma. Due to the key role of protein kinases in the regulation of cellular proliferation, these compounds are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. The compounds of formula I or II may be used as an anitviral agent. The compounds of this invention are useful as inhibitors of protein kinases. The compounds of this invention are useful as inhibitors of IKK1 and/or IKK2, IKKα/IKKβ heterodimer, TBK or IKKi. The compounds of the invention may also useful as inhibitors of other protein kinases such as, for instance, protein kinase C in different isoforms, cyclin dependent kinase (cdk), Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, wee1 kinase, Src, Abl, Akt, ILK, MK-2, IKK-2, Cdc7, Nek, and thus be effective in the treatment of diseases associated with other protein kinases. The present invention preferably includes compounds, which selectively inhibit IKK2 over IKK1. Preferably, the compounds have an IKK2 IC50 of less than 1 µM, and have a selectivity ratio of IKK2 inhibition over IKK1 inhibition of at least 50, and more preferably of at least 100. Even more preferably, the compounds have an IKK1 IC50 of greater than 10 µM, and more preferably of greater than 100 µM. The compounds of formula may also be used to treat angiogenesis associated cardiovascular, ophthalmology and osteoporosis disorders. The compounds of the present invention may also be used for treatment of knee injury such as sport injuries.

While it is possible for an active ingredient to be administered alone as the raw chemical, it is preferable to present it as a pharmaceutical formulation. The present invention comprises a pharmaceutical composition comprising a therapeutically effective amount of a compound of the present invention in association with at least one pharmaceutically acceptable carrier, adjuvant, or diluent. The present invention also comprises a method of treating inflammation or inflammation associated disorders in a subject, the method comprising administering to the subject having such inflammation or disorders a therapeutically effective amount of a compound of the present invention. Also included in the family of compounds of the present invention are the pharmaceutically acceptable salts thereof. The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, phydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, O-hydroxybutyric, salicyclic, galactaric and galacturonic acid. Suitable pharmaceutically acceptable base addition salts of compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of the present invention by reacting, for example, the appropriate acid or base with the compound of the present invention.

Also embraced within this invention are pharmaceutical compositions comprising one or more compounds of the present invention in association with one or more non-toxic, pharmaceutically acceptable carriers and/or diluents and/or adjuvants and/or excipient (collectively referred to herein as "carrier" materials) and, if desired, other active ingredients. Accordingly, the compounds of the present invention may be used in the manufacture of a medicament. Pharmaceutical compositions of the compounds of the present invention prepared as herein before described may be formulated as solutions or lyophilized powders for parenteral administration. Powders may be reconstituted by addition of a suitable diluent or other pharmaceutically acceptable carrier prior to use. The liquid formulation may be a buffered, isotonic aqueous solution. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, intravenously, subcutaneously, intramuscularly, intramedullary, orally, or topically. For oral administration, the pharmaceutical composition may be in the form of, for example, a tablet, capsule, suspension, or liquid. The active ingredient may also be administered by injection as a composition wherein, for example, normal isotonic saline solution, standard 5% dextrose in water or buffered sodium or ammonium acetate solution may be used as a suitable carrier. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, or sodium citrate. The pharmaceutical composition is preferably made in the form of a dosage unit containing a particular amount of the active ingredient. Examples of such dosage units are tablets or capsules. The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg bodyweight, preferably between about 0.1 and about 50 mg/kg body weight and most preferably between about 1 to 20 mg/kg bodyweight, may be appropriate. The daily dose can be administered in one to four doses per day. For therapeutic purposes, the compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled release formulation as may be provided in a dispersion of active compound in a sustained release material such as glyceryl monostearate, glyceryl distearate, hydroxypropylmethyl cellulose alone or with a wax. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion, or an aqueous or non-aqueous suspension. Such a liquid formulation may be administered orally or filled into a soft gelatin capsule. For rectal administration, the compounds of the present invention may also be combined with excipients such as cocoa butter, glycerin, gelatin, or polyethylene glycols and molded into a suppository. The methods of the present invention include topical administration of the compounds of the present invention. By topical administration is meant non-systemic administration, including the application of a compound of the invention externally to the epidermis, to the buccal cavity and instillation of such a compound into the ear, eye, and nose, wherein the compound does not significantly enter the blood stream. By systemic administration is meant oral, intravenous, intraperitoneal, and intramuscular administration. The amount of a compound of the present invention (hereinafter referred to as the active ingredient) required for therapeutic or prophylactic effect upon topical administration will, of course, vary with the compound chosen, the nature and severity of the condition being treated and the animal undergoing treatment, and is ultimately at the discretion of the physician.

The topical formulations of the present invention, both for veterinary and for human medical use, comprise an active ingredient together with one or more acceptable carriers therefore, and optionally any other therapeutic ingredients. The carrier must be "acceptable" in the sense of being compatible with the other ingredients of the formulation and not deleterious to the recipient thereof. Formulations suitable for topical administration include liquid or semi-liquid preparations suitable for penetration through the skin to the site of where treatment is required such as: liniments, lotions, creams, ointments or pastes, and drops suitable for administration to the eye, ear or nose. The active ingredient may comprise, for topical administration, from 0.01 to 5.0 wt %. of the formulation.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container, which is then sealed and sterilized by autoclaving, or maintaining at 90–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.00217 c), benzalkonium chloride (0.01%) and chlorhexidine acetate (0.01%). Suitable solvents for the preparation of an oily solution include glycerol, diluted alcohol, and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil. Creams, ointments, or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface-active agent such as an anionic, cationic, or non-ionic surface-active agent such as sorbitan esters or polyoxyethylene derivatives thereof. Suspending agents such as natural gums, cellulose derivatives or inorganic materials such as silicaceous silicas, and other ingredients such as lanolin may also be included. Other adjuvants and modes of administration are well and widely known in the pharmaceutical art. Although this invention has been described with respect to specific embodiments, the details of these embodiments are not to be construed as limitations.

General Synthetic Procedures

The starting materials used herein are commercially available or are prepared by routine methods well known to those of ordinary skill in the art and can be found in standard reference books, such as the COMPENDIUM OF ORGANIC SYNTHETIC METHODS, Vol. I–VI (published by Wiley-Interscience).

The compounds of the invention can be synthesized according to the following procedures of Schemes I–X, wherein the R1–R16 substituents, linker A, are as defined for Formula I, above, except where further noted.

SCHEME I

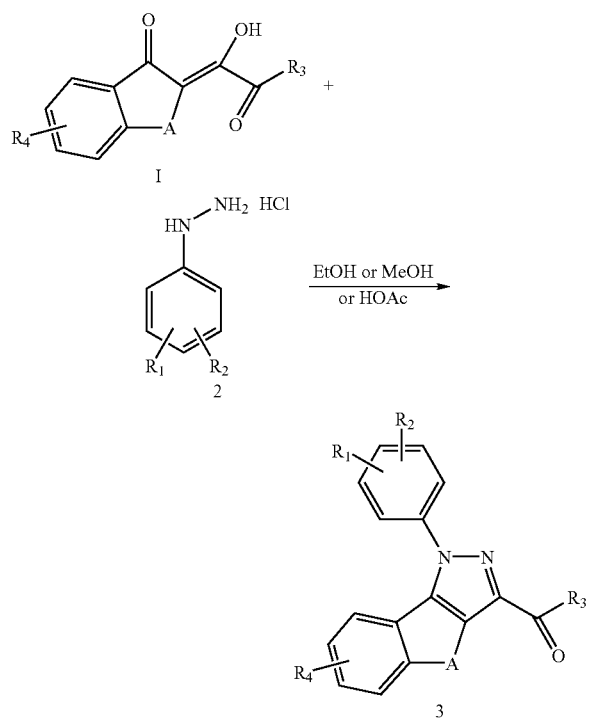

Synthetic Scheme I illustrates the procedure used to prepare the anti-inflammatory pyrazoles of the present invention. 1,3-Dicarbonyl compounds such as 1, or the shown enol form which is in equilibrium with the 1,3-diketone, are allowed to react with a substituted hydrazine hydrochloride 2 in warm methanol or ethanol or acetic acid to provide the pyrazoles 3 via a condensation reaction. When A=—$CH_2CH_2$—, the central ring may be aromatized to provide A=—CH=CH—, by using an oxidant such as DDQ, Pd or Pt on carbon with cyclooctadiene or other $H_2$ acceptor, or sulfur in an appropriate solvent.

SCHEME II

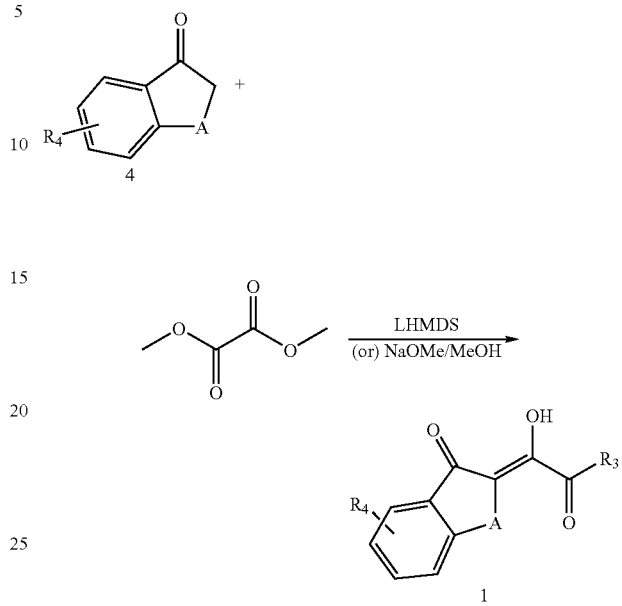

Synthetic Scheme II illustrates the procedure for the preparation of substituted diketones 1. An appropriately substituted ketone 4, including, but not limited to; 1-indanones, 1-tetralones, and 1-benzosuberones, is first treated with base, such as sodium methoxide, lithium bist-rimethylsilylamide or lithium diisopropylamide (LDA), followed by condensation with a suitable acylating agent, such as, dimethyl or diethyl oxalate, in an appropriate solvent, such as methanol, diethyl ether or tetrahydrofuran, to provide 1,3-dicarbonyl compounds 1 which are suitable for conversion into anti-inflammatory pyrazoles as illustrated in Scheme I. Alternatively, the dicarbonyl compounds 1 can be directly prepared from commercially available cyclic ketones 4.

SCHEME III

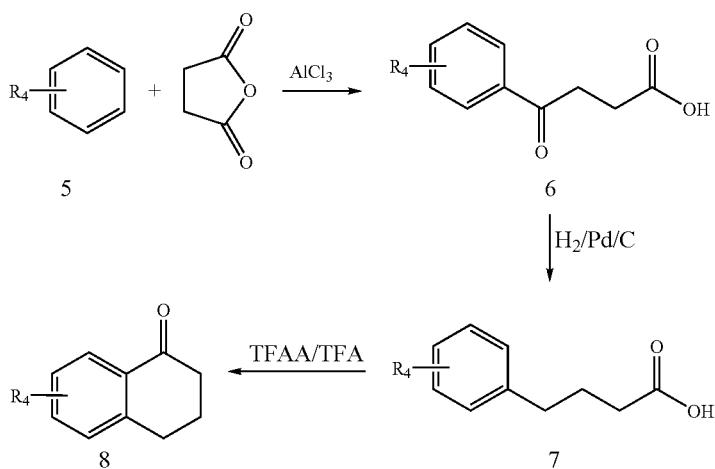

Synthetic Scheme III illustrates a three-step procedure used for the preparation of substituted 1-tetralones. In step one, an appropriate substituted benzene 5 is condensed with succinic anhydride and a catalyst such as aluminum chloride into the corresponding 4-phenyl-4-ketobutanoic acid derivatives 6. In step two, the keto group of the 4-phenyl-4-ketobutanoic acids 6 is reduced using catalytic hydrogenation or Wolff-Kishner type reductions, thus providing 4-phenylbutanoic acids 7. In addition, ketone reductions can be carried out using metal amalgams. In step three, the 4-phenylbutanoic acids are treated with a mixture of trifluoroacetic anhydride, and trifluoroacetic acid to effect intramolecular Friedel-Crafts acylation affording selected tetralones 8. Alternatively, the Friedel-Crafts acylation can be affected with other strong acids such as polyphosphoric acid, sulfuric acid, or aluminum chloride.

SCHEME IV

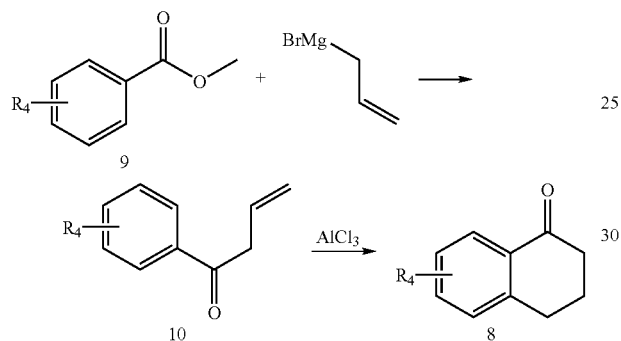

Synthetic Scheme IV describes an alternate synthetic route to 1-tetralones 8. In step one, addition of allylmagnesium bromide in a suitable solvent such as, THF or diethyl ether, to an appropriately substituted benzoate 9 affords the 1-phenylbut-3-ene-1-ones 10. In step two, the 1-phenylbut-3-ene-1-ones 10 can be cyclized under Friedel-Crafts alkylation conditions, provided R4 is a ring activating substituent, using catalysts such as aluminum chloride to produce 1-tetralones 8.

SCHEME V

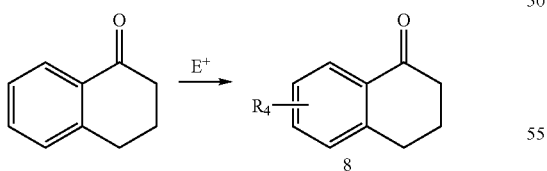

Scheme V describes the direct modification of 1-tetralone to substituted tetralones. Commercially available 1-tetralone may be treated with a variety of electrophilic reagents such as bromine, ammonium nitrite or vinylsilanes, represented by $E^+$, with or without a catalyst to generate directly a substituted tetralone 8, containing bromo, nitro or vinyl groups. Such tetralones 8 can be further embellished to provide the desired substitution patterns. Mixtures may be readily separated using chromatographic techniques.

SCHEME VI

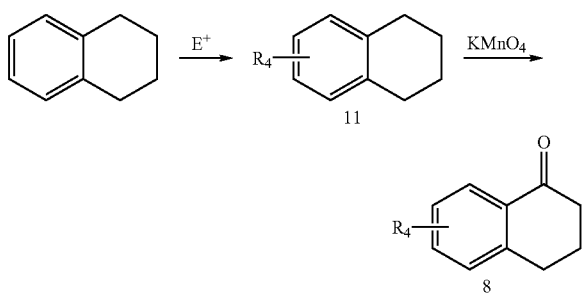

An alternate to Scheme V is Scheme VI wherein an appropriately substituted decaline is subjected to electrophilic addition to generate substituted decalins 11. Substituted decalins may also be prepared by Friedel-Crafts alkylation of substituted benzenes. Substituted decalins 11 can then be oxidized to the tetralones 8 using oxidants such as $KMnO_4$ or $SeO_2$.

SCHEME VII

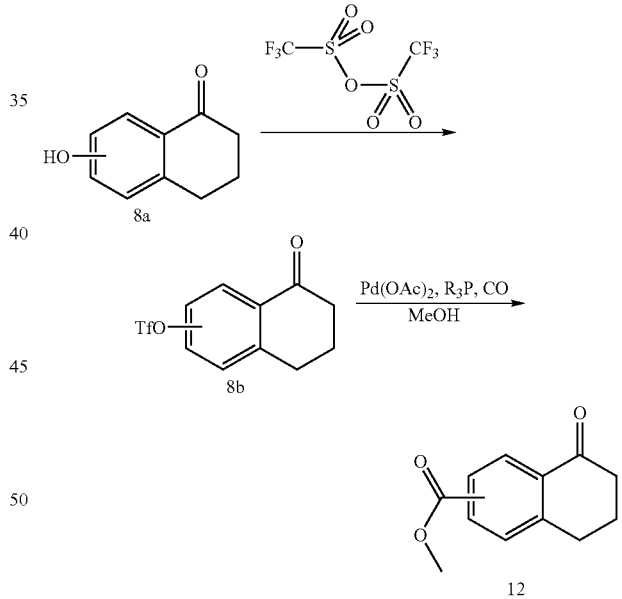

Scheme VII describes the modification of existing tetralones into analogs containing differing functional groups that can also be further modified. By example, hydroxy tetralone (8a where $R_4$=OH) can be converted to the triflate 8b by treatment with trifluoromethane sulfonic anhydride. Triflate 8b can the be subjected to Pd(OAc)$_2$ an appropriate phosphine and CO in the presence of methanol to generate tetralone 12 containing a carboxy methyl group. Triflates can be used in a variety of palladium coupling reactions to introduce additional functional groups.

SCHEME VIII

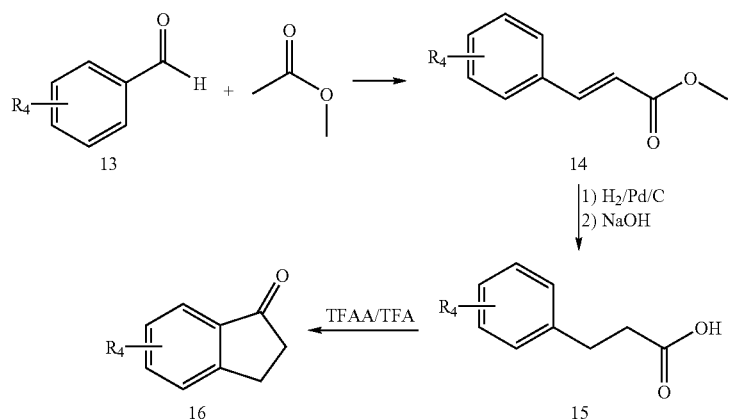

Synthetic Scheme VIII illustrates a three step procedure used for the preparation of substituted 1-indanones 16. In step one, an appropriate substituted benzaldehyde 13 is condensed with methyl acetate and a catalyst such as triethylamine into the corresponding methyl cinnamate derivatives 14. Additionally, commercially available cinnamates may be used in the following steps. In step two the olefin group of the cinnamate 14 is reduced using catalytic hydrogenation and the ester hydrolyzed with base, such as NaOH, thus providing 3-phenylpropanoic acids 15. In step three, the 3-phenylpropanoic acids are treated with a mixture of trifluoroacetic anhydride and trifluoroacetic acid to effect intramolecular Friedel-Crafts acylation affording selected 1-indanones 16. Alternatively, the Friedel-Crafts acylation can be effected with other strong acids such as sulfuric acid or aluminum chloride.

SCHEME IX

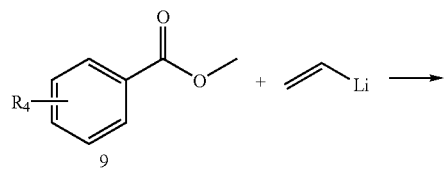

Synthetic Scheme IX illustrates a two-step route for the preparation of substituted 1-indanones 16. Commercially available methyl benzoates 9, or other alkyl esters, may be treated with a vinyl lithium reagent to afford phenylvinyl ketones 17. Alternatively, dimethylamides or N-methyl-O-methylhydroxamides may be used in place of the esters. Also, other vinyl metals, such as; vinylmagnesium bromide may be used in place of the vinyl lithium reagent. The resulting phenylvinyl ketones may be cyclized using Friedel-Crafts alkylating catalysts, such as aluminum chloride.

SCHEME X

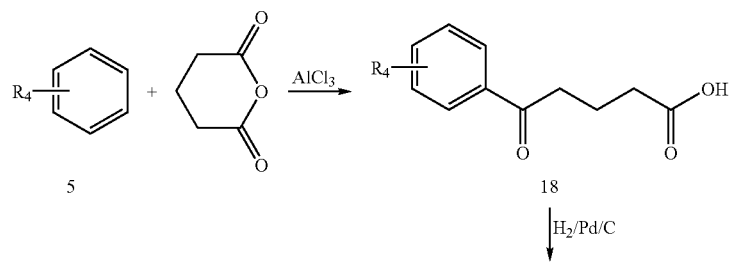

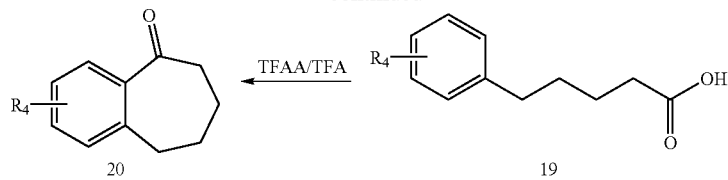

Synthetic Scheme X illustrates a three step procedure used for the preparation of substituted 1-benzosuberones 20. In step one, an appropriate substituted benzene 5 is condensed with glutaric anhydride and a catalyst such as aluminum chloride into the corresponding 5-phenyl-5-ketopentanoic acid derivatives 18. In step two, the keto group of the 5-phenyl-5-ketopentanoic acids 18 is reduced using catalytic hydrogenation or Wolff-Kishner type reductions, thus providing 5-phenylpentanoic acids 19. In addition, ketone reductions can also be carried out using metal amalgams. In step three, the 5-phenylpentanoic acids are treated with a mixture of trifluoroacetic anhydride, and trifluoroacetic acid to effect intramolecular Friedel-Crafts acylation affording selected benzosuberones 20. Alternatively, the Friedel-Crafts acylation can be affected with other strong acids such as polyphosphoric acid, $H_2SO_4$ or $AlCl_3$. Alternatively, 5-phenyl-5-ketopentanoic acids 18, can be prepared from glutaric acid and a phenyllithium or a phenyl Grignard reagent appropriately substituted and compatible with reaction conditions.

The compounds of the present invention may also be synthesized according to the methods of U.S. Pat. No. 5,547,975.

The complete content of all publications, patents, and patent applications cited in this disclosure are herein incorporated by reference as if each individual publication, patent, or patent application were specifically and individually indicated to incorporated by reference. Although the foregoing invention has been described in some detail by way of illustration and example for the purposes of clarity of understanding, it will be readily apparent to one skilled in the art in light of the teachings of this invention that changes and modifications can be made without departing from the spirit and scope of the present invention. The following examples are provided for exemplification purposes only and are not intended to limit the scope of the invention, which has been described in broad terms above.

EXAMPLES

Example 1 ethyl 1-{4-[(aminothio)peroxy]phenyl}-8-nitro-4,5-dihydro-1H-benzo[g]indazole-3-carboxylate

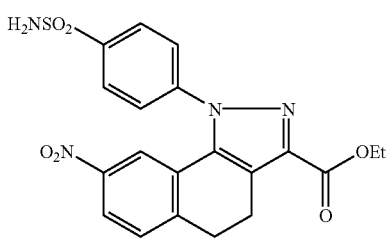

Step 1

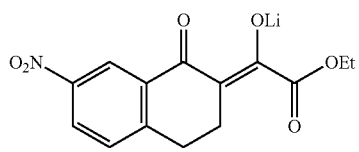

To 7-nitro-1-tetralone (4.6 g, 0.024 mol) and ethyl oxalate (3.5 mL, 0.026 mol) in ether (100 mL) was added dropwise lithium bis(trimethylsilyl)amide (1M in THF, 26 mL). The slurry was stirred overnight and filtered to give the product as an olive green solid, 6.2 g (87% yield). $^1$H NMR (DMSO-$d_6$/300 MHz) 8.45 (d, 1H); 8.05 (d of d, 1H); 7.42 (d, 1H); 4.08 (q, 2H); 2.82–2.72 (m, 2H); 2.51–2.43 (m, 2H); 1.21 (t, 3H).

Step 2

The material of step 1 (6.2 g, 0.021 mol) and 4-sulfonamidophenylhydrazine hydrochloride (5.1 g, 0.023 mol) were stirred in methanol (100 mL) overnight. Conc HCl (2 mL) was added to the thick slurry and the contents were heated on a steam bath for 1 hour. Contents were allowed to cool and filtered to give an off-white solid, 6.9 g. NMR and LC/MS analysis show the solid to contain two components, the desired, and the hydrated pyrazole. TFA (60 mL) and TFAA (20 mL) were added to the solid and heated on a steam bath for 1 hour. Contents were concentrated in vacuo leaving the product as a solid, 6.4 g (69% yield). FABHRMS m/z 443.1020 (M+H, $C_{20}H_{19}N_4O_6S$ requires 443.1025). $^1$H NMR (DMSO-$d_6$/300 MHz) 8.10 (d of d, 1H); 8.03 (d, 2H); 7.82 (d, 2H); 7.70 (d, 1H); 7.62 (s, 1H); 7.50 (d, 1H); 4.33 (q, 2H); 3.20–2.95 (m, 4H); 1.33 (t, 3H).

Anal. Calcd for $C_{20}H_{18}N_4O_6S$: C, 54.29; H, 4.10; N, 12.66. Found: C, 54.49; H, 4.00; N, 12.52.

Example 2

1-{4-[(aminothio)peroxy]phenyl}-8-nitro-4,5-dihydro-1H-benzo[g]indazole-3-carboxamide

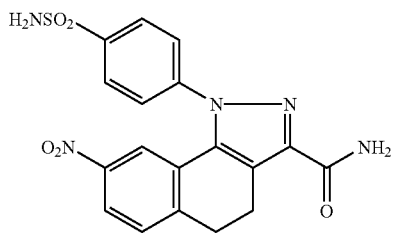

The final product of Example 1 (718 mg, 0.0016 mol), conc. ammonium hydroxide (30 mL), and methanol (15 mL) were stirred in a stoppered flask for 72 hours. Contents were filtered to give a light amber solid (606 mg). The solid was recrystallized from acetonitrile to give the product as a light amber solid, 450 mg (68% yield). FABHRMS m/z 414.0902 (M+H, $C_{18}H_{16}N_5O_5S$ requires 414.0872). $^1$H NMR (DMSO-$d_6$/300 MHz) 8.15–7.95 (m, 3H); 7.83 (d, 2H); 7.80–7.40 (m, 6H); 3.20–2.95 (m, 4H).

Anal. Calcd for $C_{18}H_{15}N_5O_5S$: C, 52.30; H, 3.66; N, 16.94. Found: C, 52.04; H, 3.64; N, 16.61.

Example 3 ethyl 8-amino-1-[4-(aminosulfonyl)phenyl]-4,5-dihydro-1H-benzo[g]indazole-3-carboxylate

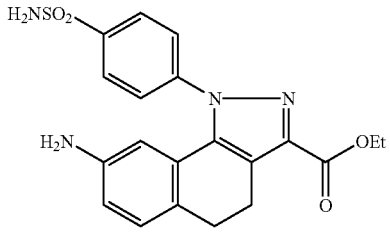

The final product of Example 1 (2.0 g) and 10% Pd/C (350 mg) in DMF (20 mL) were shaken at 55 psi hydrogen for 3 hours. Contents were filtered and the filtrate was concentrated in vacuo leaving an amber wax. The wax was triterated with methanol and filtered to give the product as a light amber solid, 1.6 g (86% yield). FABHRMS m/z 413.1293 (M+H, $C_{20}H_{21}N_4O_4S$ requires 413.1284). $^1$H NMR (DMSO-$d_6$/300 MHz) 8.00 (d, 2H); 7.73 (d, 2H); 7.50 (s, 2H); 7.01 (d, 1H); 6.43 (d of d, 1H); 6.00 (d, 1H); 4.83 (br s, 2H); 4.30 (q, 2H); 2.85–2.70 (m, 4H); 1.31 (t, 3H).

Anal. Calcd for $C_{20}H_{20}N_4O_4S$ (0.25$H_2O$): C, 57.61; H, 4.96; N, 13.44. Found: C, 57.62; H, 5.11; N, 13.15.

Example 4

8-amino-1-{4-[(aminothio)peroxy]phenyl}-4,5-dihydro-1H-benzo[g]indazole-3-carboxamide

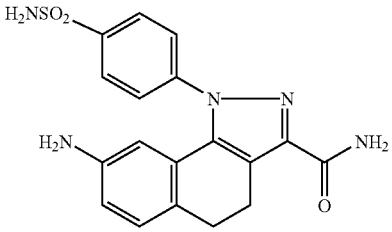

Example 4 was prepared similarly to Example 2 in 70% yield. FABHRMS m/z 384.1136 (M+H, $C_{18}H_{18}N_5O_3S$ requires 384.1130). $^1$H NMR (DMSO-$d_6$/300 MHz) 7.95 (d, 2H); 7.75 (d, 2H); 7.53 (br s, 1H); 7.43 (br s, 1H); 7.32 (br s, 1H); 7.01 (d, 1H); 6.44 (d of d, 1H); 6.03 (s, 1H); 4.81 (s, 2H); 2.93–2.65 (m, 4H).

Anal. Calcd for $C_{18}H_{17}N_5O_3S$: C, 56.38; H, 4.47; N, 18.27. Found: C, 56.31; H, 4.42; N, 18.31.

Example 5 ethyl (6-hydroxy-1-oxo-1,2,3,4-tetrahydronaphthalen-2-yl)(oxo)acetate

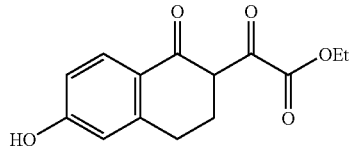

To 6-hydroxy-1-tetralone (10.4 g, 0.064 mol) and ethyl oxalate (17.4 mL, 0.128 mol) in THF (100 mL) was added dropwise lithium bis(trimethylsilyl)amide (1M in THF, 130 mL). The slurry was stirred overnight and a solid was filtered. The solid was dissolved in water and made acidic to pH 2.5 with 3 N HCl, precipitating a waxy solid. The waxy solid was extracted into EtOAc, dried (MgSO$_4$), and concentrated in vacuo leaving a dark solid (15.7 g). The solid was purified by chromatography on silica gel, eluting with 15% EtOAc/hexanes to give a yellow solid (5.9 g). The solid was recrystallized from EtOAc/hexanes to give the product as a yellow solid, 3.7 g (22% yield). FABHRMS m/z 263.0925 (M+H, $C_{14}H_{15}O_5$ requires 263.0919). $^1$H NMR (CDCl$_3$/300 MHz) 7.93 (d, 1H); 6.80 (d of d, 1H); 6.68 (s, 1H); 5.72 (s, 1H); 4.39 (q, 2H); 3.00–2.75 (m, 4H); 1.40 (t, 3H).

Anal. Calcd for $C_{14}H_{14}O_5$: C, 64.12; H, 5.38. Found: C, 63.79; H, 5.35.

Example 6 ethyl 1-[4-(aminosulfonyl)phenyl]-7-hydroxy-4,5-dihydro-1H-benzo[g]indazole-3-carboxylate

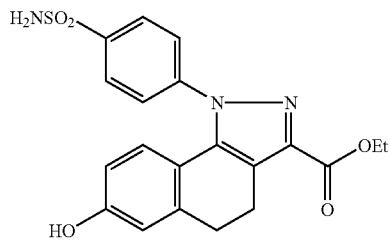

The material prepared in Example 5 (2.0 g, 0.0076 mol) and 4-sulfonamidophenylhydrazine hydrochloride (1.9 g, 0.0085) were stirred in glacial acetic acid (25 mL) for 96 hours. Contents were heated at 55° C. for 5 hours, allowed to cool, diluted with water (75 mL), and filtered to give the product as a white solid, 3.1 g (90% yield). FABHRMS m/z 414.1146 (M+H, $C_{20}H_{20}N_3O_5S$ requires 414.1124). $^1$H NMR (DMSO-$d_6$/300 MHz) 9.72 (s, 1H); 8.00 (d, 2H); 7.73 (d, 2H); 7.53 (s, 1H); 6.80 (s, 1H); 6.60–6.40 (m, 2H); 4.30 (q, 2H); 2.90 (s, 4H); 1.30 (t, 3H).

Anal. Calcd for $C_{20}H_{19}N_3O_5S$ (0.2 $H_2O$): C, 57.60; H, 4.69; N, 10.08. Found: C, 57.72; H, 4.91; N, 9.68.

Example 7 ethyl 1-{4-[(aminothio)peroxy]phenyl}-8-fluoro-1,4-dihydrochromeno[4,3-c]pyrazole-3-carboxylate

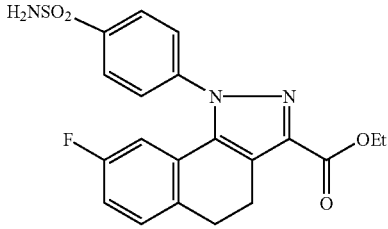

Step 1

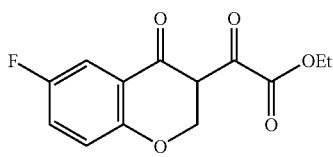

The material of product of step 1 was prepared similarly to Example 5 in 75% yield. FABHRMS m/z 267.0673 (M+H, $C_{13}H_{12}FO_5$ requires 267.0669). $^1$H NMR (CDCl$_3$/300 MHz) 7.56 (d of d, 1H); 7.25–7.15 (m, 1H); 7.00–6.90 (m, 1H); 5.35 (s, 2H); 4.40 (q, 2H); 1.40 (t, 3H).

Anal. Calcd for $C_{13}H_{11}FO5$: C, 58.65; H, 4.16. Found: C, 58.38; H, 4.03.

Step 2

The final product of Example 7 was prepared similarly to Example 6 starting with the material of step 1 in 75% yield. FABHRMS m/z 418.0872 (M+H, $C_{19}H_{17}FN_3O_5S$ requires 418.0873). $^1$H NMR (DMSO-d$_6$/300 MHz) 8.05 (d, 2H); 7.82 (d, 2H); 7.60 (s, 1H); 7.20–7.00 (m, 2H); 6.40 (d, 1H); 5.47 (s, 2H); 4.31 (q, 2H); 1.30 (t, 3H).

Anal. Calcd for $C_{19}H_{16}FN_3O_5S$: C, 54.67; H, 3.86; N,10.07. Found: C, 54.91; H, 3.86; N,10.21.

Example 8

1-{4-[(aminothio)peroxy]phenyl}-8-fluoro-1,4-dihydrochromeno[4,3-c]pyrazole-3-carboxamide

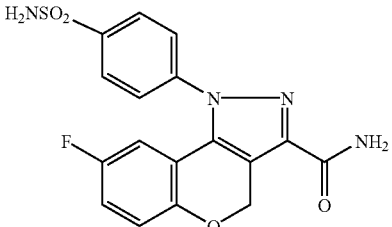

Example 8 was prepared similarly to Example 2 starting with the product of Example 7 in 68% yield. FABHRMS n/z 389.0720 (M+H, $C_{17}H_{14}FN_4O_4S$ requires 389.0741). $^1$H NMR (DMSO-d$_6$/300 MHz) 8.05 (d, 2H); 7.82 (d, 2H); 7.75 (s, 1H); 7.58 (s, 1H); 7.51 (s, 1H); 7.15–7.00 (m, 2H); 6.40 (d of d, 1H); 5.45 (s, 2H).

Anal. Calcd for $C_{17}H_{13}FN_4O_4S$: C, 52.57; H, 3.37; N, 14.43. Found: C, 52.45; H, 3.32; N, 14.54.

Example 9 ethyl 1-{4-[(aminothio)peroxy]phenyl}-1,5-dihydroisothiochromeno[4,3-c]pyrazole-3-carboxylate

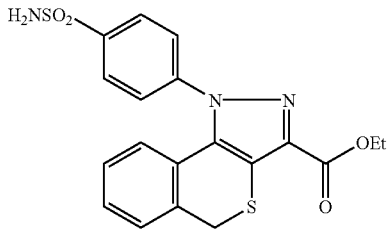

Step 1

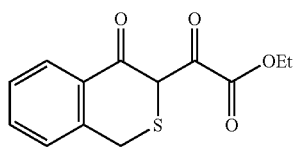

The material of step 1 was prepared similarly to Example 5 in 74% yield. FABHRMS m/z 265.0496 (M+H, $C_{13}H_{13}O_4S$ requires 265.0535). $^1$H NMR (CDCl$_3$/300 MHz) 8.00 (d, 1H); 7.60–7.50 (m, 1H); 7.50–7.40 (m, 1H); 7.32–7.20 (m, 1H); 4.42 (q, 2H); 3.80 (s, 2H); 1.42 (t, 3H).

Anal. Calcd for $C_{13}H_{12}O_4S$: C, 59.08; H, 4.58. Found: C, 58.94; H, 4.47.

Step 2

The final product of Example 9 was prepared similarly to Example 6 starting with the material of step 1 in 35% yield. FABHRMS m/z 416.0736 (M+H, $C_{19}H_{18}N_3O_4S_2$ requires 416.0739). $^1$H NMR (DMSO-d$_6$/300 MHz) 8.01 (d, 2H); 7.82 (d, 2H); 7.60 (s, 2H); 7.51 (d, 1H) 7.37 (t, 1H); 7.20 (t, 1H); 6.72 (d, 1H); 4.35 (q, 2H); 4.11 (s, 2H); 1.30 (t, 3H).

Anal. Calcd for $C_{19}H_{17}N_3O_4S_2$ (0.5H$_2$O): C, 53.76; H, 4.27; N, 9.90. Found: C, 53.77; H, 4.10; N, 9.83.

Example 10

1-{4-[(aminothio)peroxy]phenyl}-1,5-dihydroisothiochromeno[4,3-c]pyrazole-3-carboxamide

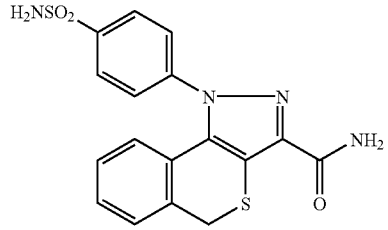

Example 10 was prepared similarly to Example 2 starting with the material of Example 9 in 56% yield. FABHRMS m/z 387.0623 (M+H, $C_{17}H_{15}N_4O_3S_2$ requires 387.0586). $^1$H NMR (DMSO-d$_6$/300 MHz) 8.00 (d, 2H); 7.83 (d, 2H); 7.74 (s, 1H); 7.60–7.40 (m, 4H); 7.40–7.30 (m, 1H); 7.24–7.10 (m, 1H); 6.75 (d, 1H); 4.05 (s, 2H).

Anal. Calcd for $C_{17}H_{14}N_4O_3S_2$ (0.5H$_2$O): C, 52.35; H, 3.72; N, 14.36. Found: C, 52.16; H, 3.57; N, 14.16.

Example 11

8-{4-[(aminothio)peroxy]phenyl}-4,8-dihydro[1,3]dioxolo[7,8]isothiochromeno[4,3-c]pyrazole-6-carboxamide

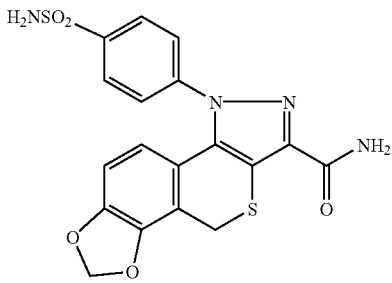

Step 1

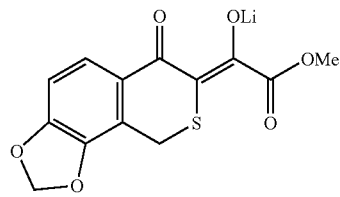

To 6,7-methylenedioxyisothiochroman-4-one (Example 33 of WO 96/09304) (362 mg, 0.00174 mol) and dimethyl oxalate (213 mg, 0.0018 mol) in ether (20 mL) was added dropwise lithium bis(trimethylsilyl)amide (1 M in THF, 1.8 mL). Contents were stirred 5 hours and filtered to give the product as a green solid, 700 mg. Used directly in Example 50. $^1$H NMR (DMSO-$d_6$/300 MHz) 7.30 (d, 1H); 6.75 (d, 1H); 6.03 (s, 2H); 3.55 (s, 3H); 3.48 (s, 2H).

Step 2

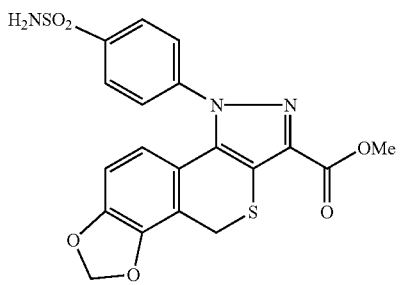

The material of step 1 (700 mg) and 4-aminosulfonylphenylhydrazine hydrochloride (575 mg, 0.002 mol) were mixed in methanol (20 mL) and stirred overnight. 3N HCl (6 mL) was added and contents were heated for 2 hours. After cooling and diluting with water (20 mL), the contents were filtered to give the product as an amber solid, 469 mg (53% yield). $^1$H NMR (DMSO-$d_6$/300 MHz) 8.00 (d, 2H); 7.81 (d, 2H); 7.55 (s, 1H); 7.49 (s, 1H); 6.82 (d, 1H); 6.26 (d, 1H); 6.15 (s, 2H); 3.95 (s, 3H); 3.85 (s, 2H).

Step 3

The final product of Example 11 was prepared similarly to Example 2 staring with the material of step 2 in 7% yield. FABHRMS m/z 431.0501 (M+H, $C_{18}H_{15}N_4O_5S_2$ requires 431.0484). $^1$H NMR (DMSO-$d_6$/300 MHz) 8.00 (d, 2H); 7.80 (d, 2H); 7.75 (s, 1H); 7.55 (s, 2H); 7.50 (s, 1H); 6.80 (d, 1H); 6.26 (d, 1H); 6.13 (s, 2H); 3.95 (s, 2H).

Anal. Calcd for $C_{18}H_{14}N_4O_5S_2$: C, 50.22; H, 3.28; N, 13.02. Found: C, 49.96; H, 3.23; N, 12.56.

Example 12 ethyl 1-[4-(aminosulfonyl)phenyl]-4,5-dihydro-1H-pyrazolo[4,3-c]quinoline-3-carboxylate

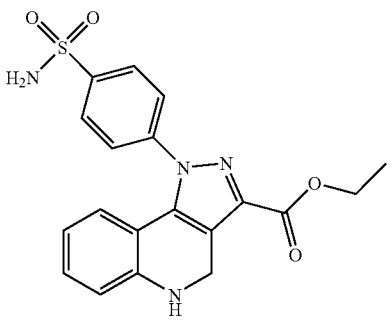

Step 1

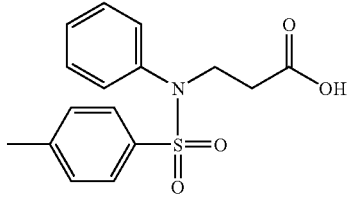

To aniline (10 mL, 10 mmol) was slowly added acrylic acid (7.6 mL, 110 mmol). After about 2 hours at ambient temperature a gel had formed. Pyridine (125 mL) was added, followed by 4-toluenesulfonyl chloride (20.9 gm, 110 mmol) in several portions. The reaction was stirred at ambient temperature for 3 hours, the pyridine was removed on a rotary evaporator. Water (100 mL0 was added to the residue and the solution was extracted with ethyl acetate (3×100 mL). The ethyl acetate layers were pooled and dried (MgSO$_4$). Filtration and concentration on a rotary evaporator produced a pale yellow oil. The oil was dissolved in saturated NaHCO$_3$ solution (50 mL) and extracted with ethyl acetate (2×100 mL). The organic layers were back extracted with saturated NaHCO$_3$ solution (3×50 mL). The aqueous layers were then made acidic and re-extracted with ethyl acetate (3×100 mL). The ethyl acetate layers were then pooled, washed with water and brine, and dried (MgSO$_4$). Filtration and concentration produced an off-white solid. Yield: 13.6 gm (58%). $^1$H-NMR ($d_6$-DMSO) 2.32 (t, 2H); 2.40 (s, 3H); 3.76 (t, 2H); 7.02 (d, 1H); 7.37 (m, 7H).

Step 2

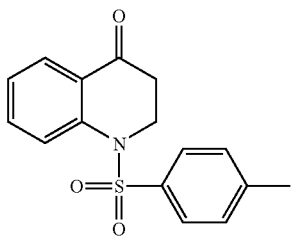

To the product of step 1 (13.5 gm, 42.3 mmol) was added TFA (5 mL) and TFAA (15 mL, 106.2 mmol). The reaction was heated to reflux for 3 hours, cooled to room temperature, and diluted with water (100 mL). The solution was extracted with ethyl acetate (2×100 mL). The ethyl acetate was pooled and washed with water and brine. Dried (MgSO$_4$), filtered and concentrated to a solid. Yield: 7.19 gm (57%). $^1$H-NMR (d$_6$-DMSO) 2.36 (s, 3H); 2.43 (t, 2H); 4.22 (t, 2H); 7.32 (t, 1H); 7.38 (d, 2H); 7.66 (m, 4H); 7.82 (d, 1H).

Step 3

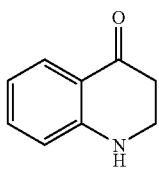

N-tosyl-4-azachromanone (2 gm, 6.6 mmol) in acetic acid (16 mL) and 6 N HCl (14 mL) and heated to reflux for 18 hours. The reaction was cooled to room temperature and diluted with water (75 mL), then extracted with ethyl acetate (3×50 mL). The ethyl acetate layers were pooled, washed with saturated NaHCO$_3$ solution until the pH remained above 7, then with water and brine. The organic solution was then dried (MgSO$_4$) filtered and concentrated to an oil. Chromatographed on silica, eluting with 4:1 hexane/ethyl acetate to obtain a clear colorless oil. Yield: 970 mg (ca. 100%). $^1$H-NMR (CDCl$_3$) 2.72 (t, 2H); 3.59 (t, 2H); 4.45 (bs, 1H); 6.68 (d, 1H); 6.75 (t, 1H); 7.31 (t, 1H); 7.86 (d, 1H).

Step 4

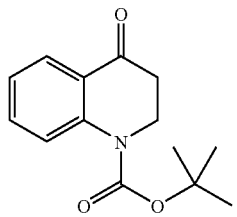

The 4-azachromanone (930 mg, 6.3 mmol) was dissolved in dichloromethane (15 mL) and triethylamine (876 uL, 6.3 mmol) and DMAP (768 mg, 6.3 mmol) were added. To the solution di-t-butyl dicarbonate (2.75 gm, 12.6 mmol) was added portionwise. The reaction was stirred at ambient temperature for 2 hours, then concentrated on a rotary evaporator to an oil. The oil was chromatographed on silica eluting with 10% ethyl acetate/hexane. A clear colorless oil was obtained. Yield 1.16 gm (74%). $^1$H-NMR (CDCl$_3$) 1.58 (s, 9H); 2.79 (t, 2H); 4.18 (d, 2H); 7.17 (t, 1H); 7.51 (t, 1H); 7.78 (d, 1H); 8.01 (d, 1H).

Step 5

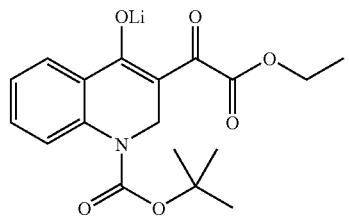

N-Boc-4-azachromanone (880 mg, 3.5 mmol) was dissolved in diethyl ether (30 mL) and 1M LHMDS (3.9 mL, 3.9 mmol) was added dropwise over several minutes. A precipitate slowly formed and the reaction became light yellow. After about 15 minutes, diethyl oxalate (529 uL, 3.9 mmol) was added and the reaction stirred at room temperature. After 15 minutes a second aliquot of LHMDS (3 mL, 3 mmol) and diethyl oxalate (500 uL, 3.8 mmol) was added. After 24 hours, the resulting precipitate was collected by suction filtration and washed with diethyl ether. A cream colored solid was obtained. Yield; 578 mg. A second crop was recovered from the mother liquor, 529 mg (88% combined). $^1$H-NMR (d$_6$-DMSO) 1.20 (t, 3H); 1.46 (s, 9H); 4.86 (q, 2H); 4.38 (s, 2H); 7.06 (t, 1H); 7.28 (t, 1H); 7.46 (d, 1H); 7.69 (d, 1H).

Step 6

The enolate from step 5 (530 mg, 1.5 mmol) was combined with 4-sulfonamidophenylhydrazine hydrochloride (669 mg, 2 mmol) in THF (6 mL) and acetic acid (3 mL). The reaction was stirred at ambient temperature for 48 hours, then heated to reflux to complete the cyclization, the THF was allowed to boil off and was replaced with acetic acid (6 mL). After an additional 24 hours, the resulting yellow precipitate was collected by suction filtration and washed with a small amount of THF. Yield 356 mg (60%) with loss of the t-butoxycarbonyl protecting group. $^1$H-NMR (d$_6$-DMSO+TFA) 1.30 (t, 3H); 4.30 (q, 2H); 4.70 (s, 2H); 6.35 (t, 1H); 6.43 (d, 1H); 6.71 (d, 1H); 6.97 (t, 1H); 7.76 (d, 2H); 8.04 (d, 2H).

Example 13

1-[4-(aminosulfonyl)phenyl]-4,5-dihydro-1H-pyrazolo[4,3-c]quinoline-3-carboxamide

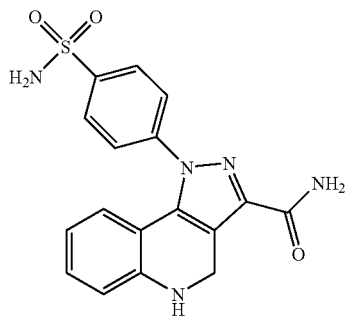

The ethyl ester from Example 12 (100 mg, 0.25 mmol) was suspended in methanol (2 mL) and bubbled with NH$_3$ gas at room temperature for 10 minutes, then cooled to −78° C. and about 1 mL of ammonia was condensed into the reaction mixture. The reaction was allowed to stand at ambient temperature in a sealed tube for 6 days. The reaction was cooled to −78° C., the vessel opened, and the solvents allowed to evaporate at room temperature. The residue was dissolved in methanol (15 mL) and filtered. The solution was then concentrated under a stream of nitrogen until a crystalline solid had formed. The solid was collected and washed with diethyl ether. Obtain pale yellow solid. Yield: 74 mg (80%). $^1$H-NMR (d$_6$-DMSO) 4.69 (s, 2H); 6.32 (t, 1H); 6.44 (d, 1H); 6.67 (d, 1H); 6.95 (t, 1H); 7.57 (bs, 2H); 7.76 (d, 2H); 8.02 (d, 2H). FABHRMS m/z 370.0963 (M+H, C$_{17}$H$_{16}$N$_5$O$_3$S requires 370.0974).

Example 14 ethyl 1-[4-(aminosulfonyl)phenyl]-5-[(4-methylphenyl)sulfonyl]-4,5-dihydro-1H-pyrazolo[4,3-c]quinoline-3-carboxylate

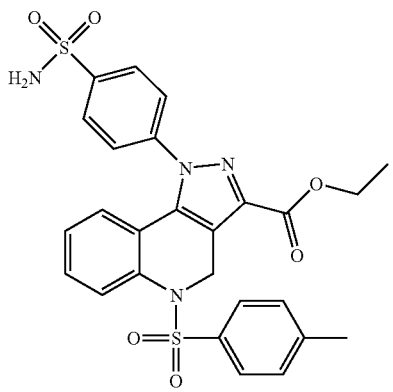

Step 1

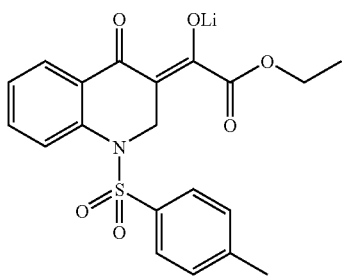

The product of step 2 of Example 12 (3.01 gm, 10 mmol) was condensed with diethyl oxalate (10 mmol) in the presence of LHMDS in the same fashion as Example 6. Obtain a light brown powder. Yield 2.26 gm (55%). $^1$H-NMR (d$_6$-DMSO) 1.18 (t, 3H); 2.36 (s, 3H); 3.98 (q, 2H); 4.61 (s, 2H); 7.13 (m, 3H); 7.32 (m, 3H); 7.50 (d, 2H); 7.60 (d, 2H).

Step 2

The product of step 1 (2.04 gm, 5 mmol) was condensed with 4-sulfonamidophenylhydrazine hydrochloride (1.3 gm, 5.8 mmol) according to the procedure of Example 6. The reaction was concentrated to a residue that was run through a plug of silica gel (ca. 50 gm) eluted with 3:1 CH$_2$Cl$_2$/CH$_3$CN (500 mL). The resulting solution was concentrated and the residue triturated with methanol (25 mL). Obtain white solid. Yield 1.85 gm (67%). $^1$H-NMR (d$_6$-DMSO) 1.39 (t, 3H); 2.13 (s, 3H); 4.42 (q, 2H); 5.12 (s, 2H); 6.71 (d, 1H); 7.16 (s, 4H); 7.25 (m, 3H); 7.50 (t, 1H); 7.61 (s, 2H, SO$_2$NH$_2$); 7.75 (d, 1H); 8.00 (d, 2H).

Example 15

1-[4-(aminosulfonyl)phenyl]-5-[(4-methylphenyl)sulfonyl]-4,5-dihydro-1H-pyrazolo[4,3-c]quinoline-3-carboxamide

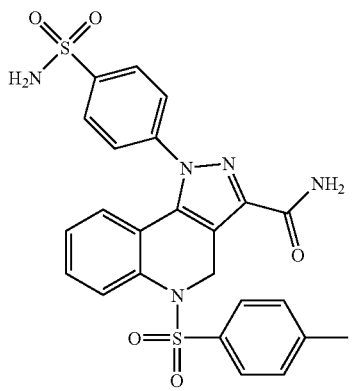

The product of Example 14 (1.48 gm, 2.7 mmol) was converted to the amide in the same manner as Example 3. Concentrated on a rotary evaporator until a fine white precipitate was obtained. The solid was washed with water, then carefully with a small amount methanol, then ether and dried in-vacuo. Obtain white solid. Yield 1.15 gm (81%). $^1$H-NMR (d$_6$-DMSO) 2.12 (s, 3H); 5.11 (s, 2H); 6.73 (d, 1H); 7.13 (s, 4H); 7.21 (m, 3H); 7.48 (t, 1H); 7.56 (m, 3H); 7.72 (t, 1H); 7.99 (d, 2H).

Example 16

1-[4-(aminosulfonyl)phenyl]-1,4-dihydrochromeno[4,3-c]pyrazole-3-carboxamide

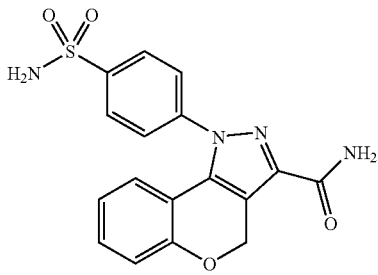

Step 1
Preparation of (2Z)-hydroxy(4-oxo-2H-1-benzopyran-3(4H)-ylidene)ethanoic acid, methyl ester To a solution of 4-chromanone (6.1097 g, 40.0 mmol) and dimethyl oxalate (5.759 g, 48.28 mmol) in methanol (50 ml), a solution of 0.5M sodium methoxide (96.9 ml, 48.28 mmol) was added dropwise at RT under N$_2$ over 20 min. The colorless solution turned to yellow. The solution was stirred at RT under N$_2$ overnight. After 16 h, the reaction solution was removed under reduced pressure. The residue was diluted with EA, washed with H$_2$O and brine, dried over MgSO$_4$. After filtration, the solvent was removed under reduced pressure to yield crude product methyl ester of (2Z)-hydroxy(4-oxo-2H-1-benzopyran-3(4H)-ylidene) ethanoic acid (8.9096 g, 95.2%) after dried under vacuum.

Step 2
Preparation of 1-[4-(aminosulfonyl)phenyl]-1,4-dihydro-[1]benzopyrano[4,3-c]pyrazole-3-carboxylic acid, methyl ester To a solution of methyl ester of (2Z)-hydroxy(4-oxo-2H-1-benzopyran-3(4H)-ylidene)ethanoic acid prepared in step 1 (1.17 g, 5.0 mmol) in methanol (50 ml) (SM was not dissolved in methanol until it was heated to 60° C.), 4-sulphonamidophenylhydrazine (1.2328 g, 5.51 mmol) was added. There was precipitate formed. The reaction mixture was heated to reflux under $N_2$ overnight. The precipitate was filtrated off, washed with MeOH, collected and dried under vacuum to give desired product methyl ester of 1-[4-(aminosulfonyl)phenyl]-1,4-dihydro-[1]benzopyrano[4,3-c]pyrazole-3-carboxylic acid (1.16115 g, 84%).

Step 3
Preparation of 1-[4-(aminosulfonyl)phenyl]-1,4-dihydro-[1]benzopyrano[4,3-c]pyrazole-3-carboxamide To a suspension of methyl ester of 1-[4-(aminosulfonyl)phenyl]-1,4-dihydro-[1]benzopyrano[4,3-c]pyrazole-3-carboxylic acid (0.77 g, 2.0 mmol) in MeOH (50 ml) in a pressure tube, liquid $NH_3$ (5 ml) was added. The pressure tube was sealed at RT and then heated to 60° C. overnight. The suspension became clear solution. After 24 h, the solution was cooled to RT and pressure was relieved. The solvent was removed under reduced pressure. The resulting white solids were recrystallized in MeOH, to yield pure product 1-[4-(aminosulfonyl)phenyl]-1,4-dihydro-[1]benzopyrano[4,3-c]pyrazole-3-carboxamide (0.3584 g, 48%). Mass (MH$^+$) 137. Anal. Calc'd for $C_{17}H_{14}O_4N_4S$+ $0.4H_2O$: C, 54.08; H, 3.95; N, 14.86. Found: C, 54.13; H, 3.90; N, 14.86.

Table 1 shows the compound identification, compound, IKK heterodimer assay values expressed as IC50 for Examples 7–16.

TABLE 1

| COMPOUND | STRUCTURE | EXAMPLE | HetD |
| --- | --- | --- | --- |
| ethyl 1-{4-[(aminothio)peroxy]phenyl}-8-fluoro-1,4-dihydrochromeno[4,3-c]pyrazole-3-carboxylate | 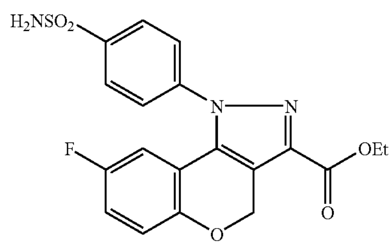 | Example 7 | >100 μM |
| 1-{4-[(aminothio)peroxy]phenyl}-1-8-fluoro-1,4-dihydrochromeno[4,3-c]pyrazole-3-carboxamide | 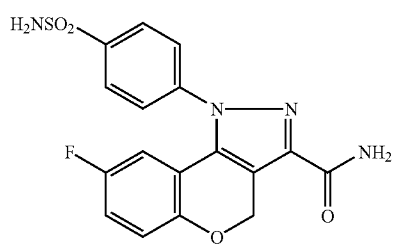 | Example 8 | 10 ≦ 100 μM |
| ethyl 1-{4-[(aminothio)peroxy]phenyl}-1,5-dihydroisothiochromeno[4,3-c]pyrazole-3-carboxylate | 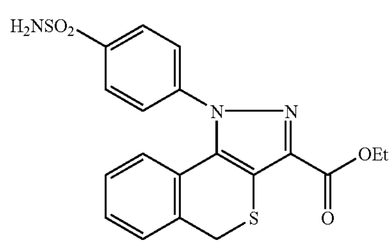 | Example 9 | >100 μM |
| 1-{4-[(aminothio)peroxy[phenyl }-1,5-dihydroisothiochromeno[4,3-c]pyrazole-3-carboxamide | 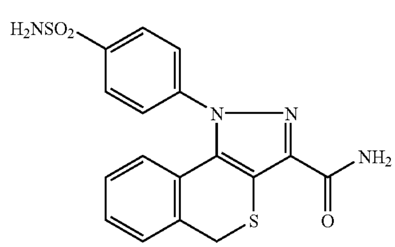 | Example 10 | >100 μM |

TABLE 1-continued

| COMPOUND | STRUCTURE | EXAMPLE | HetD |
|---|---|---|---|
| 8-{4-[(aminothio)peroxy]phenyl}-4,8-dihydro[1,3 dioxolo[7,8] isothiochromeno[4,3-c]pyrazole-6-carboxamide | 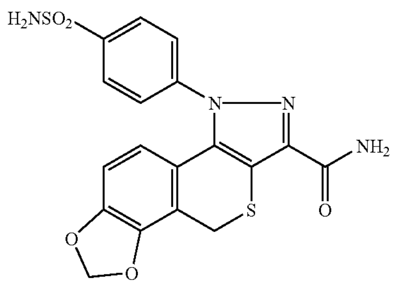 | Example 11 | >100 μM |
| ethyl 1-[4-(aminosulfonyl)phenyl]-4,5-dihydro-1H-pyrazolo[4,3-c]quinoline-3-carboxylate | 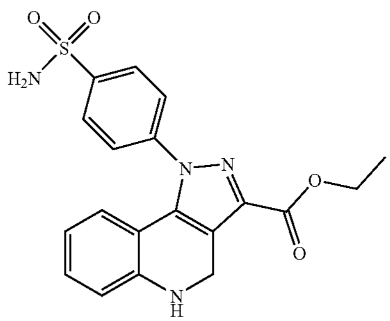 | Example 12 | >100 μM |
| 1-[4-(aminosulfonyl)phenyl]-4,5-dihydro-1H-pyrazolo[4,3-c]quinoline-3-carboxamide | 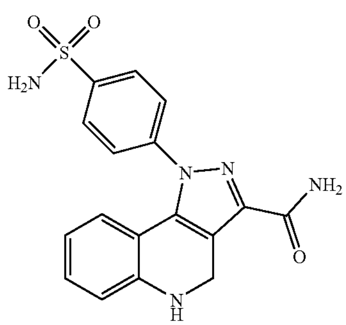 | Example 13 | 1 ≦ 10 μM |
| ethyl 1-[4-(aminosulfonyl)phenyl]-5-[(4-methylphenyl)sulfonyl]-4,5-dihydro-1H-pyrazolo[4,3-c]quinoline-3-carboxylate | 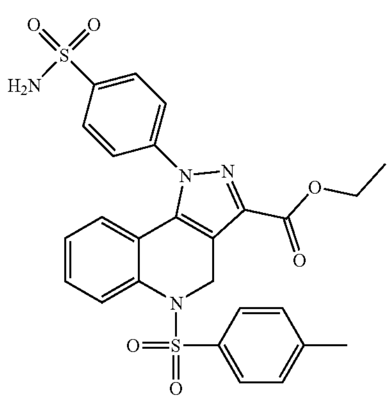 | Example 14 | >100 μM |

TABLE 1-continued
| COMPOUND | STRUCTURE | EXAMPLE | HetD |
|---|---|---|---|
| 1-[4-(aminosulfonyl)phenyl]-5-[(4-methylphenyl)sulfonyl]-4,5-dihydro-1H-pyrazolo[4,3-c]quinoline-3-carboxamide | 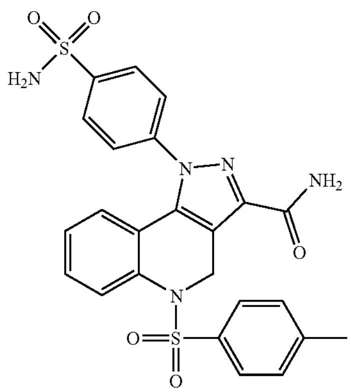 | Example 15 | >100 μM |
| 1-[4-(aminosulfonyl)phenyl]-1,4-dihydrochromeno[4,3-c]pyrazole-3-carboxamide | 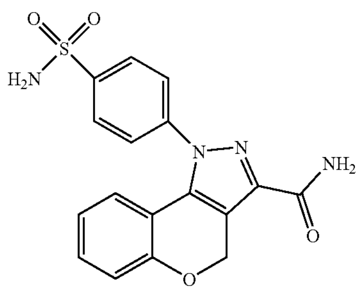 | Example 16 | 1 ≦ 10 μM |
Examples 17 and 18 were synthesized using the following general scheme.
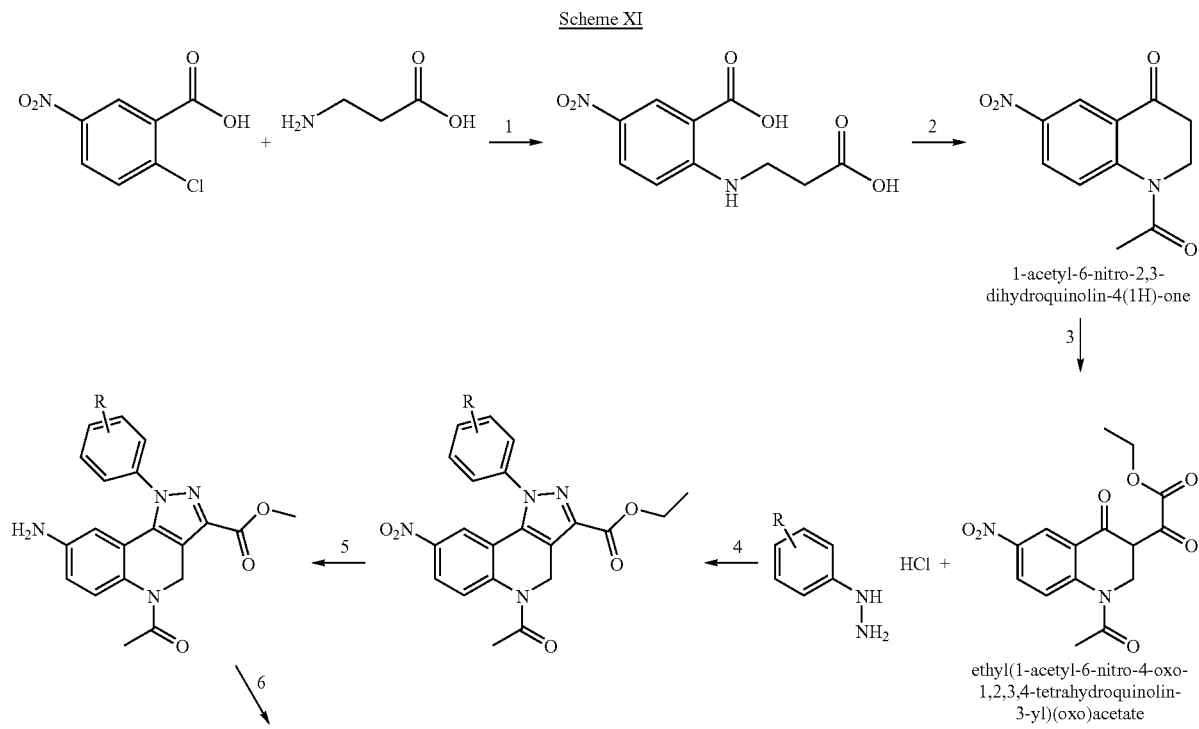
Scheme XI -continued

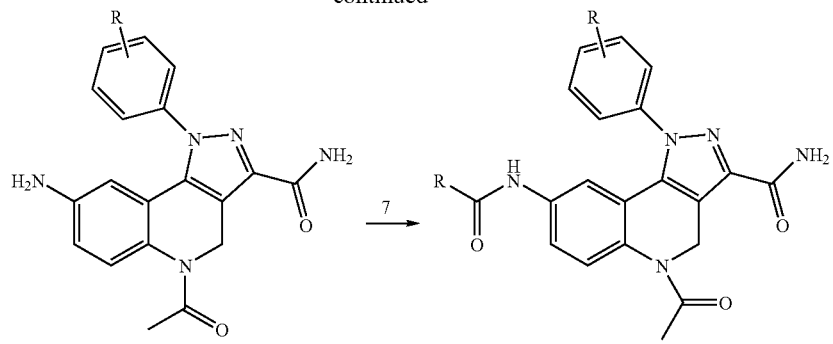

1) NaOAc, CuOAc, K₂CO₃, Isoamyl Alcohol, reflux, 3hr 2) Acetic Anhydride, KOAc, 90 C, 2hr 3) LiHMDSA, Diethyl Oxalate, -78 C-1 hr, r t -18 hr
4) Acetic Acid, 60 C, 6hr 5) H₂, Pd, 5 psi, Acetic Acid, r.t, 18hr 6) NH₃, 600 psi, Ethanol, 120 C, 18hr 7) ROCl, pyridine, r t., 5hr

Example 17

5-acetyl-8-amino-1-(1,3-benzodioxol-5-yl)-4,5-dihydro-1H-pyrazolo[4,3-c]quinoline-3-carboxamide acetate

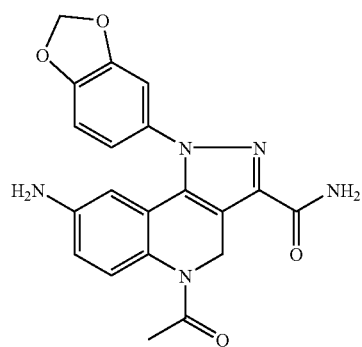

Step 1

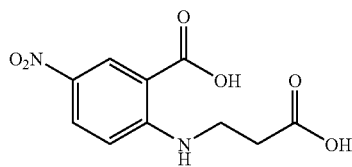

To 2-chloro-5-nitrobenzoic acid (30 g, 0.149 mol) and β-alanine (13.3 g, 0.149 mol) in isoamyl alcohol (200 mL), was added the potassium carbonate (33 g, 0.238 mol), sodium acetate (13.5 g, 0.164 mol), and the copper acetate (2.7 g, 0.0149 mol). The slurry was stirred with a mechanical stirrer and heated to reflux for 3 hours. The resulting solid was filtered and washed with acetone. The yellow solid was then dissolved in hot 0.1 N NaOH (200 mL) and the solution was then stirred with charcoal. The resulting suspension was filtered and the filtrate was cooled to room temperature and then acidified to pH~3 with 1N HCl. The resulting precipitate was filtered and recrystallized from hot DI water to give the desired product. 28.4 g (MW=254.05 g/mol, 75% yield). LC/MS m/z=255.1 (m+1).

Step 2

1-acetyl-6-nitro-2,3-dihydroquinolin-4(1H)-one

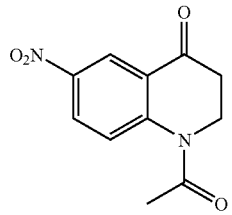

The material of Step 1 (5 g, 0.0197 mol), and potassium acetate (2.9 g, 0.0295 mol) were suspended in acetic anhydride (50 mL) and heated to 90° C. for 2 hours. The reaction was then cooled to room temperature in an ice bath and the acetic anhydride was removed in vacuo. The resulting material was chromatographed (silica gel 60, 10% Ethanol:Toluene) to produce the desired product. 3.7 g (MW=234.21 g/mol, 80% yield). LC/MS m/z=235.2 (m+1).

Step 3 ethyl (1-acetyl-6-nitro-4-oxo-1,2,3,4-tetrahydroquinolin-3-yl)(oxo)acetate

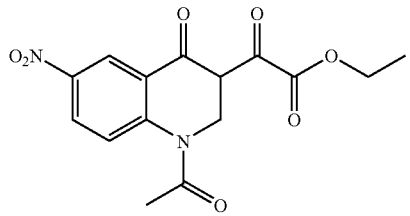

To the material of Step 2 (4.8 g, 0.0205 mol) in THF (25 mL) at −78° C., was added the lithium bis(trimethylsilyl)amide (20.5 mL of a 1M in THF solution). The diethyl oxalate (3 g, d=1.076 g/mL, 2.8 mL, 0.0205 mol) was then added and the reaction mixture was allowed to warm to room temperature and stir overnight. The slurry was then filtered to give an orange solid. 6.1 g (MW=334.28 g/mol, 90% yield). LC/MS m/z=335 (m+1).

Step 4 ethyl 5-acetyl-1-(1,3-benzodioxol-5-yl)-8-nitro-4,5-dihydro-1H-pyrazolo[4,3-c]quinoline-3-carboxylate

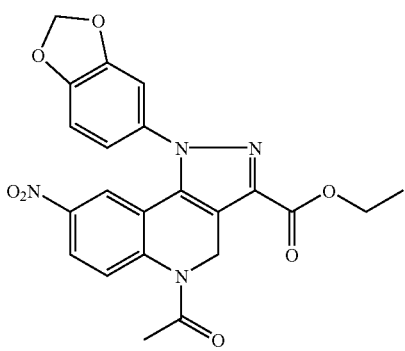

The material of Step 3 (1.1 g, 0.00331 mol) and 1-(1,3-benzodioxol-5-yl)hydrazine hydrochloride (500 mg, 0.00265 mol) were combined in acetic acid (10 mL) and heated to 60° C. for 5 hours. The suspension was then cooled and filtered to give the product as a brown solid. 930 mg (MW=450.4 g/mol, 78% yield). LC/MS m/z=451.5 (m+1).

Step 5 ethyl 5-acetyl-8-amino-1-(1,3-benzodioxol-5-yl)-4,5-dihydro-1H-pyrazolo[4,3-c]quinoline-3-carboxylate

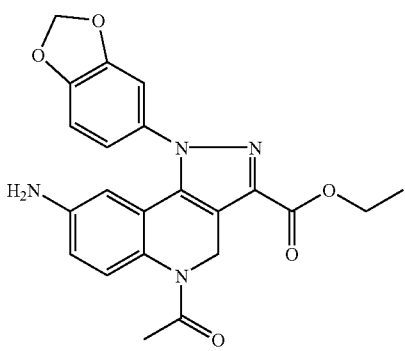

The material from Step 4 (930 mg, 0.00206 mol) was dissolved in acetic acid (25 mL), treated with a catalytic amount of 20% Pd(OH)$_2$, and shaken for 12 hours, under 5 psi, at room temperature. The suspension was then filtered, and the filtrate was concentrated in vacuo to give the desired product as the acetic acid salt. 850 mg (MW=480.46, 87% yield). LC/MS m/z=421.6 (m+1).

Step 6

5-acetyl-8-amino-1-(1,3-benzodioxol-5-yl)-4,5-dihydro-1H-pyrazolo[4,3-c]quinoline-3-carboxamide acetate

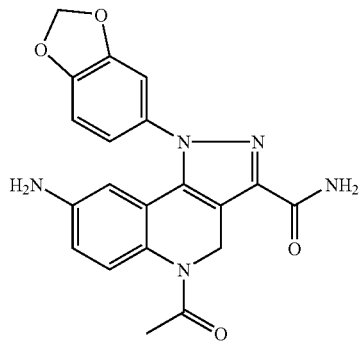

The material of Step 5 (450 mg, 0.00094 mol) was dissolved in ethanol (10 mL) and NH$_3$ (10 mL), and the resulting reaction mixture was heated to 120° C. and shaken for 20 hours at 600 psi. The reaction was then cooled and vented for 2 hours. The resulting solution was concentrated in vacuo to give the product as a brown glass. 340 mg (MW=391.38, 93% yield). LC/MS m/z=392.05 (m+1).

Example 18

5-acetyl-1-(1,3-benzodioxol-5-yl)-8-[(2-chlorobenzoyl)amino]-4,5-dihydro-1H-pyrazolo[4,3-c]quinoline-3-carboxamide

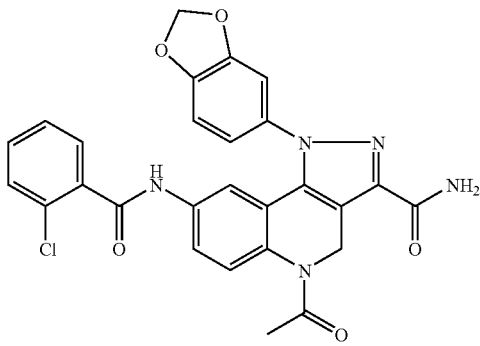

The title material from Example 17 (280 mg, 0.00072 mol) and 2-chlorobenzyl chloride (126 mg, 0.00072 mol, d=1.382 g/mol, 91 μL) were dissolved in pyridine (2 mL) and stirred for 4 hours. The pyridine was removed in vacuo and the resulting material was purified via HPLC to give the title compound. 95 mg (MW=529.93, 25% yield). LC/MS m/z=530.96 (m+1).

Examples 19 and 20 were synthesized by the following general scheme.

Scheme XII

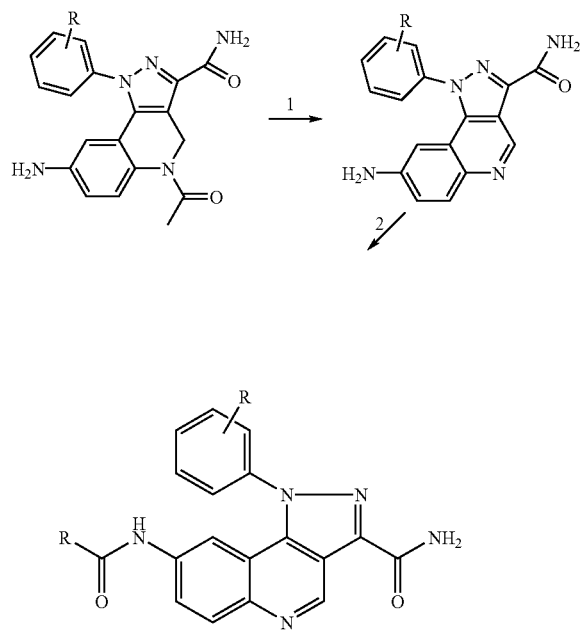

1.) concentrated HCl, reflux, 2 hr. 2.) ROCl, pyridine, r.t, 6 hr.

Example 19

8-amino-1-(1,3-benzodioxol-5-yl)-1H-pyrazolo[4,3-c]quinoline-3-carboxamide hydrochloride

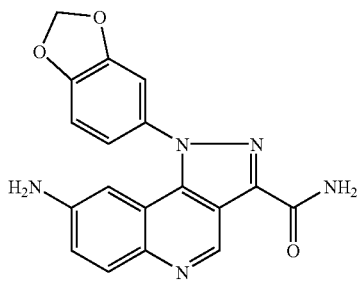

The title material from Example 17 (50 mg, 0.00013 mol) was dissolved in concentrated HCl(38%) (2 mL) and heated to reflux for 2. hours. The reaction was allowed to cool and the resulting precipitate was filtered. The yellow solid was triturated with water and dried under vacuum to give an off-white solid as the monohydrochloric acid salt. 45 mg. (MW=383.79, 89% yield). LC/MS m/z=348.4 (m+1).

Example 20

1-(1,3-benzodioxol-5-yl)-8-{[(2-chloropyridin-3-yl)carbonyl]amino}-1H-pyrazolo[4,3-c]quinoline-3-carboxamide

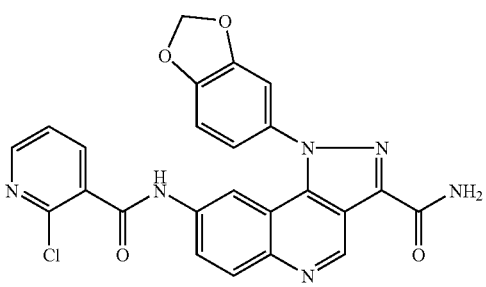

The title material from Example 19 (310 mg, 0.00088 mol) was dissolved in pyridine (2 mL). To this solution was added the 2-chloro-nicotinyl chloride (155 mg, 0.00088 mol). The reaction was stirred for 18 hours at room temperature. The reaction was then concentrated in vacuo and the resulting material was purified by reverse-phase HPLC to give the product as a white solid. 34 mg. (MW=486.87, 8% yield). LC/MS m/z=487.6 (m+1).

Example 21

5-acetyl-1-(1,3-benzodioxol-5-yl)-8-{[(2-chloropyridin-3-yl)carbonyl]amino}-4,5-dihydro-1H-pyrazolo[4,3-c]quinoline-3-carboxamide

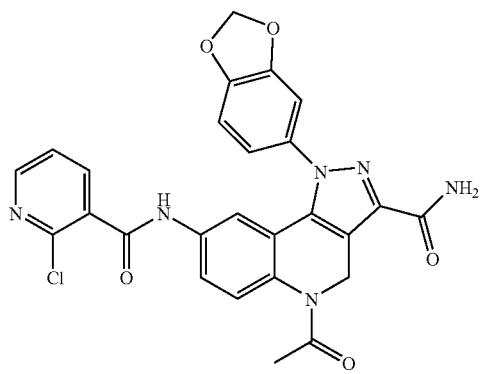

The title material of Example 17 (100 mg, 0.00025 mol) was dissolved in DMF (2 mL), and to the solution was added 2-Chloronicotinic acid (40 mg, 0.00025 mol), HATU (144 mg, 0.00038 mol), and DIEA (49 mg, 0.00038 mol). The reaction was blanketed with argon and stirred at room temperature for 18 hours. The solution was concentrated in vacuo, and the resulting solid were washed with water and then filtered. The product was then recrystallized from ethanol, and isolated by vacuum filtration. 25 mg. (MW= 530.93, 19% yield). LC/MS m/z=531.7 (m+1).

Example 22

5-acetyl-1-(1,3-benzodioxol-5-yl)-8-[(3-chloroisonicotinoyl)amino]-4,5-dihydro-1H-pyrazolo[4,3-c]quinoline-3-carboxamide

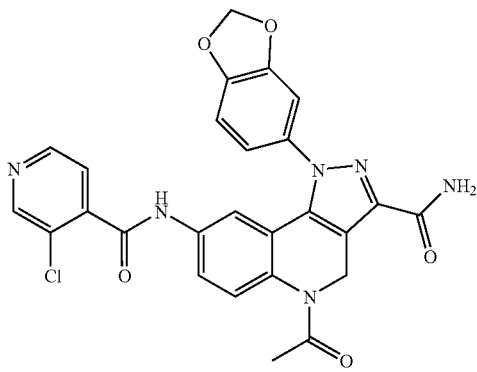

The product was obtained from the title material of Example 17 (100 mg, 0.00025 mol), 2-Chloroisonicotinic acid (40 mg, 0.00025 mol), and by the method of Example 21. 45 mg. (MW=530.93, 34% yield). LC/MS m/z=531.8 (m+1).

Example 23

5-acetyl-1-(1,3-benzodioxol-5-yl)-8-[(methylsulfonyl)amino]-4,5-dihydro-1H-pyrazolo[4,3-c]quinoline-3-carboxamide

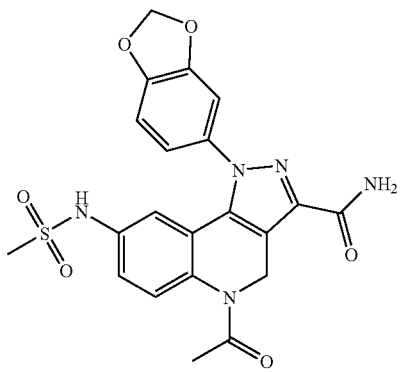

The title material from Example 17 step 6 (300 mg, 0.000767 mol) was dissolved in pyridine (5 mL), and to this solution was added methane sulfonyl chloride (88 mg, 0.000767 mol). The resulting solution was stirred at room temperature for 18 hours. The reaction was then concentrated in vacuo, and the resulting solids were triturated with water and the product was isolated by vacuum filtration. 88 mg. (MW=469.48, 25% yield). LC/MS m/z=470.3 (m+1).

Example 24

5-acetyl-8-amino-1-(4-fluorophenyl)-4,5-dihydro-1H-pyrazolo[4,3-c]quinoline-3-carboxamide

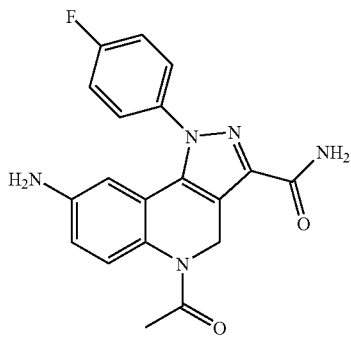

Step 1
ethyl 5-acetyl-1-(4-fluorophenyl)-8-nitro-4,5-dihydro-1H-pyrazolo[4,3-c]quinoline-3-carboxylate

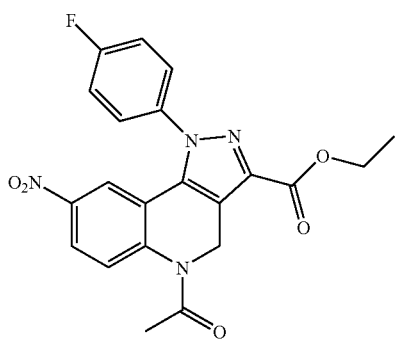

The material of step 3 of Example 17 (15 g, 0.044 mol) was dissolved in 100 mL of glacial acetic acid and then 4-fluorophenyl hydrazine hydrochloride (7.15 g, 0.044 mol) was added. The reaction was then stirred at room temperature for 18 hours, under argon, and then concentrated to remove most of the acetic acid. The remaining viscous oil was triturated with 250 mL acetonitrile. The resulting solid was isolated by vacuum filtration and dried to yield the product as an orange/pink solid. 11 g (MW=424.38, 59% yield). LC/MS m/z=425.2 (m+1).

Step 2
ethyl 5-acetyl-8-amino-1-(4-fluorophenyl)-4,5-dihydro-1H-pyrazolo[4,3-c]quinoline-3-carboxylate

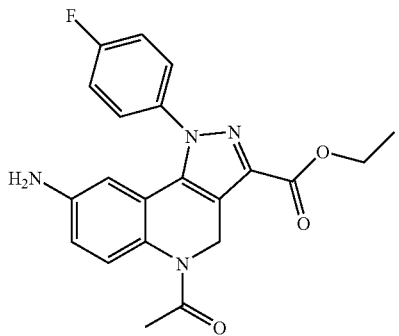

The product was obtained as the acetic acid salt from the material from step 1 (10 g, 0.0236 mol) and by the method of Example 17. 9.8 g. (FW=454.45, 91% yield). LC/MS m/z=395 (m+1).

Step 3

5-acetyl-8-amino-1-(4-fluorophenyl)-4,5-dihydro-1H-pyrazolo[4,3-c]quinoline-3-carboxamide

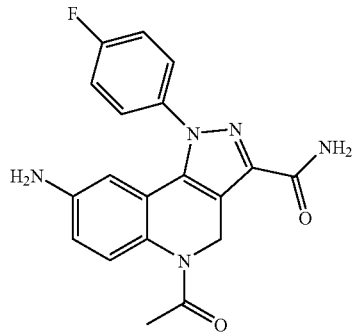

The product was obtained from the material from step 2 (9.8 g, 0.0216 mol) using the method of Example 17 step 6. 7.5 g. (MW=365.4, 95% yield). LC/MS m/z=366 (m+1).

Example 25

5-acetyl-1-(4-fluorophenyl)-8-[(methylsulfonyl)amino]-4,5-dihydro-1H-pyrazolo[4,3-c]quinoline-3-carboxamide

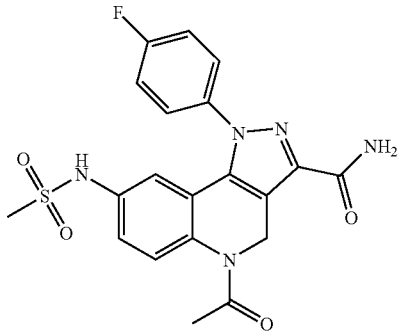

The material from step 3 of Example 24 (1 g, 0.0027 mol) was combined with methane sulfonyl chloride (345 mg, 0.003 mol) in 10 mL pyridine. The mixture was stirred at room temperature, under argon, for 3 hours. The reaction was then concentrated in vacuo. The resulting solid was washed with water and diethyl ether, and was then air dried to give the desired as a tan solid. 950 mg. (MW=443.46, 79% yield). LC/MS m/z=444 (m+1).

Example 26

5-acetyl-8-{[(2-chloropyridin-3-yl)carbonyl]amino}-1-(4-fluorophenyl)-4,5-dihydro-1H-pyrazolo[4,3-c]quinoline-3-carboxamide

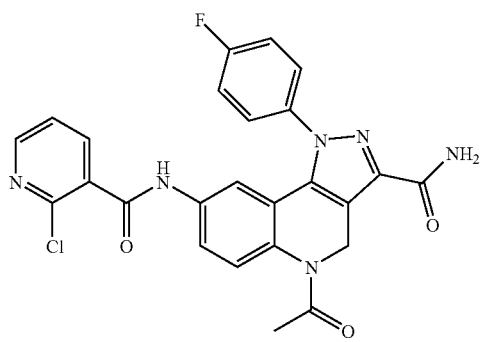

The title material from Example 24 (1.2 g, 0.0033 mol) and 2-chloro-nicotinic acid (517 mg, 0.0033 mol) were combined, under argon, in 5 mL of DMF. Diisopropyl ethyl amine (862 □L, 0.00495 mol) and HATU (1.88 g, 0.00495 mol) were added and the reaction was stirred for 18 hours at room temperature. The reaction was then concentrated in vacuo, and the resulting solids were triturated with water and isolated by vacuum filtration to give the product as an off white solid. 652 mg. (MW=504.91, 39% yield). LC/MS m/z=505.7 (m+1).

Example 27

8-{[(2-chloropyridin-3-yl)carbonyl]amino}-1-(4-fluorophenyl)-5-(methylsulfonyl)-4,5-dihydro-1H-pyrazolo[4,3-c]quinoline-3-carboxamide

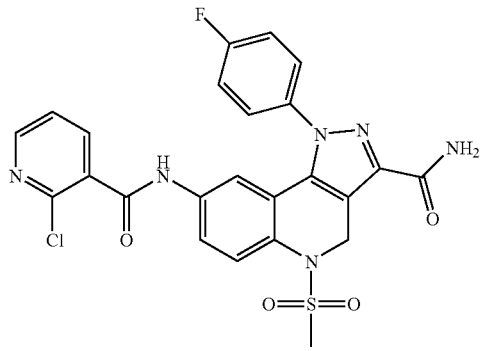

Step 1 ethyl 1-(4-fluorophenyl)-8-nitro-4,5-dihydro-1H-pyrazolo[4,3-c]quinoline-3-carboxylate

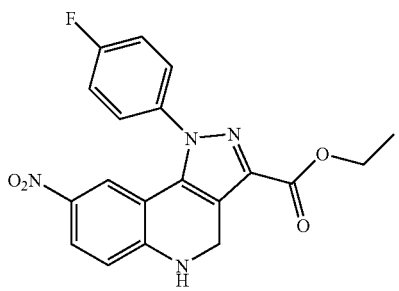

The material from step 1 of Example 24 (5 g, 0.0117 mol) was suspended in 100 mL absolute EtOH and 60 mL 1N HCl. The mixture was then heated to 80° C. for 18 hours. The heating was then terminated and the compound filtered upon cooling, to give the pure desired product as an orange solid. 3.8 g. (MW=382.35, 85% yield). LC/MS m/z=383.4 (m+1).

Step 2 ethyl 1-(4-fluorophenyl)-5-(methylsulfonyl)-8-nitro-4,5-dihydro-1H-pyrazolo[4,3-c]quinoline-3-carboxylate

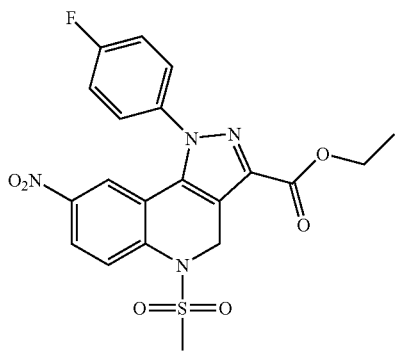

The title compound is obtained from the material of step 1, methane sulfonyl chloride, by the method of Example 25. (MW=382.35).

Step 3

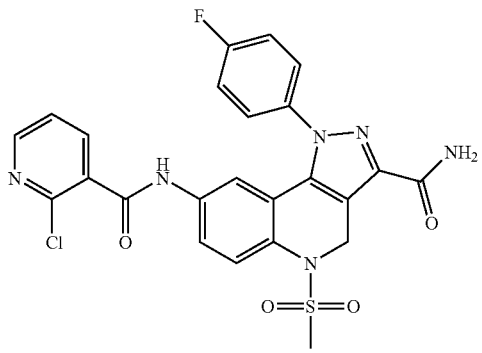

The title compound is obtained from the material of step 2, by the method of Example 21.

The structure and the bioactivity as measured in the IKK2 Resin assay of the compounds of Examples 17–27 are shown in Table 2.

TABLE 2

| Structure | Mol. Wt. | Compound Name(s) | IKK2 Resin Avg. IC50 | Example # |
|---|---|---|---|---|
| (structure shown) | 451.44 | 5-acetyl-8-amino-1-(1,3-benzodioxol-5-yl)-4,5-dihydro-1H-pyrazolo[4,3-c]quinoline-3-carboxamide acetate | ≦1 μM | Example 17 |

TABLE 2-continued

| Structure | Mol. Wt. | Compound Name(s) | IKK2 Resin Avg. IC50 | Example # |
|---|---|---|---|---|
| 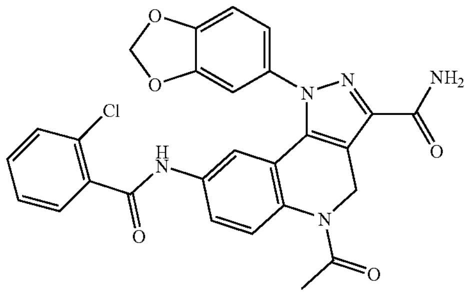 | 529.94 | 5-acetyl-1-(1,3-benzodioxol-5-yl)-8-[(2-chlorobenzoyl)amino]-4,5-dihydro-1H-pyrazolo[4,3-c]quinoline-3-carboxamide | ≦1 µM | Example 18 |
| 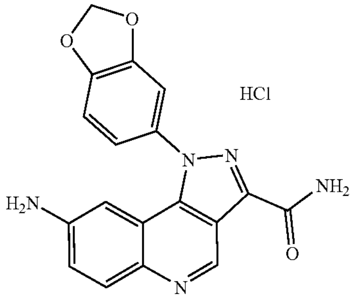 | 383.80 | 8-amino-1-(1,3-benzodioxol-5-yl)-1H-pyrazolo[4,3-c]quinoline-3-carboxamide hydrochloride | 10 ≦ 100 µM | Example 19 |
| 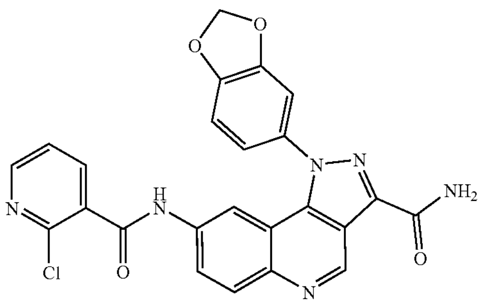 | 486.88 | 1-(1,3-benzodioxol-5-yl)-8-{[(2-chloropyridin-3-yl)carbonyl]amino}-1H-pyrazolo[4,3-c]quinoline-3-carboxamide | 1 ≦ 10 µM | Example 20 |
| | 530.93 | 5-acetyl-1-(1,3-benzodioxol-5-yl)-8-{[(2-chloropyridin-3-yl)carbonyl]amino}-4,5-dihydro-1H-pyrazolo[4,3-c]quinoline-3-carboxamide) | <1 µM | Example 21 |
| | 530.93 | 5-acetyl-1-(1,3-benzodioxol-5-yl)-8-[(3-chloroisonicotinoyl)amino]-4,5-dihydro-1H-pyrazolo[4,3-c]quinoline-3-carboxamide | <1 µM | Example 22 |

TABLE 2-continued

| Structure | Mol. Wt. | Compound Name(s) | IKK2 Resin Avg. IC50 | Example # |
|---|---|---|---|---|
| 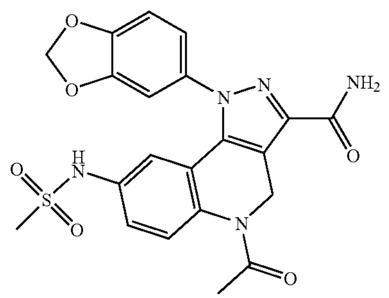 | 469.48 | 5-acetyl-1-(1,3-benzodioxol-5-yl)-8-[(methylsulfonyl)amino]-4,5-dihydro-1H-pyrazolo[4,3-c]quinoline-3-carboxamide | <1 μM | Example 23 |
| 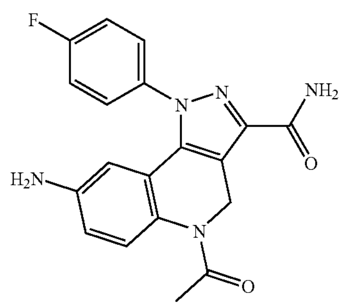 | 365.37 | 5-acetyl-8-amino-1-(4-fluorophenyl)-4,5-dihydro-1H-pyrazolo[4,3-c]quinoline-3-carboxamide | nd | Example 24 |
| 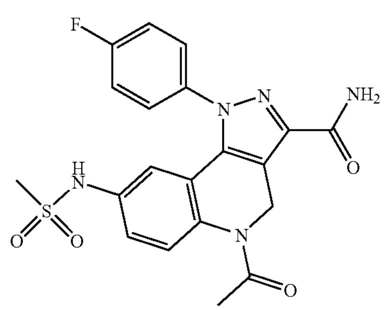 | 443.46 | 5-acetyl-1-(4-fluorophenyl)-8-[(methylsulfonyl)amino]-4,5-dihydro-1H-pyrazolo[4,3-c]quinoline-3-carboxamide | <1 μM | Example 25 |
| 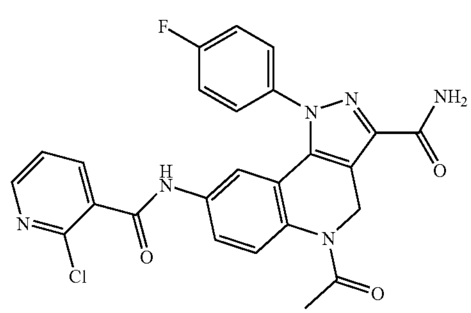 | 504.91 | 5-acetyl-8-{[(2-chloropyridin-3-yl)carbonyl]amino}-1-(4-fluorophenyl)-4,5-dihydro-1H-pyrazolo[4,3-c]quinoline-3-carboxamide | <1 μM | Example 26 |

TABLE 2-continued

| Structure | Mol. Wt. | Compound Name(s) | IKK2 Resin Avg. IC50 | Example # |
|---|---|---|---|---|
| 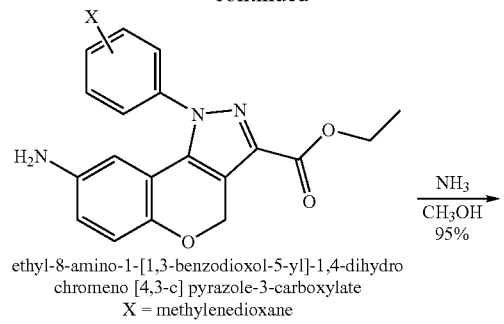 | | 8-{[(2-chloropyridin-3-yl)carbonyl]amino}-1-(4-fluorophenyl)-5-(methylsulfonyl)-4,5-dihydro-1H-pyrazolo[4,3-c]quinoline-3-carboxamide | nd | Example 27 | nd = not determined

Examples 28–46 were synthesized using the following general scheme. Examples 28, 29, and 30 are described in detail and are illustrative for the compounds of Table 3.

SCHEME XIII

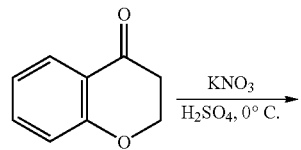

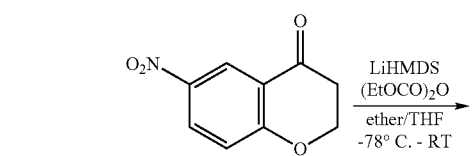

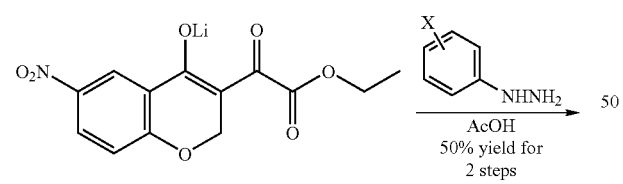

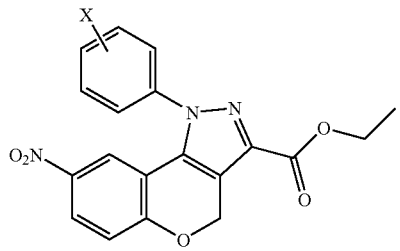

ethyl 1-[1,3-benzodioxol-5-yl]-8-nitro-1,4-dihydrochromeno [4,3-c] pyrazole-3-carboxylate
X = methylenedioxane -continued

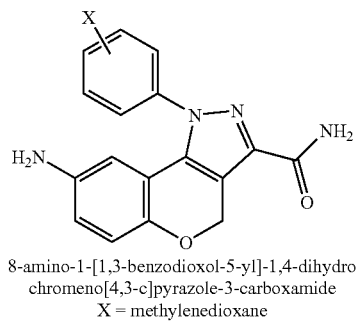

ethyl-8-amino-1-[1,3-benzodioxol-5-yl]-1,4-dihydro chromeno [4,3-c] pyrazole-3-carboxylate
X = methylenedioxane 8-amino-1-[1,3-benzodioxol-5-yl]-1,4-dihydro chromeno[4,3-c]pyrazole-3-carboxamide
X = methylenedioxane

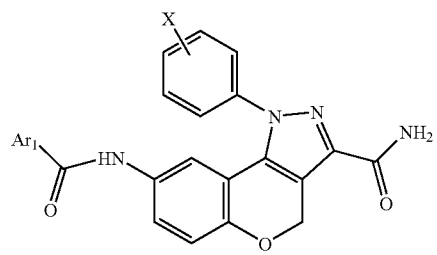

Example 28 ethyl 8-amino-1-[1,3-benzodioxol-5-yl]-1,4-dihydrochromeno[4,3-c]pyrazole-3-carboxylate

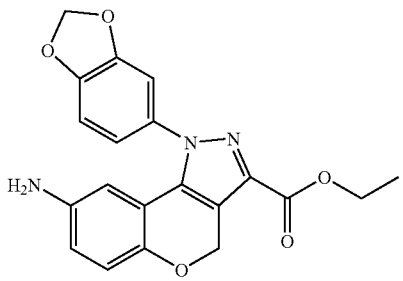

Step 1

7-nitro-4-chromanone

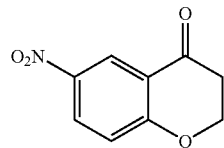

To a solution of 4-chromanone (30.0 g, 0.196 mol) in 600 mL conc. $H_2SO_4$, a solution of $KNO_3$ (21.84 g, 0.216 mol) in 400 ml conc. $H_2SO_4$ was added portionwise at 0° C. The solution was stirred for 3 h or longer at 0° C. until all starting material was consumed (the reaction was followed by LC/MS). The solution was poured slowly onto a water-ice mixture, and a white precipitate formed. The precipitate was collected by filtration, washed with water and air-dried, to give a crude mixture which contains 7-nitro-4-chromanone as the major isomer and 5-nitro-4-chromanone as a minor isomer. Recrystallization of the crude mixture from ethyl acetate/hexane gave pure 7-nitro-4-chromanone (21.08 g, 55.6%), which was characterized by $^1$H NMR, LC/MS (MH$^+$ 194) and HPLC (99% purity).

Step 2

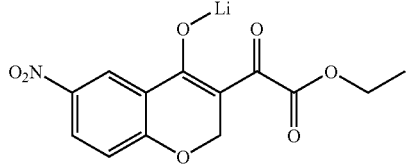

To a suspension of 7-nitro-4-chromanone from Step 1 (32 g, 0.165 mol) in dry tetrahydrofuran (750 mL) and dry ether (3L) (the tetrahydrofuran should be added first at room temperature followed by ether), diethyl oxalate (24.79 mL, 0.179 mol) was added. The resulting mixture was cooled to −30° C. followed by the addition of 1N lithium hexamethyldisilazide (185 mL, 0.185 mol) over a 2 hour period. The reaction mixture was stirred under $N_2$ and allowed to warm from −30° C. to room temperature overnight. The resulting orange color precipitate was collected by filtration and washed with ether and air dried to give desired product as the lithium salt (47 g, 99.3% yield). The product was characterized by 1H NMR, LC/MS, and HPLC.

Step 3 ethyl 1-[1,3-benzodioxol-5-yl]-8-nitro-1,4-dihydrochromeno[4,3-c]pyrazole-3-carboxylate

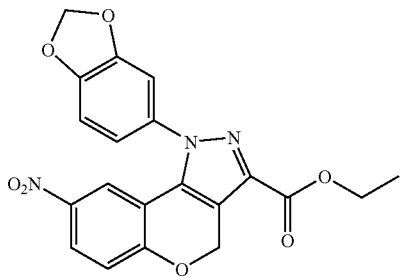

To a solution of the material from step 2 (17.72 g, 59.2977 mmol) in acetic acid (500 ml), 3,4-methylenedioxyphenyl hydrazine hydrochloride (12.2954 g, 65.2274 mmol) was added. The reaction solution was heated to reflux under $N_2$ overnight. The reaction was followed by LC/MS (usually the reaction is over in 3 to 4 hours). The reaction mixture was cooled to RT, the precipitate was collected by filtration, and washed with acetic acid (acetic acid was chased by ether), air-dried, to give desired product ethyl 1-[1,3-benzodioxol-5-yl]-8-nitro-1,4-dihydrochromeno[4,3-c]pyrazole-3-carboxylate (1$^{st}$ crop, 9.5894 g, 39.5%). The mother liquid was concentrated, and more desired product (2$^{nd}$ crop, 6.7935 g, 28.0%) was recovered by recrystallization of mother liquid. The product was characterized by $^1$H NMR, LC/MS (MH$^+$ 410), and HPLC (100% purity).

Step 4 ethyl 8-amino-1-[1,3-benzodioxol-5-yl]-1,4-dihydrochromeno[4,3-c]pyrazole-3-carboxylate

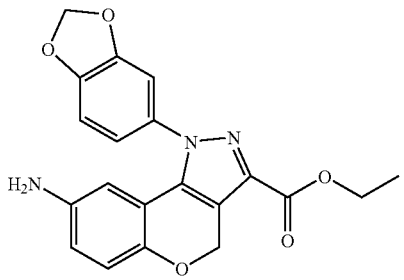

The title material from step 3 (17 g, 0.0416 mol) was treated with Raney nickel in DMF under 25 psi at RT for 17 h. The reaction mixture was filtered and washed with DMF. The combined filtrate and washes were concentrated under reduced pressure. The resulting residue was diluted with MeOH, sonicated at 40° C., the solid was collected by filtration, to give ethyl 8-amino-1-[1,3-benzodioxol-5-yl]-1,4-dihydrochromeno[4,3-c]pyrazole-3-carboxylate (12.3415 g, 78.3%). The product was characterized by $^1$H NMR, LC/MS (MH$^+$ 380), and HPLC (98% purity).

Example 29

8-amino-1-[1,3-benzodioxol-5-yl]-1,4-dihydrochromeno[4,3-c]pyrazole-3-carboxamide

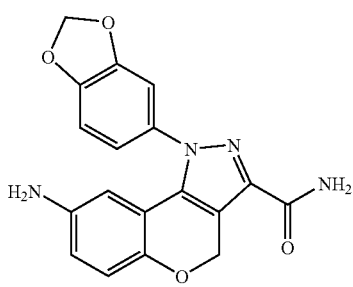

The title material from step 3 of Example 28 (11.25 g, 0.0297 mol) was treated with liquid $NH_3$ in EtOH at 120° C. under 60 psi for 20 h. The reaction solution was concentrated to dryness. The resulting solid was recrystallized with hot MeOH, to give 8-amino-1-[1,3-benzodioxo-5-yl]-1,4-dihydrochromeno[4,3-c]pyrazole-3-carboxamide (9.8842 g, 95.4%), which was characterized by $^1$H NMR, LC/MS $MH^+$ 350) and HPLC (100% purity).

Example 30
8-amino-1-[1,3-benzodioxol-5-yl]-1,4-dihydrochromeno[4,3-c]pyrazole-3-carboxamide

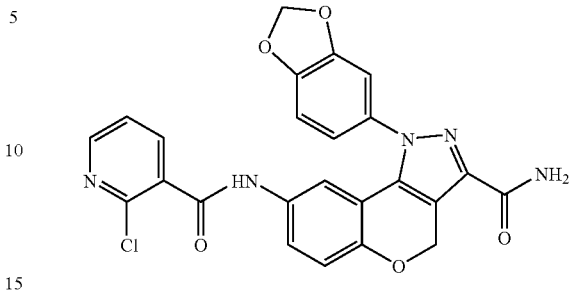

To a solution of title material from Example 28 (0.0791 g, 0.226 mmol) in dry pyridine (3 ml), 2-chloronicotinoyl chloride (0.0487 g, 0.2712 mmol) was added. The reaction was stirred at RT overnight. The reaction was quenched with PS-trisamine (4.61 mmol/g, 0.2021 g, 0.9318 mmol) and stirred overnight. The resins were filtrated, washed with pyridine. The combined filtrate and washes were concentrated to dryness. The resulting residue was recrystallized with hot methanol, to give 8-amino-1-[1,3-benzodioxol-5-yl]-1,4-dihydrochromeno[4,3-c]pyrazole-3-carboxamide (0.0922 g, 83.3%), which was characterized by $^1$H NMR, LC/MS ($MH^+$ 489), and HPLC (96.6% purity).

The structure and the bioactivity as measured in the IKK2 Resin assay of the compounds of Examples 28–62 are shown in Table 3.

TABLE 3

| Structure | Mol. Wt. | Compound Name | IKK2 Resin IC50 | Example # |
|---|---|---|---|---|
| 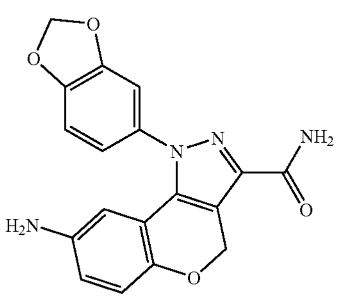 | 350.34 | 8-amino-1-(1,3-benzodioxol-5-yl)-1,4-dihydrochromeno[4,3-c]pyrazole-3-carboxamide | 1 ≦ 10 μM | Example 29 |
| 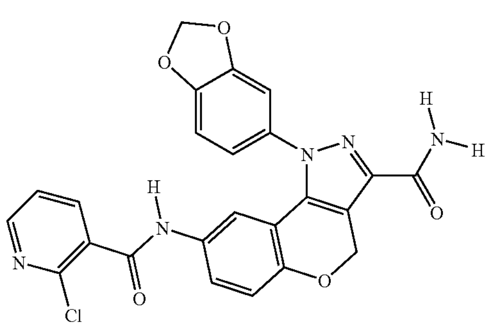 | 489.87 | 1-(1,3-benzodioxol-5-yl)-8-{[(2-chloropyridin-3-yl)carbonyl]amino}-1,4-dihydrochromeno[4,3-c]pyrazole-3-carboxamide | ≦1 μM | Example 30 |

TABLE 3-continued

| Structure | Mol. Wt. | Compound Name | IKK2 Resin IC50 | Example # |
|---|---|---|---|---|
| 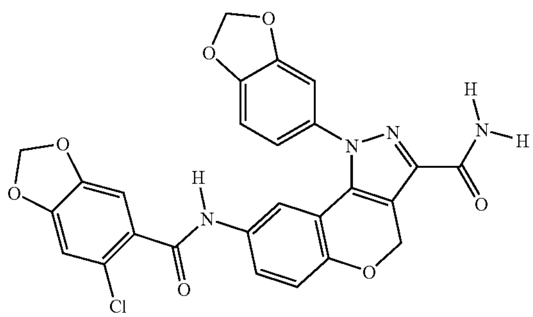 | 532.90 | 1-(1,3-benzodioxol-5-yl)-8-{[(6-chloro-1,3-benzodioxol-5-yl)carbonyl]amino}-1,4-dihydrochromeno[4,3-c]pyrazole-3-carboxamide | ≦1 μM | Example 31 |
| 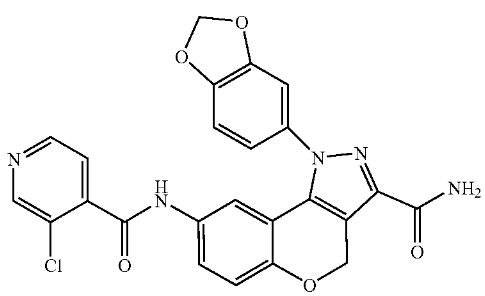 | 489.88 | 1-(1,3-benzodioxol-5-yl)-8-[(3-chloroisonicotinoyl)amino]-1,4-dihydrochromeno[4,3-c]pyrazole-3-carboxamide | ≦1 μM | Example 32 |
| 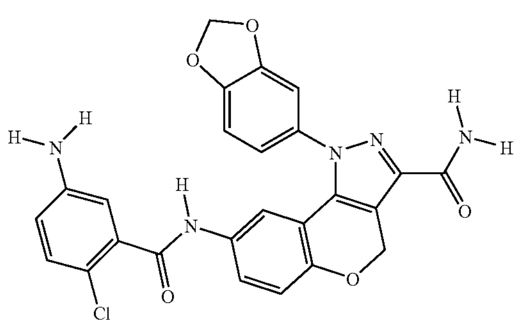 | 503.91 | 8-[(5-amino-2-chlorobenzoyl)amino]-1-(1,3-benzodioxol-5-yl)-1,4-dihydrochromeno[4,3-c]pyrazole-3-carboxamide | ≦1 μM | Example 33 |
| 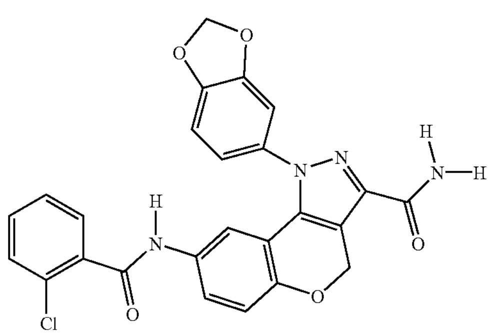 | 488.89 | 1-(1,3-benzodioxol-5-yl)-8-[(2-chlorobenzoyl)amino]-1,4-dihydrochromeno[4,3-c]pyrazole-3-carboxamide | ≦1 μM | Example 34 |

TABLE 3-continued

| Structure | Mol. Wt. | Compound Name | IKK2 Resin IC50 | Example # |
|---|---|---|---|---|
| 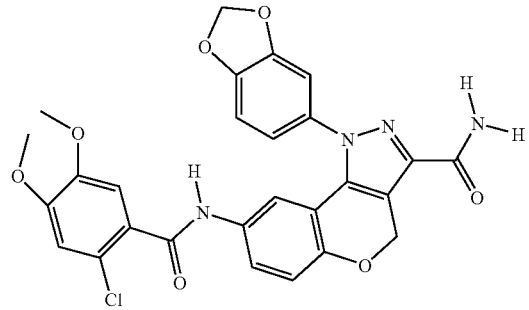 | 548.94 | 1-(1,3-benzodioxol-5-yl)-8-[(2-chloro-4,5-dimethoxybenzoyl)amino]-1,4-dihydrochromeno[4,3-c]pyrazole-3-carboxamide | 1 ≦ 10 μM | Example 35 |
| 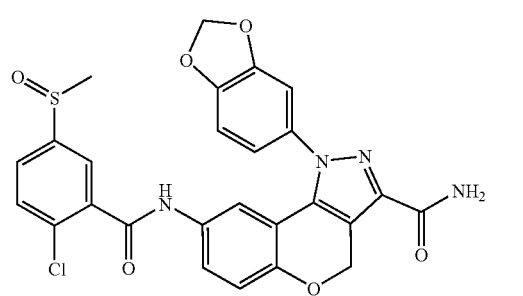 | 550.98 | 1-(1,3-benzodioxol-5-yl)-8-{[2-chloro-5-(methylsulfinyl)benzoyl]amino}-1,4-dihydrochromeno[4,3-c]pyrazole-3-carboxamide | 1 ≦ 10 μM | Example 36 |
| 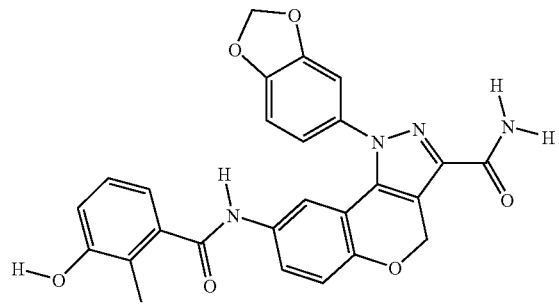 | 484.47 | 1-(1,3-benzodioxol-5-yl)-8-[(3-hydroxy-2-methylbenzoyl)amino]-1,4-dihydrochromeno[4,3-c]pyrazole-3-carboxamide | 1 ≦ 10 μM | Example 37 |
| 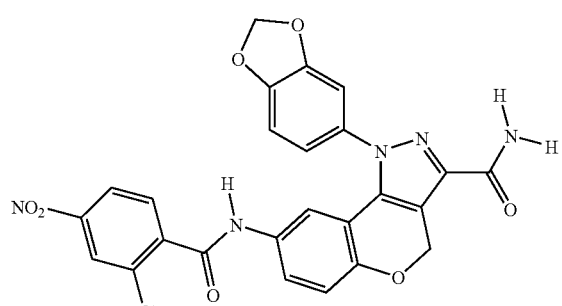 | 533.89 | 1-(1,3-benzodioxol-5-yl)-8-[(2-chloro-4-nitrobenzoyl)amino]-1,4-dihydrochromeno[4,3-c]pyrazole-3-carboxamide | 1 ≦ 10 μM | Example 38 |
| 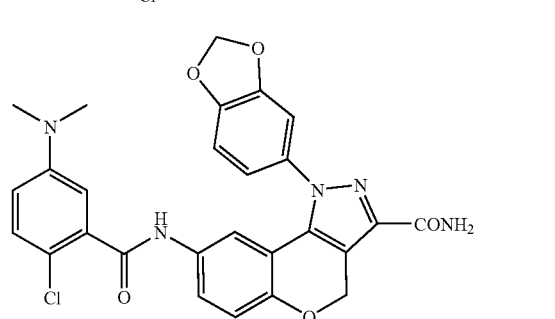 | 531.96 | 1-(1,3-benzodioxol-5-yl)-8-{[2-chloro-5-(dimethylamino)benzoyl]amino}-1,4-dihydrochromeno[4,3-c]pyrazole-3-carboxamide | 1 ≦ 10 μM | Example 39 |

TABLE 3-continued

| Structure | Mol. Wt. | Compound Name | IKK2 Resin IC50 | Example # |
|---|---|---|---|---|
| 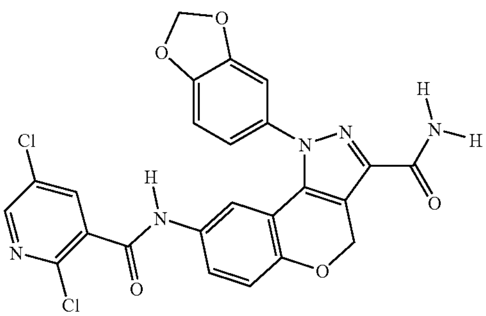 | 524.32 | 1-(1,3-benzodioxol-5-yl)-8-{[(2,5-dichloropyridin-3-yl)carbonyl]amino}-1,4-dihydrochromeno[4,3-c]pyrazole-3-carboxamide | 1 ≦ 10 μM | Example 40 |
| 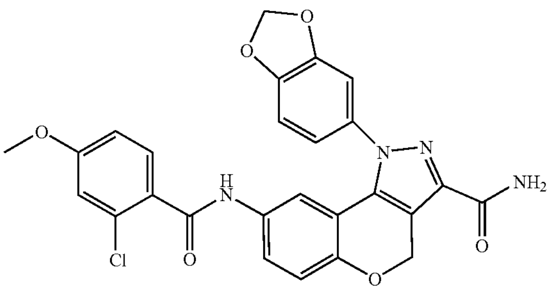 | 518.92 | 1-(1,3-benzodioxol-5-yl)-8-[(2-chloro-4-methoxybenzoyl)amino]-1,4-dihydrochromeno[4,3-c]pyrazole-3-carboxamide | 1 ≦ 10 μM | Example 41 |
| 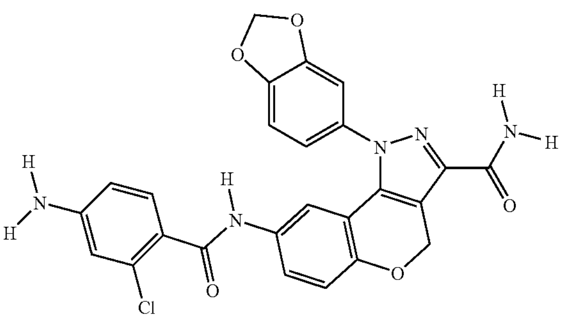 | 503.91 | 8-[(4-amino-2-chlorobenzoyl)amino]-1-(1,3-benzodioxol-5-yl)-1,4-dihydrochromeno[4,3-c]pyrazole-3-carboxamide | 1 ≦ 10 μM | Example 42 |
| 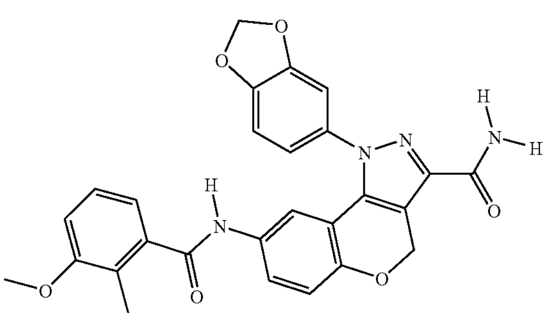 | 498.50 | 1-(1,3-benzodioxol-5-yl)-8-[(3-methoxy-2-methylbenzoyl)amino]-1,4-dihydrochromeno[4,3-c]pyrazole-3-carboxamide | 10 ≦ 100 μM | Example 43 |

TABLE 3-continued

| Structure | Mol. Wt. | Compound Name | IKK2 Resin IC50 | Example # |
|---|---|---|---|---|
| 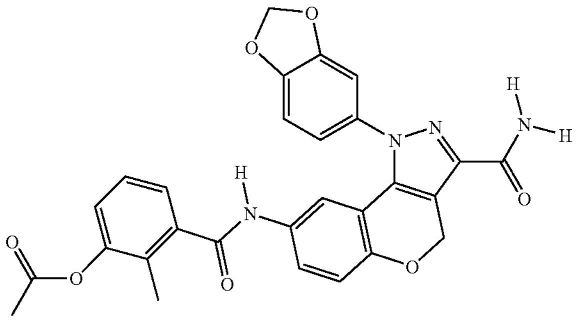 | 526.51 | 3-({[3-(aminocarbonyl)-1-(1,3-benzodioxol-5-yl)-1,4-dihydrochromeno[4,3-c]pyrazol-8-yl]amino}carbonyl)-2-methylphenyl acetate | 10 ≦ 100 μM | Example 44 |
| 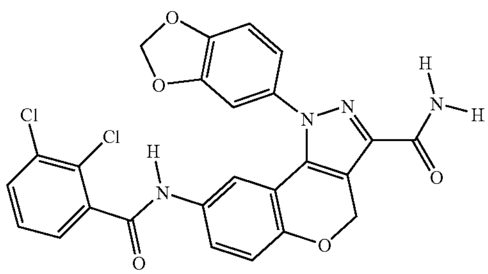 | 523.33 | 1-(1,3-benzodioxol-5-yl)-8-[(2,3-dichlorobenzoyl)amino]-1,4-dihydrochromenol[4,3-c]pyrazole-3-carboxamide | ≧100 μM | Example 45 |
| 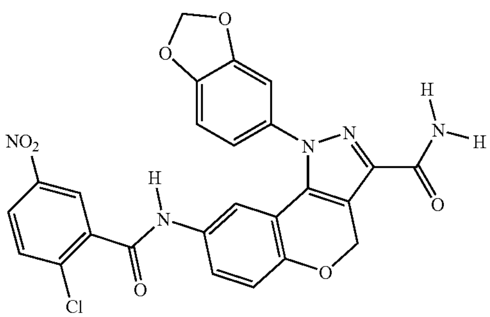 | 533.89 | 1-(1,3-benzodioxol-5-yl)-8-[(2-chloro-5-nitrobenzoyl)ammo]-1,4-dihydrochromeno[4,3-c]pyrazole-3-carboxamide | nd | Example 46 |

Examples 47–53 were synthesized in a similar manner by scheme XIII as described in Examples 28–30 where X is fluoro. The structure and the bioactivity as measured in the IKK2 Resin assay of the compounds of Examples 47–53 are shown in Table 4.

TABLE 4

| Structure | Mol. Wt. | Compound Name | IKK2 Resin IC50 | Example # |
|---|---|---|---|---|
| 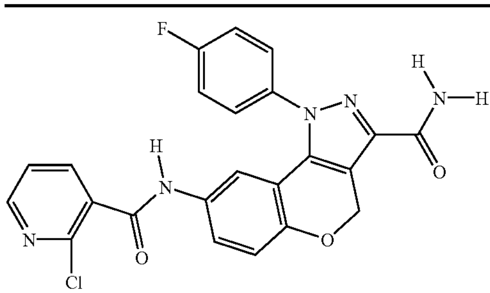 | 463.85 | 8-{[(2-chloropyridin-3-yl)carbonyl]amino}-1-(4-fluorophenyl)-1,4-dihydrochromenol[4,3-c]pyrazole-3-carboxamide | ≦1 μM | Example 47 |

TABLE 4-continued

| Structure | Mol. Wt. | Compound Name | IKK2 Resin IC50 | Example # |
|---|---|---|---|---|
| 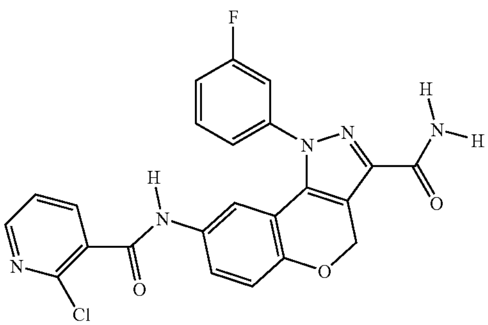 | 463.85 | 8-{[(2-chloropyridin-3-yl)carbonyl]amino}-1-(3-fluorophenyl)-1,4-dihydrochromeno[4,3-c]pyrazole-3-carboxamide | ≦1 μM | Example 48 |
| | 462.87 | 8-[(2-chlorobenzoyl)amino]-1-(4-fluorophenyl)-1,4-dihydrochromeno[4,3-c]pyrazole-3-carboxamide | 1 ≦ 10 μM | Example 49 |
| | 462.87 | 8-[(2-chlorobenzoyl)amino]-1-(3-fluorophenyl)-1,4-dihydrochromeno[4,3-c]pyrazole-3-carboxamide | 10 ≦ 100 μM | Example 50 |
| 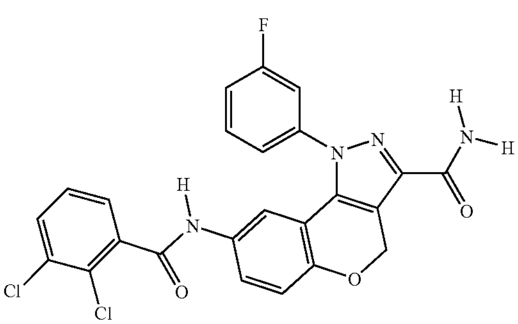 | 497.31 | 8-[(2,3-dichlorobenzoyl)amino]-1-(3-fluorophenyl)-1,4-dihydrochromeno[4,3-c]pyrazole-3-carboxamide | 10 ≦ 100 μM | Example 51 |
| 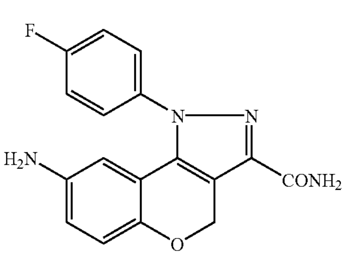 | 324.32 | 8-amino-1-(4-fluorophenyl)-1,4-dihydrochromeno[4,3-c]pyrazole-3-carboxamide | nd | Example 52 |

TABLE 4-continued

| Structure | Mol. Wt. | Compound Name | IKK2 Resin IC50 | Example # |
|---|---|---|---|---|
| 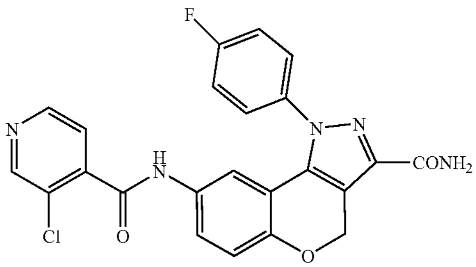 | 463.85 | 8-[(3-chloroisonicotinoyl)amino]-1-(4-fluorophenyl)-1,4-dihydrochromeno[4,3-c]pyrazole-3-carboxamide | <1 µM | Example 53 |

Examples 54–58 were synthesized in a similar manner by scheme XIII as described in Examples 28–30 where X is methylsulfonyl, methylsulfinyl, or methylthio. The structure and the bioactivity as measured in the IKK2 Resin assay of the compounds of Examples 54–58 are shown in Table 5.

TABLE 5

| Structure | Mol. Wt. | Compound Name IC50 | IKK2 Resin | Example # |
|---|---|---|---|---|
| 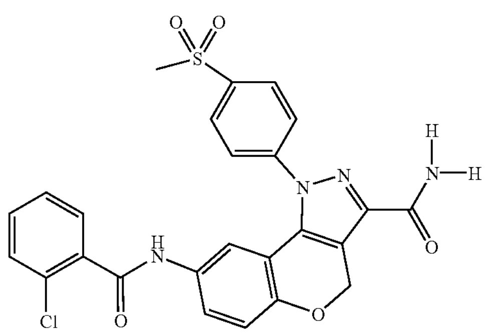 | 522.97 | 8-[(2-chlorobenzoyl)amino]-1-[4-(methylsulfonyl)phenyl]-1,4-dihydrochromeno[4,3-c]pyrazole-3-carboxamide | ≦1 µM | Example 54 |
| 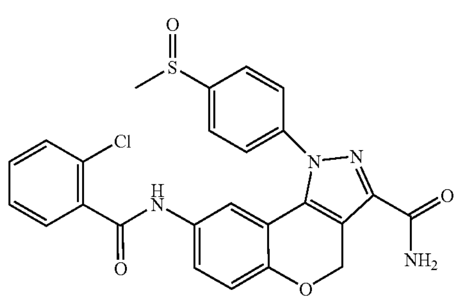 | 506.97 | 8-[(2-chlorobenzoyl)amino]-1-[4-(methylsulfinyl)phenyl]-1,4-dihydrochromeno[4,3-c]pyrazole-3-carboxamide | 1 ≦ µM | Example 55 |
| 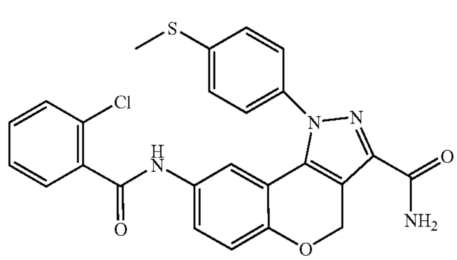 | 490.97 | 8-[(2-chlorobenzoyl)amino]-1-[4-(methylthio)phenyl]-1,4-dihydrochromeno[4,3-c]pyrazole-3-carboxamide | 10 ≦ 100 µM | Example 56 |

TABLE 5-continued

| Structure | Mol. Wt. | Compound Name | IC50 | IKK2 Resin Example # |
|---|---|---|---|---|
| 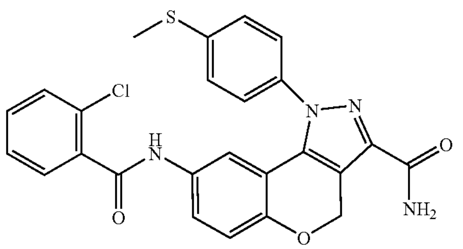 | 490.97 | 8-[(2-chlorobenzoyl)amino]-1-[4-(methylthio)phenyl]-1,4-dihydrochromeno[4,3-c]pyrazole-3-carboxamide) | 10 ≦ μM | Example 57 |
| 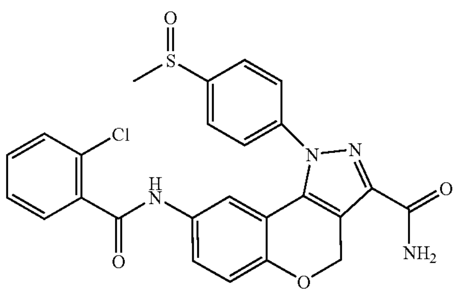 | 506.97 | 8-[(2-chlorobenzoyl)amino]-1-[4-(methylsulfinyl)phenyl]-1,4-dihydrochromeno[4,3-c]pyrazole-3-carboxamide | 1 ≦ 10 μM | Example 58 |

Biological Evaluation

Materials

SAM[2™] 96 Biotin capture plates were from Promega. Anti-FLAG affinity resin, FLAG-peptide, NP-40 (Nonidet P-40), BSA, ATP, ADP, AMP, LPS (*E. coli* serotype 0111:B4), and dithiothreitol were obtained from Sigma Chemicals. Antibodies specific for NEMO (IKKγ) (FL-419), IKK1(H-744), IKK2(H-470) and IκBα(C-21) were purchased from Santa Cruz Biotechnology. Ni-NTA resin was purchased from Qiagen. Peptides were purchased from American Peptide Company. Protease inhibitor cocktail tablets were from Boehringer Mannheim. Sephacryl S-300 column was from Pharmacia LKB Biotechnology. Centriprep-10 concentrators with a molecular weight cutoff of 10 kDa and membranes with molecular weight cut-off of 30 kDa were obtained from Amicon. [γ-$^{33}$P] ATP (2500 Ci/mmol) and [γ-$^{32}$P] ATP (6000 Ci/mmol) were purchased from Amersham. The other reagents used were of the highest grade commercially available.

Cloning and Expression cDNAs of human IKK1 and IKK2 were amplified by reverse transcriptase-polymerase chain reaction from human placental RNA (Clonetech). hIKK1 was subcloned into pFastBac HTa (Life Technologies) and expressed as N-terminal His$_6$-tagged fusion protein. The hIKK2 cDNA was amplified using a reverse oligonucleotide primer which incorporated the peptide sequence for a FLAG-epitope tag at the C-terminus of the IKK2 coding region (DYKDDDDKD). The hIKK2:FLAG cDNA was subcloned into the baculovirus vector pFastBac. The rhIKK2 (S177S, E177E) mutant was constructed in the same vector used for wild type rhIKK2 using a QuikChange™ mutagenesis kit (Stratagene). Viral stocks of each construct were used to infect insect cells grown in 40L suspension culture. The cells were lysed at a time that maximal expression and rhIKK activity were demonstrated. Cell lysates were stored at −80° C. until purification of the recombinant proteins was undertaken as described below.

Enzyme Isolation

All purification procedures were carried out at 4° C. unless otherwise noted. Buffers used are: buffer A: 20 mM Tris-HCl, pH 7.6, containing 50 mM NaCl, 20 mM NaF, 20 mM β-Glycerophosphate, 500 uM sodiumortho-vanadate, 2.5 mM metabisulfite, 5 mM benzamidine, 1 mM EDTA, 0.5 mM EGTA, 10% glycerol, 1 mM DTT, 1×Complete™ protease inhibitors; buffer B: same as buffer A, except 150 mM NaCl, and buffer C: same as buffer A, except 500 mM NaCl.

Isolation of rhIKK1 Homodimer

Cells from an 8 liter fermentation of baculovirus-expressed IKK1 tagged with His peptide were centrifuged and the cell pellet (MOI 0.1, I=72 hr) was re-suspended in 100 ml of buffer C. The cells were microfluidized and centrifuged at 100,000×g for 45 min. The supernatant was collected, imidazole added to the final concentration of 10 mM and incubated with 25 ml of Ni-NTA resin for 2 hrs. The suspension was poured into a 25 ml column and washed with 250 ml of buffer C and then with 125 ml of 50 mM imidazole in buffer C. rhIKK1 homodimer was eluted using 300 mM imidazole in buffer C. BSA and NP-40 were added to the enzyme fractions to the final concentration of 0.1%. The enzyme was dialyzed against buffer B, aliquoted and stored at −80° C.

Isolation of rhIKK2 Homodimer

A 10 liter culture of baculovirus-expressing IKK2 tagged with FLAG peptide was centrifuged and the cell pellet (MOI=0.1 and I=72 hrs) was re-suspended in buffer A. These cells were microfluidized, and centrifuged at 100,000×g for 45 min. Supernatant was passed over a G-25 column equilibrated with Buffer A. Protein peak was collected and incubated with anti-FLAG affinity resin on a rotator overnight in buffer B. The resin was washed in batch with 10–15 bed volumes of buffer C. Washed resin was poured into a column and rhIKK2 homodimer was eluted using 5 bed volumes of buffer B containing FLAG peptide. 5 mM DTT, 0.1% NP-40 and BSA (concentrated to 0.1% in final amount) was added to the eluted enzyme before concentrating in using an Amicon membrane with a molecular weight cut-off of 30 kDa. Enzyme was aliquoted and stored at −80° C.

Isolation of rhIKK1/IKK2 Heterodimer

The heterodimer enzyme was produced by coinfection in a baculovirus system (FLAG IKK2/IKK1 His; MOI=0.1 and I=72 hrs). Infected cells were centrifuged and the cell pellet (10.0 g) was suspended in 50 ml of buffer A. The protein suspension was microfluidized and centrifuged at 100,000×g for 45 min. Imidazole was added to the supernatant to a final concentration of 10 mM. The protein was allowed to bind 25 ml of Ni-NTA resin by mixing for 2 hrs. The protein-resin slurry was poured into a 25 ml column and washed with 250 ml of buffer A containing 10 mM imidazole followed by 125 ml of buffer A containing 50 mM imidazole. Buffer A, containing 300 mM imidazole, was then used to elute the protein. A 75 ml pool was collected and NP-40 was added to a final concentration of 0.1%. The protein solution was then dialyzed against buffer B. The dialyzed heterodimer enzyme was then allowed to bind to 25 ml of anti-FLAG M2 agarose affinity gel overnight with constant mixing. The protein-resin slurry was then centrifuged for 5 min at 2,000 rpm. The supernatant was collected and the resin re-suspended in 100 ml of buffer C containing 0.1% NP-40. The resin was washed with 375 ml of buffer C containing 0.1% NP-40. The protein-resin was poured into a 25 ml column and the enzyme eluted using buffer B containing FLAG peptide. Enzyme fractions (100 ml) were collected and concentrated to 20 ml using an Amicon membrane with molecular weight cut-off of 30 kDa. Bovine serum albumin was added to the concentrated enzyme to final concentration of 0.1%. The enzyme was then aliquoted and stored at −80° C.

Cell Culture

The wild type (wt) human pre-B cell line, 70Z/3, and its mutant, 1.3E2, were generously provided by Dr. Carol Sibley. Wt 70Z/3 and 1.3E2 cells were grown in RPMI 1640 (Gibco) supplemented with 7% defined bovine serum (Hyclone) and 50 μM 2-mercaptoethanol. Human monocytic leukemia THP-1 cells, obtained from ATCC, were cultured in RPMI 1640 supplemented with 10% defined bovine serum, 10 mM HEPES, 1.0 mM sodium pyruvate and 50 μM 2-mercaptoethanol. For experiments, cells were plated in 6 well plates at $1 \times 10^6$ cells/ml in fresh media. Pre-B cells were stimulated by the addition of 10 μg/ml LPS for varying lengths of time ranging from 0–4 hr. THP-1 cells were stimulated by the addition of 1 μg/ml LPS for 45 minutes. Cells were pelleted, washed with cold 50 mM sodium phosphate buffer, pH 7.4 containing 0.15 M NaCl and lysed at 4° C. in 20 mM Hepes buffer, pH 7.6 containing 50 mM NaCl, 1 mM EDTA, 1 mM EGTA, 1 mM sodium orthovanadate, 10 mM β-glycerophosphate, 1 mM NaF, 1 mM PMSF, 1 mM DTT and 0.5% NP40 (lysis buffer). The cytosolic fractions obtained following centrifagation at 10,000×g were stored at −80° C. until used.

Immunoprecipitation and Western Blotting

SF9 cells paste containing rhIKKs were centrifuged (100,000×g, 10 min) to remove debris. rhIKKs were immunoprecipitated (100 μg of cell paste) from the cell supernatant using 3 μg of anti-NEMO antibody (FL-419), followed by coupling to protein A sepharose beads. rhIKKs were also immunoprecipitated from affinity chromatography purified protein preparations (1 μg) using anti-FLAG, anti-His or anti-NEMO antibodies (1–4 μg) followed by protein A sepharose coupling. The native, human IKK complex was immunoprecipitated from THP-1 cell homogenates (300 μg/condition) using the anti-NEMO antibody. Immune complexes were pelleted and washed 3 times with 1 ml cold lysis buffer. Immunoprecipitated rhIKKs were chromatographed by SDS-PAGE (8% Tris-glycine) and transferred to nitrocellulose membranes (Novex) and detected by chemiluminescence (SuperSignal) using specific anti-IKK antibodies (IKK2H-470, IKK1H-744). Native IKK2, IκBα and NEMO proteins from cytosolic lysates (20–80 μg) were separated by SDS-PAGE and visualized by chemiluminescense using specific antibodies.

Phosphatase Treatment

Immunoprecipitated rhIKKs were washed 2 times in 50 mM Tris-HCl, pH 8.2 containing 0.1 mM EDTA, 1 mM DTT, 1 mM PMSF and 2 mM $MnCl_2$ and resuspended in 50 μl. Phosphatase (λPPase, 1000 U) was pre-diluted in the same buffer and added to the IKK samples. Following an incubation at room temperature for 30 minutes with intermittent mixing, cold lysis buffer was added to the tubes to stop the reaction. After several washes, 10% of the beads were removed for Western analysis, and the remaining material was pelleted and resuspended in 100 μl of the buffer used for the in vitro kinase assay.

IKKα SAM Enzyme Assay

IKKα kinase activity was measured using a biotinylated IκBα peptide (Gly-Leu-Lys-Lys-Glu-Arg-Leu-Leu-Asp-Asp-Arg-His-Asp-Ser$_{32}$-Gly-Leu-Asp-Ser$_{36}$-Met-Lys-Asp-Glu-Glu), a SAM$^{2TM}$ 96 Biotin capture plate, and a vacuum system. The standard reaction mixture contained 5 μM biotinylated IκBα peptide, 1 μM [γ-$^{33}$P] ATP (about $1 \times 10^5$ cpm), 1 mM DTT, 50 mM KCl, 2 mM $MgCl_2$, 2 mM $MnCl_2$, 10 mM NaF, 25 mM Hepes buffer, pH. 7.6 and enzyme solution (1–10 μl) in a final volume of 50 μl. After incubation at 25° C. for 30 min, 25 μl of the reaction mixture was withdrawn and added to a SAM$^{2TM}$ 96 Biotin capture 96-well plate. Each well was then washed successively with 800 μl 2 M NaCl, 1.2 ml of NaCl containing 1% $H_3PO_4$, 400 μl $H_2O$, and 200 μl 95% ethanol. The plate was allowed to dry in a hood at 25° C. for 1 hr and then 25 μl of scintillation fluid (Microscint 20) was added to each well. Incorporation of [γ-$^{33}$P] ATP was measured using a Top-Count NXT (Packard). Under each assay condition, the degree of phosphorylation of IκBα peptide substrate was linear with time and concentration for all purified enzymes. Results from the biotinylated peptide assay were confirmed by SDS-PAGE analysis of kinase reaction utilizing a GST-IκBα$_{1-54}$ and [γ-$^{32}$P] ATP. The resulting radiolabeled substrate was quantitated by Phosphoimager (Molecular Dynamics). An ion exchange resin assay was also employed using [γ-$^{33}$P] ATP and GST-IκBα$_{1-54}$ fusion protein as the substrates. Each assay system yielded consistent results in regard to $K_m$ and specific activities for each of the purified kinase isoforms. One unit of enzyme activity was defined as the amount required to catalyze the transfer of 1 nmole of phosphate from ATP to IκBα peptide per min. Specific activity was expressed as units per mg of protein. For experiments related to $K_m$ determination of purified enzymes, various concentrations of ATP or IκBα peptide were used in the assay at either a fixed IκBα or ATP concentration. For IκBα peptide $K_m$, assays were carried out with 0.1 μg of enzyme, 5 μM ATP and IκBα peptide from 0.5 to 20 μM. For ATP $K_m$, assays were carried out with 0.1 μg of enzyme, 10 μM IκBα peptide and ATP from 0.1 to 10 μM. For $K_m$ determination of rhIKK1 homodimer, due to its low activity and higher $K_m$ for IκBα peptide, rhIKK1 homodimer (0.3 μg) was assayed with 125 μM IκBα peptide and a 5-fold higher specific activity of ATP (from 0.1 to 10 μM) for ATP $K_m$ experiments and a 5-fold higher specific activity of 5 μM ATP and IκBα peptide (from 5 to 200 μM) for IκBα peptide $K_m$ experiments.

IKKβ Resin Enzyme Assay

IKKβ kinase activity was measured using a biotinylated IκBα peptide (Gly-Leu-Lys-Lys-Glu-Arg-Leu-Leu-Asp-Asp-Arg-His-Asp-Ser$_{32}$-Gly-Leu-Asp-Ser$_{36}$-Met-Lys-Asp-Glu-Glu) (American Peptide Co.). 20 ul of the standard reaction mixture contained 5 µM biotinylated IκBα peptide, 0.1 µCi/reaction [γ-$^{33}$P] ATP (Amersham) (about 1×10$^5$ cpm), 1 µM ATP (Sigma), 1 mM DTT (Sigma), 2 mM MgCl$_2$ (Sigma), 2 mM MnCl$_2$ (Sigma), 10 mM NaF (Sigma), 25 mM Hepes (Sigma) buffer, pH 7.6 and 20 µl enzyme solution and 10 ul inhibitor in a final volume of 50 µl. After incubation at 25° C. for 30 min, 150 µl resin (Dowex anion-exchange resin AG1X8 200–400 mesh) in 900 mM formate, pH 3.0 was added to each well to stop the reaction. Resin was allowed to settle for one hour and 50 ul of supernatant was removed to a Micolite-2 flat bottom plate (Dynex). 150 µl of scintillation fluid (Microscint 40) (Packard) was added to each well. Incorporation of [γ-$^{33}$P] ATP was measured using a Top-Count NXT (Packard).

IKK Heterodimer Resin Enzyme Assay

IKK heterodimer kinase activity was measured using a biotinylated IκBα peptide (Gly-Leu-Lys-Lys-Glu-Arg-Leu-Leu-Asp-Asp-Arg-His-Asp-Ser$_{32}$-Gly-Leu-Asp-Ser$_{36}$-Met-Lys-Asp-Glu-Glu) (American Peptide Co.). 20 ul of the standard reaction mixture contained 5 µM biotinylated IκBα peptide, 0.1 µCi/reaction [γ-$^{33}$P] ATP (Amersham) (about 1×10$^5$ cpm), 1 µM ATP (Sigma), 1 mM DTT (Sigma), 2 mM MgCl$_2$ (Sigma), 2 mM MnCl$_2$ (Sigma), 10 mM NaF (Sigma), 25 mM Hepes (Sigma) buffer, pH 7.6 and 20 µl enzyme solution and 10 µl inhibitor in a final volume of 50 µl. After incubation at 25° C. for 30 min, 150 µl resin (Dowex anion-exchange resin AG1X8 200–400 mesh) in 900 mM formate, pH 3.0 was added to each well to stop the reaction. Resin was allowed to settle for one hour and 50 ul of supernatant was removed to a Micolite-2 flat bottom plate (Dynex). 150 µl of scintillation fluid (Microscint 40) (Packard) was added to each well. Incorporation of [γ-$^{33}$P] ATP was measured using a Top-Count NXT (Packard).

What is claimed is:

1. A compound of Formula I:

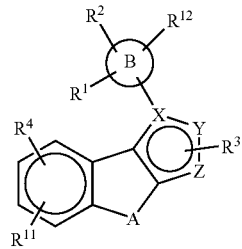

wherein

A is —O—CH$_2$— or —CH$_2$—S—, wherein each CH$_2$ may be independently substituted with one or more substitution selected from the group consisting of: hydroxy, halo, alkoxy, lower alkyl, amino, aminoalkyl, alkylamino, alkenyl, and alkynyl;

B is a 5 or 6 membered heteroaryl, or aryl, optionally saturated, or optionally substituted with $R^1$, $R^2$, or $R^{12}$;

X is N;

Y is N;

Z is C;

$R^1$ is selected from the group consisting of: hydrido, halogen, alkyl, aryl, heteroaryl, alkenyl, alkynyl, haloalkyl, CN, NO$_2$, OR$^5$, OCOOR$^5$, CO$_2$R$^7$, CON(R$^6$) R$^7$, COR$^6$, SR$^6$, SOR$^6$, SO$_2$R$^6$, NR$^6$R$^7$, NR$^6$COR$^7$, NR$^6$CONHR$_7$, NR$^6$SO$_2$R$^7$, NR$^6$SO$_2$NHR$^7$, and SO$_2$N (R$^6$)R$^7$ wherein R$^6$ and R$^7$ may be taken together to form a 3–7 membered carbocyclic ring having 1 to 3 substituted or unsubstituted heteroatoms selected from the group consisting of: S, SO, SO$_2$, O, and NR$^6$; wherein said alkenyl, alkynyl, alkyl, aryl, heteroaryl or OR$^5$ are optional substituted with, hydrido, halogen, alkyl, hydroxyalkyl, aryl, heteroaryl, haloalkyl, COCF$_3$, CN, NO$_2$, OR$^5$, OCOOR$^5$, CO$_2$R$^7$, CON(R$^6$) R$^7$, COR$^6$, SR$^6$, SOR$^6$, SO$_2$R$^6$, NR$^6$R$^7$, NR$^6$COR$^7$, NR$^6$CONHR$^7$, NR$^6$SO$_2$R$^7$, NR$^6$SO$_2$NHR$^7$, and SO$_2$N (R$^6$)R$^7$ wherein R$^6$ R$^7$ may be taken together to form a 3–7 membered carbocyclic ring having 1 to 3 substituted or unsubstituted heteroatoms selected from the group consisting of: S, SO, SO$_2$, O, and NR$^6$;

$R^2$ is selected from the group consisting of: halogen, hydrido, hydroxyalkyl, alkyl, OR$^6$, CN, NO$_2$, SR$^6$, NHR$^6$, CON(R$^6$)R$^7$, NHCONHR$^6$, CO$_2$H, and haloalkyl;

$R^1$ and $R^2$ may be taken together to form a 5 to 7 membered saturated or unsaturated carbocyclic ring optionally containing 0 to 3 heteroatoms selected from the group consisting of: N, O, or S, and wherein said ring is optionally substituted with $R^1$;

$R^3$ is selected from the group consisting of: substituted or unsubstituted amidine, alkylamino, aminoalkyl, CONHR$^{16}$, NH$_2$, NHCOR$^6$, and CH$_2$NHCOR$^6$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR$^{13}$, SR$^8$, SO$_2$N(R$^8$)R$^{8\prime}$, NHR$^9$, NHCOR$^9$, NR$^9$COR$^9$, NHCO(OR$^9$), NR$^9$CO(OR$^9$), NR$^8$SO$_2$R$^{10}$, NHSO$_2$N(R$^{10}$)R$^{10\prime}$, NR$^6$CON(R$^{10}$)R$^{10\prime}$, COR$^9$, CO$_2$R$^8$, CON(R$^8$)R$^{8\prime}$, wherein R$^8$ and R$^{8\prime}$ may be taken together to form a 3–7 membered carbocyclic ring having 1 to 3 substituted or unsubstituted heteroatoms selected from S, SO, SO$_2$, O, N, and NR$^6$, and wherein R$^{10}$ and R$^{10\prime}$ may be taken together to form a 3–7 membered carbocyclic ring having 1 to 3 substituted or unsubstituted heteroatoms selected from S, SO, SO$_2$, O, N, and NR$^6$ wherein said aryl, heterocyclic, heteroaryl, or alkenyl are optionally substituted with R$^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: OR$^{14}$, N(R$^{14}$)R$^{14\prime}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heteroclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is selected from the group consisting of: hydrido, halogen, alkyl, and alkoxy;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^{14}$ is independently selected from the group consisting of: hydrido, and lower alkyl;

$R^{14'}$ is independently selected from the group consisting of: hydrido, and lower alkyl; and $R^{16}$ is independently selected from the group consisting of: hydrido, aryl, lower alkyl, haloalkyl, alkenyl, alkynyl, hydroxyalkyl, aminoalkyl, alkoxy, and alkoxyalkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, esters, prodrugs, or pharmaceutically acceptable salts thereof.

2. A compound of Formula II:

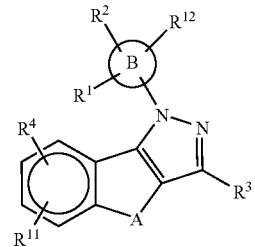

wherein

A is —O—$CH_2$— or —$CH_2$—S—, wherein each $CH_2$ may be independently substituted with one or more substitution selected from the group consisting of: hydroxy, halo, alkoxy, lower alkyl, amino, aminoalkyl, alkylamino, alkenyl, and alkynyl;

B is a 5 or 6 membered heteroaryl, or aryl, optionally saturated, or optionally substituted with $R^1$, $R^2$, or $R^{12}$;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is selected from the group consisting of: halogen, hydrido, hydroxyalkyl, alkyl, $OR^6$, CN, $NO_2$, $SR^6$, $NHR^6$, $CON(R^6)R^7$, $NHCONHR^6$, $CO_2H$, and haloalkyl;

$R^1$ and $R^2$ may be taken together to form a 5 to 7 membered saturated or unsaturated carbocyclic ring optionally containing 0 to 3 heteroatoms selected from the group consisting of: N, O, or S, and wherein said ring is optionally substituted with $R^1$;

$R^3$ is selected from the group consisting of: substituted or unsubstituted amidine, alkylamino, aminoalkyl, $CONHR^{16}$, $NH_2$, $NHCOR^6$, and $CH_2NHCOR^6$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10\prime}$, $NR^6CON(R^{10})R^{10\prime}$, $COR^9$, $CO_2R^8$, $CON(R^8)R^{8\prime}$, wherein $R^8$ and $R^{8\prime}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10\prime}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14\prime}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8\prime}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10\prime}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is selected from the group consisting of: hydrido, halogen, alkyl, and alkoxy;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14\prime}$, and glycols;

$R^{14}$ is independently selected from the group consisting of: hydrido, and lower alkyl;

$R^{14\prime}$ is independently selected from the group consisting of: hydrido, and lower alkyl; and $R^{16}$ is independently selected from the group consisting of: hydrido, aryl, lower alkyl, haloalkyl, alkenyl, alkynyl, hydroxyalkyl, aminoalkyl, alkoxy, and alkoxyalkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, esters, prodrugs, or pharmaceutically acceptable salts thereof.

3. The compound of claim 2 of Formula II:

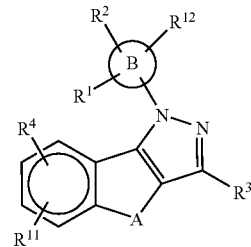

wherein

A is $-O-CH_2-$ or $-CH_2-S-$, wherein each $CH_2$ may be independently substituted with one or more substitution selected from the group consisting of: hydroxy, halo, alkoxy, lower alkyl, amino, aminoalkyl, alkylamino, alkenyl, and alkynyl;

B is a 5 or 6 membered heteroaryl, or aryl, optionally saturated, or optionally substituted with $R^1$, $R^2$, or $R^{12}$;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is hydrido;

$R^3$ is selected from the group consisting of: substituted or unsubstituted amidine, alkylamino, aminoalkyl, $CONHR^{16}$, $NH_2$, $NHCOR^6$, and $CH_2NHCOR^6$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is hydrido;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols, $R^{14}$ is independently selected from the group consisting of: hydrido, and lower alkyl; and $R^{14'}$ is independently selected from the group consisting of: hydrido, and lower alkyl; and $R^{16}$ is independently selected from the group consisting of: hydrido, aryl, lower alkyl, haloalkyl, alkenyl, alkynyl, hydroxyalkyl, aminoalkyl, alkoxy, and alkoxyalkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, esters, prodrugs, or pharmaceutically acceptable salts thereof.

4. The compound of claim 2 of Formula II:

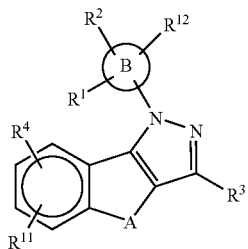

wherein

A is —O—CH$_2$— or —CH$_2$—S—; wherein each CH$_2$ may be independently substituted with one or more substitution selected from the group consisting of: hydroxy, halo, alkoxy, lower alkyl, amino, aminoalkyl, alkylamino, alkenyl, and alkynyl;

B is a 5 or 6 membered heteroaryl, or aryl, optionally saturated, or optionally substituted with R$^1$, R$^2$, or R$^{12}$;

R$^1$ is selected from the group consisting of: hydrido, halogen, alkyl, aryl, heteroaryl, alkenyl, alkynyl, haloalkyl, CN, NO$_2$, OR$^5$, OCOOR$^5$, CO$_2$R$^7$, CON(R$^6$)R$^7$, COR$^6$, SR$^6$, SOR$^6$, SO$_2$R$^6$, NR$^6$R$^7$, NR$^6$COR$^7$, NR$^6$CONHR$^7$, NR$^6$SO$_2$R$^7$, NR$^6$SO$_2$NHR$^7$, and SO$_2$N(R$^6$)R$^7$ wherein R$^6$ and R$^7$ may be taken together to form a 3–7 membered carbocyclic ring having 1 to 3 substituted or unsubstituted heteroatoms selected from the group consisting of: S, SO, SO$_2$, O, and NR$^6$; wherein said alkenyl, alkynyl, alkyl, aryl, heteroaryl or OR$^5$ are optional substituted with, hydrido, halogen, alkyl, hydroxyalkyl, aryl, heteroaryl, haloalkyl, COCF$_3$, CN, NO$_2$, OR$^5$, OCOOR$^5$, CO$_2$R$^7$, CON(R$^6$)R$^7$, COR$^6$, SR$^6$, SOR$^6$, SO$_2$R$^6$, NR$^6$R$^7$, NR$^6$COR$^7$, NR$^6$CONHR$^7$, NR$^6$SO$_2$R$^7$, NR$^6$SO$_2$NHR$^7$, and SO$_2$N(R$^6$)R$^7$ wherein R$^6$ R$^7$ may be taken together to form a 3–7 membered carbocyclic ring having 1 to 3 substituted or unsubstituted heteroatoms selected from the group consisting of: S, SO, SO$_2$, O, and NR$^6$;

R$^2$ is selected from the group consisting of: halogen, hydrido, hydroxyalkyl, alkyl, OR$^6$, CN, NO$_2$, SR$^6$, NHR$^6$, CON(R$^6$)R$^7$, NHCONHR$^6$, CO$_2$H, and haloalkyl;

R$^1$ and R$^2$ may be taken together to form a 5 to 7 membered saturated or unsaturated carbocyclic ring optionally containing 0 to 3 heteroatoms selected from the group consisting of: N, O, or S, and wherein said ring is optionally substituted with R$^1$;

R$^3$ is selected from the group consisting of: substituted or unsubstituted amidine, alkylamino, aminoalkyl, CONHR$^{16}$, NH$_2$, NHCOR$^6$, and CH$_2$NHCOR$^6$;

R$^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR$^{13}$, SR$^8$, SO$_2$N(R$^8$)R$^{8'}$, NHR$^9$, NHCOR$^9$, NR$^9$COR$^9$, NHCO(OR$^9$), NR$^9$CO(OR$^9$), NR$^8$SO$_2$R$^{10}$, NHSO$_2$N(R$^{10}$)R$^{10'}$, NR$^6$CON(R$^{10}$)R$^{10'}$, COR$^9$, CO$_2$R$^8$, CON(R$^8$)R$^{8'}$, wherein R$^8$ and R$^{8'}$ may be taken together to form a 3–7 membered carbocyclic ring having 1 to 3 substituted or unsubstituted heteroatoms selected from S, SO, SO$_2$, O, N, and NR$^6$, and wherein R$^{10}$ and R$^{10'}$ may be taken together to form a 3–7 membered carbocyclic ring having 1 to 3 substituted or unsubstituted heteroatoms selected from S, SO, SO$_2$, O, N, and NR$^6$ wherein said aryl, heterocyclic, heteroaryl, or alkenyl are optionally substituted with R$^9$;

R$^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: OR$^{14}$, N(R$^{14}$)R$^{14'}$, and glycols;

R$^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

R$^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R$^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is hydrido;

$R^{12}$ is hydrido;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^{14}$ is independently selected from the group consisting of: hydrido, and lower alkyl;

$R^{14'}$ is independently selected from the group consisting of: hydrido, and lower alkyl; and $R^{16}$ is independently selected from the group consisting of: hydrido, aryl, lower alkyl, haloalkyl, alkenyl, alkynyl, hydroxyalkyl, aminoalkyl, alkoxy, and alkoxyalkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, esters, prodrugs, or pharmaceutically acceptable salts thereof.

5. The compound of claim 2 of Formula II:

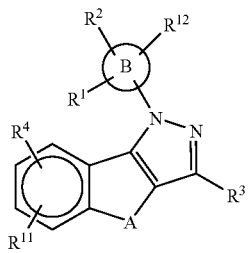

wherein

A is —O—CH$_2$— or —CH$_2$—S—, wherein each CH$_2$ may be independently substituted with one or more substitution selected from the group consisting of: hydroxy, halo, alkoxy, lower alkyl, amino, aminoalkyl, alkylamino, alkenyl, and alkynyl;

B is a 5 or 6 membered heteroaryl, or aryl, optionally saturated, or optionally substituted with $R^1$, $R^2$, or $R^{12}$;

$R^1$ is selected from the group consisting of: hydrido, halogen, alkyl, aryl, heteroaryl, alkenyl, alkynyl, haloalkyl, CN, NO$_2$, OR$^5$, OCOOR$^5$, CO$_2$R$^7$, CON(R$^6$)R$^7$, COR$^6$, SR$^6$, SOR$^6$, SO$_2$R$^6$, NR$^6$R$^7$, NR$^6$COR$^7$, NR$^6$CONHR$^7$, NR$^6$SO$_2$R$^7$, NR$^6$SO$_2$NHR$^7$, and SO$_2$N(R$^6$)R$^7$ wherein R$^6$ and R$^7$ may be taken together to form a 3–7 membered carbocyclic ring having 1 to 3 substituted or unsubstituted heteroatoms selected from the group consisting of: S, SO, SO$_2$, O, and NR$^6$; wherein said alkenyl, alkynyl, alkyl, aryl, heteroaryl or OR$^5$ are optional substituted with, hydrido, halogen, alkyl, hydroxyalkyl, aryl, heteroaryl, haloalkyl, COCF$_3$, CN, NO$_2$, OR$^5$, OCOOR$^5$, CO$_2$R$^7$, CON(R$^6$)R$^7$, COR$^6$, SR$^6$, SOR$^6$, SO$_2$R$^6$, NR$^6$R$^7$, NR$^6$COR$^7$, NR$^6$CONHR$^7$, NR$^6$SO$_2$R$^7$, NR$^6$SO$_2$NHR$^7$, and SO$_2$N(R$^6$)R$^7$ wherein R$^6$ and R$^7$ may be taken together to form a 3–7 membered carbocyclic ring having 1 to 3 substituted or unsubstituted heteroatoms selected from the group consisting of: S, SO, SO$_2$, O, and NR$^6$;

$R^2$ is hydrido;

$R^3$ is selected from the group consisting of: substituted or unsubstituted amidine, alkylamino, aminoalkyl, CONHR$^{16}$, NH$_2$, NHCOR$^6$, and CH$_2$NHCOR$^6$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR$^{13}$, SR$^8$, SO$_2$N(R$^8$)R$^{8'}$, NHR$^9$, NHCOR$^9$, NR$^9$COR$^9$, NHCO(OR$^9$), NR$^9$CO(OR$^9$), NR$^8$SO$_2$R$^{10}$, NHSO$_2$N(R$^{10}$)R$^{10'}$, NR$^6$CON(R$^{10}$)R$^{10'}$, COR$^9$, CO$_2$R$^8$, CON(R$^8$)R$^{8'}$, wherein R$^8$ and R$^{8'}$ may be taken together to form a 3–7 membered carbocyclic ring having 1 to 3 substituted or unsubstituted heteroatoms selected from S, SO, SO$_2$, O, N, and NR$^6$, and wherein R$^{10}$ and R$^{10'}$ may be taken together to form a 3–7 membered carbocyclic ring having 1 to 3 substituted or unsubstituted heteroatoms selected from S, SO, SO$_2$, O, N, and NR$^6$ wherein said aryl, heterocyclic, heteroaryl, or alkenyl are optionally substituted with R$^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: OR$^{14}$, N(R$^{14}$)R$^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is hydrido;

$R^{12}$ is hydrido;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^{14}$ is independently selected from the group consisting of: hydrido, and lower alkyl;

$R^{14'}$ is independently selected from the group consisting of: hydrido, and lower alkyl; and $R^{16}$ is independently selected from the group consisting of: hydrido, aryl, lower alkyl, haloalkyl, alkenyl, alkynyl, hydroxyalkyl, aminoalkyl, alkoxy, and alkoxyalkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, esters, prodrugs, or pharmaceutically acceptable salts thereof.

6. The compound of claim 2 of formula II:

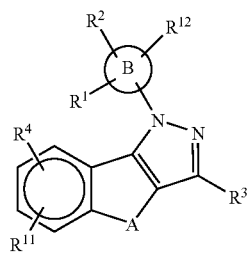

wherein

A is —O—CH$_2$— or —CH$_2$—S—, wherein each CH$_2$ may be independently substituted with one or more substitution selected from the group consisting of: hydroxy, halo, alkoxy, lower alkyl, amino, aminoalkyl, alkylamino, alkenyl, and alkynyl;

B is a 5 or 6 membered heteroaryl, or aryl, optionally saturated, or optionally substituted with $R^1$, $R^2$, or $R^{12}$;

$R^1$ is selected from the group consisting of: hydrido, halogen, alkyl, aryl, heteroaryl, alkenyl, alkynyl, haloalkyl, CN, NO$_2$, OR$^5$, OCOOR$^5$, CO$_2$R$^7$, CON(R$^6$)R$^7$, COR$^6$, SR$^6$, SOR$^6$, SO$_2$R$^6$, NR$^6$R$^7$, NR$^6$COR$^7$, NR$^6$CONHR$^7$, NR$^6$SO$_2$R$^7$, NR$^6$SO$_2$NHR$^7$, and SO$_2$N(R$^6$)R$^7$ wherein R$^6$ and R$^7$ may be taken together to form a 3–7 membered carbocyclic ring having 1 to 3 substituted or unsubstituted heteroatoms selected from the group consisting of: S, SO, SO$_2$, O, and NR$^6$; wherein said alkenyl, alkynyl, alkyl, aryl, heteroaryl or OR$^5$ are optional substituted with, hydrido, halogen, alkyl, hydroxyalkyl, aryl, heteroaryl, haloalkyl, COCF$_3$, CN, NO$_2$, OR$^5$, OCOOR$^5$, CO$_2$R$^7$, CON(R$^6$)R$^7$, COR$^6$, SR$^6$, SOR$^6$, SO$_2$R$^6$, NR$^6$R$^7$, NR$^6$COR$^7$, NR$^6$CONHR$^7$, NR$^6$SO$_2$R$^7$, NR$^6$SO$_2$NHR$^7$, and SO$_2$N(R$^6$)R$^7$ wherein R$^6$ R$^7$ may be taken together to form a 3–7 membered carbocyclic ring having 1 to 3 substituted or unsubstituted heteroatoms selected from the group consisting of: S, SO, SO$_2$, O, and NR$^6$;

$R^2$ is selected from the group consisting of: halogen, hydrido, hydroxyalkyl, alkyl, OR$^6$, CN, NO$_2$, SR$^6$, NHR$^6$, CON(R$^6$)R$^7$, NHCONHR$^6$, CO$_2$H, and haloalkyl;

$R^1$ and $R^2$ may be taken together to form a 5 to 7 membered saturated or unsaturated carbocyclic ring optionally containing 0 to 3 heteroatoms selected from the group consisting of: N, O, or S, and wherein said ring is optionally substituted with $R^1$;

$R^3$ is selected from the group consisting of: substituted or unsubstituted amidine, alkylamino, aminoalkyl, CONHR$^{16}$, NH$_2$, NHCOR$^6$, and CH$_2$NHCOR$^6$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR$^{13}$, SR$^8$, SO$_2$N(R$^8$)R$^{8'}$, NHR$^9$, NHCOR$^9$, NR$^9$COR$^9$, NHCO(OR$^9$), NR$^9$CO(OR$^9$), NR$^8$SO$_2$R$^{10}$, NHSO$_2$N(R$^{10}$)R$^{10'}$, NR$^6$CON(R$^{10}$)R$^{10'}$, COR$^9$, CO$_2$R$^8$, CON(R$^8$)R$^{8'}$, wherein R$^8$ and R$^{8'}$ may be taken together to form a 3–7 membered carbocyclic ring having 1 to 3 substituted or unsubstituted heteroatoms selected from S, SO, SO$_2$, O, N, and NR$^6$, and wherein R$^{10}$ and R$^{10'}$ may be taken together to form a 3–7 membered carbocyclic ring having 1 to 3 substituted or unsubstituted heteroatoms selected from S, SO, SO$_2$, O, N, and NR$^6$ wherein said aryl, heterocyclic, heteroaryl, or alkenyl are optionally substituted with R$^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: OR$^{14}$, N(R$^{14}$)R$^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is selected from the group consisting of: hydrido, halogen, alkyl, and alkoxy;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^{14}$ is independently selected from the group consisting of: hydrido, and lower alkyl;

$R^{14'}$ is independently selected from the group consisting of: hydrido, and lower alkyl; and $R^{16}$ is independently selected from the group consisting of: hydrido, aryl, lower alkyl, haloalkyl, alkenyl, alkynyl, hydroxyalkyl, aminoalkyl, alkoxy, and alkoxyalkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, esters, prodrugs, or pharmaceutically acceptable salts thereof.

7. The compound of claim 6:

wherein

A is —O—$CH_2$— or —$CH_2$—S—, wherein each $CH_2$ may be independently substituted with one or more substitution selected from the group consisting of: hydroxy, halo, alkoxy, lower alkyl, amino, aminoalkyl, alkylamino, alkenyl, and alkynyl;

B is a 6 membered heteroaryl, or aryl, optionally saturated, or optionally substituted with $R^1$, $R^2$, or $R^{12}$;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is hydrido;

$R^3$ is $CONH_2$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic.

$R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is hydrido;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^{14}$ is independently selected from the group consisting of: hydrido, and lower alkyl;

$R^{14'}$ is independently selected from the group consisting of: hydrido, and lower alkyl; and with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, esters, prodrugs, or pharmaceutically acceptable salts thereof.

8. The compound of claim 7 wherein

A —O—CH$_2$— or —CH$_2$—S—, wherein each CH$_2$ may be independently substituted with one or more substitution selected from the group consisting of: hydroxy, halo, alkoxy, lower alkyl, amino, aminoalkyl, alkylamino, alkenyl, and alkynyl;

$R^1$ is selected from the group consisting of: $SO_2R^6$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, SO$_2$, O, and $NR^6$;

$R^2$ is hydrido;

$R^3$ is $CONH_2$ $R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, SO$_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, SO$_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{11}$ is hydrido;

$R^{12}$ is hydrido;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^{14}$ is independently selected from the group consisting of: hydrido, and lower alkyl; and $R^{14'}$ is independently selected from the group consisting of: hydrido, and lower alkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, esters, prodrugs, or pharmaceutically acceptable salts thereof.

9. The compound of claim 6 of the formula:

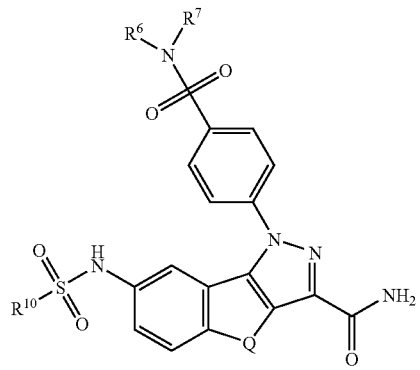

wherein

Q is —O—CH$_2$— or —CH$_2$—S—;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic wherein $R^6$ and $R^7$ may be taken together to form a 3–7 membered carbocyclic ring having 1 to 3 substituted or unsubstituted heteroatoms selected from the group consisting of: S, SO, SO$_2$, O, and NR$^6$;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, or tautomers, esters, prodrugs, or pharmaceutically acceptable salts thereof.

10. The compound of claim 6 of the formula:

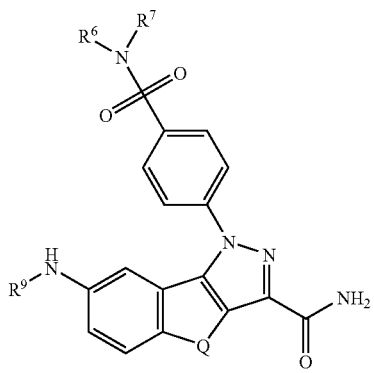

wherein

Q is —O—CH$_2$— or —CH$_2$—S—;

R$^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic wherein R$^6$ and R$^7$ may be taken together to form a 3–7 membered carbocyclic ring having 1 to 3 substituted or unsubstituted heteroatoms selected from the group consisting of: S, SO, SO$_2$, O, and NR$^6$;

R$^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

or tautomers, esters, prodrugs, or pharmaceutically acceptable salts thereof.

11. The compound of claim 6 of the formula:

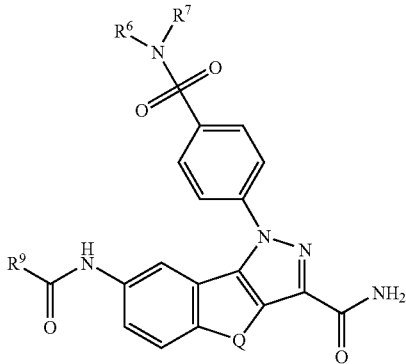

wherein

Q is —O—CH$_2$— or —CH$_2$—S—;

R$^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic wherein R$^6$ and R$^7$ may be taken together to form a 3–7 membered carbocyclic ring having 1 to 3 substituted or unsubstituted heteroatoms selected from the group consisting of: S, SO, SO$_2$, O, and NR$^6$;

R$^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

or tautomers, esters, prodrugs, or pharmaceutically acceptable salts thereof.

12. The compound of claim 2 of the formula:

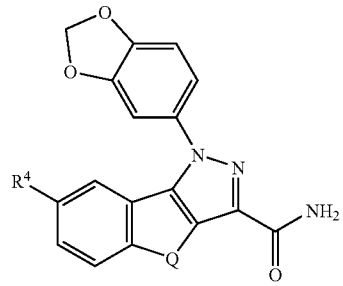

wherein

Q is —O—CH$_2$— or —CH$_2$—S—;

R$^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR$^{13}$, SR$^8$, SO$_2$N(R$^8$)R$^{8'}$, NHR$^9$, NHCOR$^9$, NR$^9$COR$^9$, NHCO(OR$^9$), NR$^9$CO(OR$^9$), NR$^8$SO$_2$R$^{10}$, NHSO$_2$N(R$^{10}$)R$^{10'}$, NR$^6$CON(R$^{10}$)R$^{10'}$, COR$^9$, CO$_2$R$^8$, CON(R$^8$)R$^{8'}$, wherein R$^8$ and R$^{8'}$ may be taken together to form a 3–7 membered carbocyclic ring having 1 to 3 substituted or unsubstituted heteroatoms selected from S, SO, SO$_2$, O, N, and NR$^6$, and wherein R$^{10}$ and R$^{10'}$ may be taken together to form a 3–7 membered carbocyclic ring having 1 to 3 substituted or unsubstituted heteroatoms selected from S, SO, SO$_2$, O, N, and NR$^6$ wherein said aryl, heterocyclic, heteroaryl, or alkenyl are optionally substituted with R$^9$;

R$^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

R$^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R$^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, R$^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: OR$^{14}$, N(R$^{14}$)R$^{14'}$, and glycols;

R$^{14}$ is independently selected from the group consisting of: hydrido, and lower alkyl; and R$^{14'}$ is independently selected from the group consisting of: hydrido, and lower alkyl;

with the proviso that when R$^1$ is sulfamyl, then R$^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when R$^4$ is sulfamyl, then R$^1$ is not sulfamyl, halogen, alkyl, alkoxy, hydroxyl and haloalkyl;

or tautomers, esters, prodrugs, or pharmaceutically acceptable salts thereof.

13. The compound of claim 12 that is amino-1-[1,3-benzodioxol-5-yl]-1,4-dihydrochromeno[4,3-c]pyrazole-3-carboxamide.

14. The compound of claim 2 of the formula:

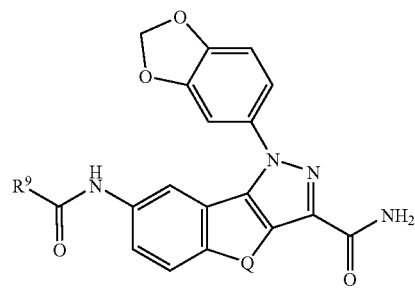

wherein

Q is —O—CH$_2$— or —CH$_2$—S—;

R$^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

or tautomers, esters, prodrugs, or pharmaceutically acceptable salts thereof.

15. The compound of claim 14 selected from the group consisting of:

1-(1,3-benzodioxol-5-yl)-8-{[(2-chloropyridin-3-yl)carbonyl]amino}-1,4-dihydrochromeno[4,3-c]pyrazole-3-carboxamide, 1-(1,3-benzodioxol-5-yl)-8-{[(6-chloro-1,3-benzodioxol-5-yl)carbonyl]amino}-1,4-dihydrochromeno[4,3-c]pyrazole-3-carboxamide, 1-(1,3-benzodioxol-5-yl)-8-[(3-chloroisonicotinoyl)amino]-1,4-dihydrochromeno[4,3-c]pyrazole-3-carboxamide, 8-[(5-amino-2-chlorobenzoyl)amino]-1-(1,3-benzodioxol-5-yl)-1,4-dihydrochromeno[4,3-c]pyrazole-3-carboxamide, 1-(1,3-benzodioxol-5-yl)-8-[(2-chlorobenzoyl)amino]-1,4-dihydrochromeno[4,3-c]pyrazole-3-carboxamide, 1-(1,3-benzodioxol-5-yl)-8-[(2-chloro-4,5-dimethoxybenzoyl)amino]-1,4-dihydrochromeno[4,3-c]pyrazole-3-carboxamide, 1-(1,3-benzodioxol-5-yl)-8-{[2-chloro-5-(methylsulfinyl)benzoyl]amino}-1,4-dihydrochromeno[4,3-c]pyrazole-3-carboxamide, 1-(1,3-benzodioxol-5-yl)-8-[(3-hydroxy-2-methylbenzoyl)amino]-1,4-dihydrochromeno[4,3-c]pyrazole-3-carboxamide, 1-(1,3-benzodioxol-5-yl)-8-[(2-chloro-4-nitrobenzoyl)amino]-1,4-dihydrochromeno[4,3-c]pyrazole-3-carboxamide, 1-(1,3-benzodioxol-5-yl)-8-{[2-chloro-5-(dimethylamino)benzoyl]amino}-1,4-dihydrochromeno[4,3-c]pyrazole-3-carboxamide, 1-(1,3-benzodioxol-5-yl)-8-{[(2,5-dichloropyridin-3-yl)carbonyl]amino}-1,4-dihydrochromeno[4,3-c]pyrazole-3-carboxamide, 1-(1,3-benzodioxol-5-yl)-8-[(2-chloro-4-methoxybenzoyl)amino]-1,4-dihydrochromeno[4,3-c]pyrazole-3-carboxamide, 8-[(4-amino-2-chlorobenzoyl)amino]-1-(1,3-benzodioxol-5-yl)-1,4-dihydrochromeno[4,3-c]pyrazole-3-carboxamide, 1-(1,3-benzodioxol-5-yl)-8-[(3-methoxy-2-methylbenzoyl)amino]-1,4-dihydrochromeno[4,3-c]pyrazole-3-carboxamide, 3-({[3-(aminocarbonyl)-1-(1,3-benzodioxol-5-yl)-1,4-dihydrochromeno[4,3-c]pyrazol-8-yl]amino}carbonyl)-2-methylphenyl acetate, 1-(1,3-benzodioxol-5-yl)-8-[(2,3-dichlorobenzoyl)amino]-1,4-dihydrochromeno[4,3-c]pyrazole-3-carboxamide, and 1-(1,3-benzodioxol-5-yl)-8-[(2-chloro-5-nitrobenzoyl)amino]-1,4-dihydrochromeno[4,3-c]pyrazole-3-carboxamide.

16. The compound of claim 2 of the formula:

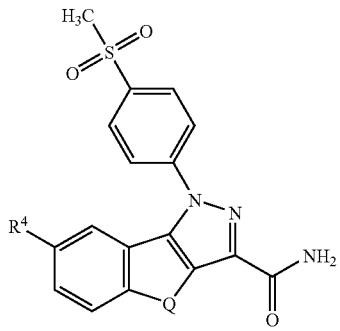

wherein

Q is —O—CH$_2$— or —CH$_2$—S—;

R$^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, OR$^{13}$, SR$^8$, SO$_2$N(R$^8$)R$^{8'}$, NHR$^9$, NHCOR$^9$, NR$^9$COR$^9$, NHCO(OR$^9$), NR$^9$CO(OR$^9$), NR$^8$SO$_2$R$^{10}$, NHSO$_2$N(R$^{10}$)R$^{10'}$, NR$^6$CON(R$^{10}$)R$^{10'}$, COR$^9$, CO$_2$R$^8$, CON(R$^8$)R$^{8'}$, wherein R$^8$ and R$^{8'}$ may be taken together to form a 3–7 membered carbocyclic ring having 1 to 3 substituted or unsubstituted heteroatoms selected from S, SO, SO$_2$, O, N, and NR$^6$, and wherein R$^{10}$ and R$^{10'}$ may be taken together to form a 3–7 membered carbocyclic ring having 1 to 3 substituted or unsubstituted heteroatoms selected from S, SO, SO$_2$, O, N, and NR$^6$ wherein said aryl, heterocyclic, heteroaryl, or alkenyl are optionally substituted with R$^9$;

R$^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

R$^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

R$^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: $OR^{14}$, $N(R^{14})R^{14'}$, and glycols;

$R^{14}$ is independently selected from the group consisting of: hydrido, and lower alkyl; and $R^{14'}$ is independently selected from the group consisting of: hydrido, and lower alkyl;

with the proviso that when $R^1$ is sulfamyl, then $R^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when $R^4$ is sulfamyl, then $R^1$ is not sulfamyl, halogen, alkyl, alkoxy, hydroxyl and haloalkyl;

or tautomers, esters, prodrugs, or pharmaceutically acceptable salts thereof.

17. The compound of claim 2 of the formula:

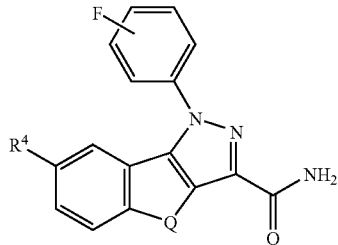

wherein
Q is —O—CH$_2$— or —CH$_2$—S—;
$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, SO$_2$, O, N, and NR$^6$, and wherein $R^{10}$ and $R^{10'}$ may be taken together to form a 3–7 membered carbocyclic ring having 1 to 3 substituted or unsubstituted heteroatoms selected from S, SO, SO$_2$, O, N, and NR$^6$ wherein said aryl, heterocyclic, heteroaryl, or alkenyl are optionally substituted with $R^9$;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic, $R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of: OR$^{14}$, N(R$^{14}$)R$^{14'}$, and glycols;

R$^{14}$ is independently selected from the group consisting of: hydrido, and lower alkyl; and R$^{14'}$ is independently selected from the group consisting of: hydrido, and lower alkyl;

with the proviso that when R$^1$ is sulfamyl, then R$^4$ is not halogen, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro, and acylamino, and/or when R$^4$ is sulfamyl, then R$^1$ is not sulfamyl, halogen, alkyl, alkoxy, hydroxyl and haloalkyl;

or tautomers, esters, prodrugs, or pharmaceutically acceptable salts thereof.

18. The compound according to claim 17 selected from the group consisting of:

8-{[(2-chloropyridin-3-yl)carbonyl]amino}-1-(4-fluorophenyl)-1,4-dihydrochromeno[4,3-c]pyrazole-3-carboxamide, 8-{[(2-chloropyridin-3-yl)carbonyl]amino}-1-(3-fluorophenyl)-1,4-dihydrochromeno[4,3-c]pyrazole-3-carboxamide, 8-[(2-chlorobenzoyl)amino]-1-(4-fluorophenyl)-1,4-dihydrochromeno[4,3-c]pyrazole-3-carboxamide, 8-[(2-chlorobenzoyl)amino]-1-(3-fluorophenyl)-1,4-dihydrochromeno[4,3-c]pyrazole-3-carboxamide, 8-[(2,3-dichlorobenzoyl)amino]-1-(3-fluorophenyl)-1,4-dihydrochromeno[4,3-c]pyrazole-3-carboxamide, 8-amino-1-(4-fluorophenyl)-1,4-dihydrochromeno[4,3-c]pyrazole-3-carboxamide, and 8-[(3-chloroisonicotinoyl)amino]-1-(4-fluorophenyl)-1,4-dihydrochromeno[4,3-c]pyrazole-3-carboxamide.

19. The compound according to claim 6 selected from the group consisting of:

ethyl 1-{4-[(aminothio)peroxy]phenyl}-8-fluoro-1,4-dihydrochromeno[4,3-c]pyrazole-3-carboxylate, 1-{4-[(aminothio)peroxy]phenyl}-8-fluoro-1,4-dihydrochromeno[4,3-c]pyrazole-3-carboxamide, ethyl 1-{4-[(aminothio)peroxy]phenyl}-1,5-dihydroisothiochromeno[4,3-c]pyrazole-3-carboxylate, ethyl 1-{4-[(aminothio)peroxy]phenyl}-1,5-dihydroisothiochromeno[4,3-c]pyrazole-3-carboxylate, 1-{4-[(aminothio)peroxy]phenyl}-1,5-dihydroisothiochromeno[4,3-c]pyrazole-3-carboxamide, 8-{4-[(aminothio)peroxy]phenyl}-4,8-dihydro[1,3]dioxolo[7,8]isothiochromeno[4,3-c]pyrazole-6-carboxamide, 1-[4-(aminosulfonyl)phenyl]-1,4-dihydrochromeno[4,3-c]pyrazole-3-carboxamide, 8-[(2-chlorobenzoyl)amino]-1-[4-(methylsulfonyl)phenyl]-1,4-dihydrochromeno[4,3-c]pyrazole-3-carboxamide, 8-[(2-chlorobenzoyl)amino]-1-[4-(methylsulfinyl)phenyl]-1,4-dihydrochromeno[4,3-c]pyrazole-3-carboxamide, and 8-[(2-chlorobenzoyl)amino]-1-[4-(methylthio)phenyl]-1,4-dihydrochromeno[4,3-c]pyrazole-3-carboxamide.

20. A composition comprising the compound of claim 1 or 2 and at least one pharmaceutically acceptable carrier.

* * * * *